US006828460B2

(12) United States Patent
Browning et al.

(10) Patent No.: US 6,828,460 B2
(45) Date of Patent: Dec. 7, 2004

(54) RESORCINOL DERIVATIVES

(75) Inventors: Andrew Francis Browning, Bjorksta (SE); Eric William Collington, Knebworth (GB); Martin James Procter, Walsall (GB); Joanna Victoria Geden, Coventry (GB)

(73) Assignee: Pfizer Inc., Groton, CT (US)

( * ) Notice: Subject to any disclaimer, the term of this patent is extended or adjusted under 35 U.S.C. 154(b) by 30 days.

(21) Appl. No.: 10/020,037

(22) Filed: Dec. 21, 2001

(65) Prior Publication Data

US 2002/0161041 A1 Oct. 31, 2002

Related U.S. Application Data

(63) Continuation-in-part of application No. 09/526,287, filed on Mar. 15, 2000, now abandoned.
(60) Provisional application No. 60/125,534, filed on Mar. 22, 1999.

(51) Int. Cl.$^7$ .............................................. C07C 249/00
(52) U.S. Cl. ...................... 564/256; 514/640; 514/730; 564/99; 564/253; 564/300; 560/50; 560/73; 560/107; 568/731; 568/743
(58) Field of Search ................................. 564/256, 253, 564/99, 300; 568/743, 731; 514/640, 730; 560/50, 73, 107

(56) References Cited

U.S. PATENT DOCUMENTS

| | | | |
|---|---|---|---|
| 3,697,275 A | | 10/1972 | Hayakawa et al. |
| 3,756,818 A | | 9/1973 | Havakawa et al. |
| 3,933,925 A | | 1/1976 | Greco |
| 4,225,619 A | | 9/1980 | Brickl et al. |
| 4,306,097 A | | 12/1981 | Harbert et al. |
| 4,391,827 A | | 7/1983 | Harbert et al. |
| 4,515,773 A | * | 5/1985 | Herlihy |
| 4,609,544 A | * | 9/1986 | Herlihy |
| 4,959,393 A | * | 9/1990 | Torihara |
| 5,258,544 A | | 11/1993 | Reilly, Jr. et al. |
| 5,304,679 A | | 4/1994 | McEvily et al. |
| 5,399,785 A | * | 3/1995 | Miura |
| 5,468,472 A | | 11/1995 | LaGrange et al. |
| 5,508,155 A | | 4/1996 | Marrese et al. |
| 5,620,835 A | | 4/1997 | Marrese et al. |
| 5,702,637 A | | 12/1997 | Johson et al. |
| 6,132,740 A | * | 10/2000 | Hu |
| 6,504,037 B2 | * | 1/2003 | Bradley |

FOREIGN PATENT DOCUMENTS

| | | |
|---|---|---|
| CA | 2094465 | 10/1993 |
| DE | 3127590 A1 | 7/1980 |
| DE | 3604865 A1 | 8/1987 |
| DE | 44 37 999 A1 | 10/1994 |
| DE | 44 38 021 A1 | 10/1994 |
| DE | 44 38 055 A1 | 10/1994 |
| EP | 0 278 742 A2 | 2/1988 |
| EP | 0 341 664 | 5/1989 |
| EP | 0 518 533 A1 | 12/1992 |
| EP | 0 524 439 A1 | 1/1993 |
| EP | 0 551 849 A1 | 7/1993 |
| EP | 0 618 193 A1 | 10/1994 |
| EP | 0 623 339 A1 | 11/1994 |
| EP | 0 701 988 A1 | 3/1996 |
| EP | 0 810 213 A2 | 12/1997 |
| EP | 0 904 774 A1 | 3/1999 |
| JP | 2-49715 | 2/1990 |
| JP | 4-169516 | 5/1992 |
| JP | 5-4905 | 1/1993 |
| JP | 6-56641 | 3/1994 |
| JP | 11-246339 | * 9/1999 |
| WO | WO 90/13618 | 11/1990 |
| WO | WO 91/11119 | 8/1991 |
| WO | WO 92/09566 | 6/1992 |
| WO | WO 92/14692 | 9/1992 |
| WO | WO 93/16052 | 8/1993 |
| WO | WO 93/24446 | 12/1993 |
| WO | WO 95/00131 | 1/1995 |
| WO | WO 95/19344 | 7/1995 |
| WO | WO 96/02250 A1 | 2/1996 |
| WO | WO 96/13262 | 5/1996 |
| WO | WO 96/33251 | 10/1996 |
| WO | WO 97/15549 | 5/1997 |
| WO | WO 97/17349 | 5/1997 |
| WO | WO 98/18786 | 5/1998 |
| WO | WO 98/57641 | 12/1998 |
| WO | WO-99/15148 | * 4/1999 |

OTHER PUBLICATIONS

Chemical Abstracts, vol. 63, 1965; pp 6872.

Chemical Abstracts, vol. 52; pp 10391–10392, (1954).

Chemical Abstracts, vol. 51; pp 1463–1464, (1954).

Chemical Abstracts H, (1957), 51:13219b.

Repinskaya, I.B., et al, "Reaction of Phenols And Their Derivatives With Aromatic Compounds In The Presence Of Acidic Agents", Zhurnal Organicheskoi Khimll, vol. 16, No. 7, 1980; pp 1508–1514.

Gottesfeld, N.H., et al, "The Inhibition of Deoxyribonuclease I by Hydroxybiphenls", Biochim. Biophys. Acta, 228, 1971; pp 365–386.

Baek, S., et al, "A Simple One–Step Synthesis of Alkylation Product From Cyclic Allylic Alcohol and Resorcinol", Arch. Pharm. Res., 15(4), 1992; pp 304–308.

Czuchajowski, L., et al, "Quinhydrones and Semiquinones in Coal and Humic Acids in View of Quantum Chemical Consideration of Their IR Absorption", Ann. Soc. Chim. Polonorum, 63, 1969; pp 1451–1456.

(List continued on next page.)

*Primary Examiner*—Michael L. Shippen
(74) *Attorney, Agent, or Firm*—Alan L. Koller; J. Michael Dixon; Rosanne Goodman

(57) ABSTRACT

The present invention relates to the use of certain resorcinol derivatives as skin lightening agents.

41 Claims, No Drawings

OTHER PUBLICATIONS

Czuchajowski, L., et al, "Skeletal and C×O Stretching Vibrations in the IR Absorption Spectra of Phenyl– and Benzylbenzoquinones", Ann. Soc. Chim., 44, 1970; pp 2395–2402.

McEvily, A., et al, "Inhibition of Polyphenyl Oxidase by Phenolic Compounds", American Chemical Society, 1992; pp 318–325.

Baek, Seung–Hwa, "Simplified Cannabidiols. Part 1. Boron Trifluoride–Diethyl Ether on Alumina: A Modified Lewis Acid Reagent. Friedel–Crafts Alkylation of 5–Alkylresorcinols with Cyclic Allylic Alcohols", J. Chem. Research, 1994, 451.

Repinskaya, I.B., et al, "Interaction of Phenols and Their Derivatives With Aromatic Compounds in the Presence of Acid Agents", Journal of Organic Chemistry, vol. XVI, No. 7, 1980; pp 1–9.

Fukujiro, F., et al, "Studies on Antiseptics for Foodstuff. LXXIII", vol. 92, 1972; pp 768–771.

Yusupov, A., et al, "Reaction of Resorcinol and its Methyl Esters with Cyclopentene and Cyclohexene", Uzbek Chemical Journal, No. 5, 1970—Translated Copy pp. 1–5.

Ardurasuleva, A.R., et al, "Cyclopentylation of Resorcinol and its Esters", Uzbek Chemical Journal, No. 5, 1968—Translated Copy pp 1–5.

Yusupov, A., et al, "Cyclo–Alkylation of Resorcinol and its Esters", Reports of the Uzbek SSR Academy of Sciences, No. 6, 1970—Translated Copy pp 1–3.

Pisanenko, D.A., et al, "Antimicrobial Activity of Cycloalkenyl– and 4–(a–ARYL Cyclopentyl)–Phenols", Chernovitskiy Medical Institute, Polytechnic Institute, Submitted Nov. 9, 1976; pp 1&3 Translation Only.

* cited by examiner

RESORCINOL DERIVATIVES

This application is a continuation-in-part of U.S. application Ser. No. 09/526,287, filed Mar. 15, 2000, which claims priority from U.S. provisional application Ser. No. 60/125,534, filed Mar. 22, 1999.

FIELD OF THE INVENTION

The present invention relates to the use of certain resorcinol derivatives as skin lightening agents.

BACKGROUND OF THE INVENTION

The terms "lightening agent" and "depigmentation agent" are used interchangeably throughout this document.

Skin color in humans arises from a complex series of cellular processes that are carried out within a unique population of cells called melanocytes. Melanocytes are located in the lower part of the epidermis, and their function is to synthesize a pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin-containing melanosomes. The end result is that the visible layers of the skin exhibit a brown color typically known as a "tan". The darkness of the color observed in the skin is proportionate to the amount of melanin synthesized by melanocytes and transferred to the keratinocytes.

The mechanism by which skin pigmentation is formed, melanogenesis, is particularly complex and schematically involves the following main steps: Tyrosine→L-Dopa→Dopaquinone→Dopachrome→Melanins. The first two reactions in this series are catalyzed by the enzyme tyrosinase. The activity of tyrosinase is promoted by the action of α-melanocyte stimulating hormone or UV rays to have melanin eventually formed as chromatism in the skin. It is well established that a substance has a depigmenting effect if it acts directly on the vitality of the epidermal melanocytes where melanogenesis normally occurs and/or if it interferes with one of the stages in melanin biosynthesis. The active compounds that are employed in the various methods and compositions of this invention inhibit tyrosinase and thus inhibit or decrease melanin biosynthesis.

There is a strong demand for agents that enable acquired deposition sites, such as spots or freckles, to be restored to a normal skin color. For this purpose, a variety of agents and methods have been developed and put on the market. Examples of such methods are (a) a method wherein vitamin C (L-ascorbic acid) having good reducing ability is administered orally in large amounts, (b) a method wherein glutathione is administered parenterally; (c) a method wherein a peroxide, such as hydrogen peroxide, zinc peroxide, sodium peroxide and the like, which is believed to have the bleaching action of melamine, is administered: and (d) a method wherein vitamin C or cysteine is administered topically in the form of an ointment, cream, lotion or the like. Vitamin C has a problem with respect to stability and becomes so unstable in water-containing systems that they will cause changes in odor and color. Thiol compounds such as glutathione and cysteine do not exhibit a satisfactory depigmental effect since the development of the effect is very slow.

The substances in widest use at the present time as depigmentors are, in particular, hydroquinone and its derivatives, particularly its ethers such as hydroquinone monomethyl ether. These compounds, while effective, are known to produce side effects that can be dangerous. Hydroquinone, use of which is limited to a concentration of 2%, is both irritating and cytotoxic to the melanocyte.

U.S. Pat. No. 4,526,179 refers to certain hydroquinone fatty esters that have good activity and are less irritating and more stable than hydroquinone.

Japanese Patent Application No. 27909/86 refers to other hydroquinone derivatives that do not have the drawbacks of hydroquinone but that have relatively poor efficacy.

U.S. Pat. No. 5,449,518 refers to 2,5-dihydoxyphenyl carboxylic acid derivatives as skin depigmentation agents.

European Patent Application EP 341,664A1 refers to certain resorcinol derivatives as tyrosinase inhibitors and skin depigmentation agents.

PCT International Publication WO 99/15148 refers to certain resorcinol derivatives as tyrosinase inhibitors and skin depigmentation agents.

The use of topical depigmention agents that have good efficacy and are harmless is particularly desirable for treating the following: regional hyperpigmentation caused by melanocytic hyperactivity, such as idiopathic melasma occurring either during pregnancy (mask of pregnancy or chloasma) or secondary to estrogen-progesterone contraception; local hyperpigmentation caused by benign melanocytic hyperactivity and proliferation such as lentigo senilis or liver spots; accidental hyperpigmentation such as post-lesional photosensitization and scarring; and certain forms of leukoderma such as vitiligo where, if the injured skin cannot be repigmented, the residual zones of normal skin are depigmented to impart a homogeneous white color to the entire skin.

SUMMARY OF INVENTION

The resorcinol derivatives of formula I, which are defined below and used in the various methods and compositions of this invention, are useful in the treatment of the foregoing dermatological conditions as well as other dermatological conditions, some of which are referred to later in this document, for which the subject being treated desires, for medicinal or cosmetic purposes, to lighten or reduce the pigmentation of the skin affected by the condition.

The resorcinol derivatives of formula I are also useful for the treatment of inflammatory disorders such as psoriasis, dermatitis and acne, and for the treatment of dandruff.

The invention thus provides a compound of formula 1:

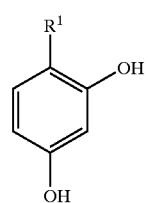

or a pharmaceutically acceptable salt thereof, wherein:

$R^1$ is a $(C_3-C_8)$cycloalkyl ring or $(C_5-C_8)$cycloalkenyl ring, wherein either the cycloalkyl ring or cycloalkenyl ring is substituted by one to three substituents independently selected from the group consisting of cyano; halo; $(C_1-C_6)$alkyl; aryl; $(C_2-C_9)$heterocycloalkyl; $(C_2-C_9)$heteroaryl; aryl$(C_1-C_6)$alkyl-; =O; =CHO $(C_1-C_6)$alkyl; amino; hydroxy; $(C_1-C_6)$alkoxy; aryl ($C_1$–$C_6$)alkoxy-; ($C_1$–$C_6$)acyl; ($C_1$–$C_6$)alkylamino-; aryl($C_1$–$C_6$)alkylamino-; amino($C_1$–$C_6$)alkyl-; ($C_1$–$C_6$)alkoxy-CO—NH—; ($C_1$–$C_6$)alkylamino-CO—; ($C_2$–$C_6$)alkenyl; ($C_2$–$C_6$)alkynyl; hydroxy($C_1$–$C_6$)alkyl-; ($C_1$–$C_6$)alkoxy($C_1$–$C_6$)alkyl-; ($C_1$–$C_6$) acyloxy($C_1$–$C_6$)alkyl-; nitro; cyano($C_1$–$C_6$)alkyl-; halo($C_1$–$C_6$)alkyl-; nitro($C_1$–$C_6$)alkyl-; trifluoromethyl; trifluoromethyl($C_1$–$C_6$)alkyl-; ($C_1$–$C_6$)acylamino-; ($C_1$–$C_6$)acylamino($C_1$–$C_6$)alkyl-; ($C_1$–$C_6$)alkoxy($C_1$–$C_6$)acylamino-; amino($C_1$–$C_6$)acyl-; amino($C_1$–$C_6$)acyl($C_1$–$C_6$)alkyl-; ($C_1$–$C_6$)alkylamino($C_1$–$C_6$)acyl-; (($C_1$–$C_6$) alkyl)$_2$amino($C_1$–$C_6$)acyl-; —$CO_2R^2$; —($C_1$–$C_6$)alkyl-$CO_2R^2$; —$C(O)N(R^2)_2$; —($C_1$–$C_6$)alkyl-$C(O)N(R^2)_2$; $R^2ON=$; $R^2ON=$($C_1$–$C_6$)alkyl-; $R^2ON=CR^2$($C_1$–$C_6$)alkyl-; —$NR^2(OR^2)$; —($C_1$–$C_6$)alkyl-$NR^2(OR^2)$; —$C(O)(NR^2R^2)$; —($C_1$–$C_6$)alkyl-$C(O)(NR^2OR^2)$; —$S(O)_mR^2$; wherein each $R^2$ is independently selected from hydrogen, ($C_1$–$C_6$)alkyl, aryl, or aryl($C_1$–$C_6$)alkyl-; $R^3C(O)O$—, wherein $R^3$ is ($C_1$–$C_6$)alkyl, aryl, or aryl($C_1$–$C_6$)alkyl-; $R^3C(O)O$—($C_1$–$C_6$)alkyl-; $R^4R^5N$—$C(O)$—$O$—; $R^4R^5NS(O)_2$—; $R^4R^5NS(O)_2$($C_1$–$C_6$)alkyl-; $R^4S(O)_2R^5N$—; $R^4S(O)_2R^5N$($C_1$–$C_6$)alkyl-; wherein m is 0, 1 or 2, and $R^4$ and $R^5$ are each independently selected from hydrogen or ($C_1$–$C_6$)alkyl; —$C(=NR^6)(N(R^4)_2)$; or —($C_1$–$C_6$)alkyl-$C(=NR^6)(N(R^4)_2)$ wherein $R^6$ represents $OR^2$ or $R^2$ wherein $R^2$ is defined as above;

with the proviso that the cycloalkenyl ring is not aromatic;

with the proviso that $R^1$ must be substituted by at least one of $R^3C(O)O$—, $R^3C(O)O$—($C_1$–$C_6$)alkyl-, $R^2ON=$, $R^2ON=$($C_1$–$C_6$)alkyl-, $R^2ON=CR^2$($C_1$–$C_6$)alkyl-, —$NR^2(OR^2)$, $R^4R^5NS(O)_2$—, $R^4R^5NS(O)_2$($C_1$–$C_6$) alkyl-, $R^4S(O)_2R^5N$—, or $R^4S(O)_2R^5N$($C_1$–$C_6$)alkyl-;

with the proviso that when $R^1$ is only substituted by one of $R^2ON=$, then $R^2$ cannot be hydrogen.

Where $R^1$ is a cyclohexyl or cyclohexenyl ring, the ring is preferably substituted at the 3- or 4-position, and more preferably at the 4-position.

Where $R^1$ is a cyclopentyl or cyclopentenyl ring, the ring is preferably substituted at the 3-position.

In a preferred embodiment, $R^1$ is monosubstituted.

In a further preferred embodiment, $R^1$ is disubstituted.

In a preferred embodiment, $R^1$ is substituted by at least one of $R^3C(O)O$— or $R^3C(O)O$—($C_1$–$C_6$)alkyl-.

In a further preferred embodiment, $R^1$ is substituted by at least one of $R^3C(O)O$—.

In a further preferred embodiment, $R^1$ is substituted by at least one of $R^3C(O)O$—($C_1$–$C_6$)alkyl-.

In a further preferred embodiment, $R^1$ is substituted by at least one of $R^2ON=$, $R^2ON=$($C_1$–$C_6$)alkyl-, or $R^2ON=CR^2$($C_1$–$C_6$)alkyl-; with the proviso that when $R^1$ is only substituted by one of $R^2ON=$, then $R^2$ cannot be hydrogen.

In a further preferred embodiment, $R^1$ is substituted by at least one of $R^2ON=$, with the proviso that when $R^1$ is only substituted by one of $R^2ON=$, then $R^2$ cannot be hydrogen.

In a further preferred embodiment, $R^1$ is substituted by at least one of —$NR^2(OR^2)$.

In a further preferred embodiment, $R^1$ is substituted by at least one of $R^4R^5NS(O)_2$—, $R^4R^5NS(O)_2$($C_1$–$C_6$)alkyl-, $R^4S(O)_2R^5N$—, or $R^4S(O)_2R^5N$($C_1$–$C_6$)alkyl-.

In a further preferred embodiment, $R^1$ is substituted by at least one of $R^4S(O)_2R^5N$—.

In a further preferred embodiment, $R^1$ is substituted by at least one of $R4S(O)_2R^5N$($C_1$–$C_6$)alkyl-.

In a further preferred embodiment, $R^1$ is a ($C_3$–$C_8$) cycloalkyl ring or ($C_5$–$C_8$)cycloalkenyl ring, wherein either the cycloalkyl ring or cycloalkenyl ring is substituted by one of $R^3C(O)O$—, $R^3C(O)O$—($C_1$–$C_6$)alkyl-, $R^2ON=$, $R^2ON=$($C_1$–$C_6$)alkyl-, $R^2ON=CR^2$($C_1$–$C_6$)alkyl-, —$NR^2(OR^2)$, $R^4R^5NS(O)_2$—, $R^4R^5NS(O)_2$($C_1$–$C_6$)alkyl-, $R^4S(O)_2R^5N$—, or $R^4S(O)_2R^5N$($C_1$–$C_6$)alkyl-; wherein $R^2$, $R^3$, $R^4$ and $R^5$ are as defined above;

with the proviso that the cycloalkenyl ring is not aromatic;

and with the proviso that when $R^1$ is substituted by $R^2ON=$, then $R^2$ cannot be hydrogen.

In a further preferred embodiment, $R^1$ is a ($C_3$–$C_8$) cycloalkyl ring or ($C_5$–$C_8$)cycloalkenyl ring, wherein either the cycloalkyl ring or cycloalkenyl ring is substituted by one of $R^3C(O)O$—, $R^3C(O)O$—($C_1$–$C_6$)alkyl-, $R^2ON=$, or $R^4S(O)_2R^5N$—; wherein $R^2$, $R^3$, $R^4$ and $R^5$ are as defined above;

with the proviso that the cycloalkenyl ring is not aromatic;

and with the proviso that when $R^1$ is substituted by $R^2ON=$, then $R^2$ cannot be hydrogen.

In a further preferred embodiment, $R^1$ is substituted by $R^3C(O)O$— or $R^3C(O)O$—($C_1$–$C_6$)alkyl-.

In a further preferred embodiment, $R^1$ is substituted by $R^3C(O)O$—.

In a further preferred embodiment, $R^1$ is substituted by $R^3C(O)O$—($C_1$–$C_6$)alkyl-.

In a further preferred embodiment, $R^1$ is substituted by $R^2ON=$, $R^2ON=$($C_1$–$C_6$)alkyl-, or $R^2ON=CR^2$($C_1$–$C_6$) alkyl-, with the proviso that when $R^1$ is substituted by $R^2ON=$, then $R^2$ cannot be hydrogen.

In a further preferred embodiment, $R^1$ is substituted by $R^2ON=$, where $R^2$ cannot be hydrogen.

In a further preferred embodiment, $R^1$ is substituted by —$NR^2(OR^2)$.

In a further preferred embodiment, $R^1$ is substituted by $R^4R^5NS(O)_2$—, $R^4R^5NS(O)_2$($C_1$–$C_6$)alkyl-, $R^4S(O)_2R^5N$— or $R^4S(O)_2R^5N$($C_1$–$C_6$)alkyl-.

In a further preferred embodiment, $R^1$ is substituted by $R^4S(O)_2R^5N$—.

In a further preferred embodiment, $R^1$ is substituted by $R^4S(O)_2R^5N$($C_1$–$C_6$) alkyl-.

The ($C_2$–$C_9$)heterocycloalkyl substituent, when present on $R^1$, is preferably a group of the formula:

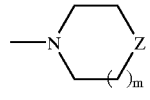

wherein m is as defined above, and

Z is $CH_2$, $NR^2$, OS, SO, or $SO_2$.

For any of the aforementioned compounds of the present invention, $R^1$ is preferably a group of the formula:

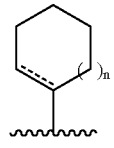

which is substituted as described above for $R^1$;

wherein n is 0, 1, or 2;

wherein the dashed line indicates an optional double bond at that position.

In a preferred embodiment, n is 0 or 1.

In a further preferred embodiment, n is 0; and the dashed line represents a double bond at that position.

In a further preferred embodiment, n is 1.

In a further preferred embodiment, $R^1$ is substituted by =O, =NOH, CH$_2$OH,

or a combination thereof.

In a further preferred embodiment, n is 0; $R^1$ is substituted by =NOH; and the dashed line represents a double bond at that position.

In further preferred embodiment, n is 1; and $R^1$ is substituted by =O, =NOH, CH$_2$OH, or

or a combination thereof.

The invention further provides a compound selected from the group consisting of:

O-Benzyl-4-(2,4-dihydroxyphenyl)cyclohexanone oxime;

(±)-N-[3-(2,4-Dihydroxyphenyl)cyclohexyl]methanesulfonamide;

(±)-O-Methyl-3-(2,4-dihydroxyphenyl)cyclohexanone oxime;

(±)-O-Benzyl-3-(2,4-dihydroxyphenyl)cyclohexanone oxime;

and a pharmaceutically acceptable salt thereof.

The invention further provides a compound selected from the group consisting of:

O-Methyl-4-(2,4-dihydroxyphenyl)cyclohexanone oxime;

(±)-4-[3-(Hydroxyamino)cyclohexyl]-1,3-benzenediol;

cis-N-[4-(2,4-Dihydroxyphenyl)cyclohexyl]-1-butanesulfonamide;

trans-N-[4-(2,4-Dihydroxyphenyl)cyclohexyl]methanesulfonamide;

cis-N-[4-(2,4-Dihydroxyphenyl)cyclohexyl]methanesulfonamide;

trans-4-(2,4-Dihydroxyphenyl)cyclohexyl) 4-(dimethylamino)benzoate;

trans-4-(2,4-Dihydroxyphenyl)cyclohexyl 4-tert-butyl benzoate;

trans-4-(2,4-Dihydroxyphenyl)cyclohexyl 4-fluorobenzoate;

trans-4-(2,4-Dihydroxyphenyl)cyclohexyl 4-trifluoromethylbenzoate;

trans-4-(2,4-Dihydroxyphenyl)cyclohexyl 4-methoxybenzoate;

trans-4-(2,4-Dihydroxyphenyl)cyclohexyl 4-methylbenzoate;

trans-4-(2,4-Dihydroxyphenyl)cyclohexyl 4-chlorobenzoate;

trans-4-(2,4-Dihydroxyphenyl)cyclohexyl 3,4-dimethylbenzoate;

trans-4-(2,4-Dihydroxyphenyl)cyclohexyl 3,4-dichlorobenzoate;

[4-(2,4-Dihydroxyphenyl)cyclohexyl]methyl propionate;

cis/trans-4-[4-(hydroxyamino)cyclohexyl]-1,3-benzenediol;

trans-4-[4-(methoxyamino)cyclohexyl]-1,3-benzenediol;

and a pharmaceutically acceptable salt thereof.

The present invention further provides a topical pharmaceutical composition for lightening skin or reducing the pigmentation of skin in a human, comprising a pharmaceutically acceptable carrier, and a skin-lightening or pigmentation-reducing amount of a compound of formula I:

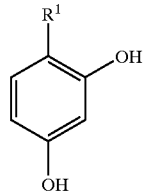

or a pharmaceutically acceptable salt thereof, wherein:

$R^1$ is a (C$_3$–C$_8$)cycloalkyl ring or (C$_5$–C$_8$)cycloalkenyl ring, wherein either the cycloalkyl ring or cycloalkenyl ring is substituted by one to three substituents independently selected from the group consisting of cyano; halo; (C$_1$–C$_6$)alkyl; aryl; (C$_2$–C$_9$)heterocycloalkyl; (C$_2$–C$_9$)heteroaryl; aryl(C$_1$–C$_6$)alkyl-; =O; =CHO (C$_1$–C$_6$)alkyl; amino; hydroxy; (C$_1$–C$_6$)alkoxy; aryl (C$_1$–C$_6$)alkoxy-; (C$_1$–C$_6$)acyl; (C$_1$–C$_6$)alkylamino-; aryl(C$_1$–C$_6$)alkylamino-; amino(C$_1$–C$_6$)alkyl-; (C$_1$–C$_6$)alkoxy-CO—NH—; (C$_1$–C$_6$)alkylamino-CO—; (C$_2$–C$_6$)alkenyl; (C$_2$–C$_6$)alkynyl; hydroxy (C$_1$–C$_6$)alkyl-; (C$_1$–C$_6$)alkoxy(C$_1$–C$_6$)alkyl-; (C$_1$–C$_6$) acyloxy(C$_1$–C$_6$)alkyl-; nitro; cyano(C$_1$–C$_6$)alkyl-; halo (C$_1$–C$_6$)alkyl-; nitro(C$_1$–C$_6$)alkyl-; trifluoromethyl; trifluoromethyl(C$_1$–C$_6$)alkyl-; (C$_1$–C$_6$)acylamino-; (C$_1$–C$_6$)acylamino(C$_1$–C$_6$)alkyl-; (C$_1$–C$_6$)alkoxy (C$_1$–C$_6$)acylamino-; amino(C$_1$–C$_6$)acyl-; amino (C$_1$–C$_6$)acyl(C$_1$–C$_6$)alkyl-; (C$_1$–C$_6$)alkylamino (C$_1$–C$_6$)acyl-; ((C$_1$–C$_6$) alkyl)$_2$amino(C$_1$–C$_6$)acyl-; —CO$_2$R$^2$; —(C$_1$–C$_6$)alkyl-CO$_2$R$^2$; —C(O)N(R$^2$)$_2$; —(C$_1$–C$_6$)alkyl-C(O)N(R$^2$)$_2$; R$^2$ON=; R$^2$ON= (C$_1$–C$_6$)alkyl-; R$^2$ON=CR$^2$(C$_1$–C$_6$)alkyl-; —NR$^2$ (OR$^2$); —(C$_1$–C$_6$)alkyl-NR$^2$(OR$^2$); C(O)(NR$^2$OR$^2$); —(C$_1$–C$_6$)alkyl-C(O)(NR$^2$OR$^2$); —S(O)$_m$R$^2$; wherein each R$^2$ is independently selected from hydrogen, (C$_1$–C$_6$)alkyl, aryl, or aryl(C$_1$–C$_6$)alkyl-; R$^3$C(O)O—, wherein R$^3$ is (C$_1$–C$_6$)alkyl, aryl, or aryl(C$_1$–C$_6$)alkyl-; R$^3$C(O)O—(C$_1$–C$_6$)alkyl-; R$^4$R$^5$N—C(O)—O—; R$^4$R$^5$NS(O)$_2$—; R$^4$R$^5$NS(O)$_2$(C$_1$–C$_6$)alkyl-; R$^4$S(O)$_2$R$^5$N—; R$^4$S(O)$_2$R$^5$N(C$_1$–C$_6$)alkyl-; wherein m is 0, 1 or 2, and R$^4$ and R$^5$ are each independently selected from hydrogen or (C$_1$–C$_6$)alkyl; —C(=NR$^6$)(N(R$^4$)$_2$); or —(C$_1$–C$_6$)alkyl-C(=NR$^6$)(N(R$^4$)$_2$) wherein R$^6$ represents OR$^2$ or R$^2$ wherein R$^2$ is defined as above;

with the proviso that the cycloalkenyl ring is not aromatic;

with the proviso that R$^1$ must be substituted by at least one of R$^3$C(O)O—, R$^3$C(O)O—(C$_1$–C$_6$)alkyl-, R$^2$ON=, R$^2$ON=(C$_1$–C$_6$)alkyl-, R$^2$ON=CR$^2$(C$_1$–C$_6$)alkyl-, —NR$^2$(OR$^2$), R$^4$R$^5$NS(O)$_2$—, R$^4$R$^5$NS(O)$_2$(C$_1$–C$_6$) alkyl-, R$^4$S(O)$_2$R$^5$N—, or R$^4$S(O)$_2$R$^5$N(C$_1$–C$_6$)alkyl-.

Where R$^1$ is a cyclohexyl or cyclohexenyl ring, the ring is preferably substituted at the 3- or 4-position, and more preferably at the 4-position.

Where R$^1$ is a cyclopentyl or cyclopentenyl ring, the ring is preferably substituted at the 3-position.

In a preferred embodiment, $R^1$ is monosubstituted.

In a further preferred embodiment, $R^1$ is disubstituted.

In a preferred embodiment, $R^1$ is substituted by at least one of $R^3C(O)O—$ or $R^3C(O)O—(C_1-C_6)$alkyl-.

In a further preferred embodiment, $R^1$ is substituted by at least one of $R^3C(O)O—$.

In a further preferred embodiment, $R^1$ is substituted by at least one of $R^3C(O)O—(C_1-C_6)$alkyl-.

In a further preferred embodiment, $R^1$ is substituted by at least one of $R^2ON=$, $R^2ON=(C_1-C_6)$alkyl-, or $R^2ON=CR^2(C_1-C_6)$alkyl-.

In a further preferred embodiment, $R^1$ is substituted by at least one of $R^2ON=$.

In a further preferred embodiment, $R^1$ is substituted by at least one of $—NR^2(OR^2)$.

In a further preferred embodiment, $R^1$ is substituted by at least one of $R^4R^5NS(O)_2—$, $R^4R^5NS(O)_2(C_1-C_6)$alkyl-, $R^4S(O)_2R^5N—$, or $R^4S(O)_2R^5N(C_1-C_6)$alkyl-.

In a further preferred embodiment, $R_1$ is substituted by at least one of $R^4S(O)_2R^5N—$.

In a further preferred embodiment, $R_1$ is substituted by at least one of $R^4S(O)_2R^5N(C_1-C_6)$alkyl-.

In a further preferred embodiment, $R^1$ is a $(C_3-C_8)$ cycloalkyl ring or $(C_5-C_8)$cycloalkenyl ring, wherein either the cycloalkyl ring or cycloalkenyl ring is substituted by $R^3C(O)O—$, $R^3C(O)O—(C_1-C_6)$alkyl-, $R^2ON=$, $R^2ON=(C_1-C_6)$alkyl-, $R^2ON=CR^2(C_1-C_6)$alkyl-, $—NR^2(OR^2)$, $R^4R^5NS(O)_2—$, $R^4R^5NS(O)_2(C_1-C_6)$alkyl-, $R^4S(O)_2R^5N—$, or $R^4S(O)_2R^5N(C_1-C_6)$alkyl-; wherein $R^2$, $R^3$, $R^4$ and $R^5$ are as defined above;

with the proviso that the cycloalkenyl ring is not aromatic.

In a further preferred embodiment, $R^1$ is a $(C_3-C_8)$ cycloalkyl ring or $(C_5-C_8)$cycloalkenyl ring, wherein either the cycloalkyl ring or cycloalkenyl ring is substituted by one of $R^3C(O)O—$, $R^3C(O)O—(C_1-C_6)$alkyl-, $R^2ON=$, or $R^4S(O)_2R^5N—$; wherein $R^2$, $R^3$, $R^4$ and $R^5$ are as defined above;

with the proviso that the cycloalkenyl ring is not aromatic.

In a preferred embodiment, $R^1$ is substituted by $R^3C(O)O—$ or $R^3C(O)O—(C_1-C_6)$alkyl-.

In a further preferred embodiment, $R^1$ is substituted by $R^3C(O)O—$.

In a further preferred embodiment, $R^1$ is substituted by $R^3C(O)O—(C_1-C_6)$alkyl-.

In a further preferred embodiment, $R^1$ is substituted by $R^2ON=$, $R^2ON=(C_1-C_6)$alkyl-, or $R^2ON=CR^2(C_1-C_6)$alkyl-.

In a further preferred embodiment, $R^1$ is substituted by $R^2ON=$.

In a further preferred embodiment, $R^1$ is substituted by $—NR^2(OR^2)$.

In a further preferred embodiment, $R^1$ is substituted by $R^4R^5NS(O)_2—$, $R^4R^5NS(O)_2(C_1-C_6)$alkyl-, $R^4S(O)_2R^5N—$, or $R^4S(O)_2R^5N(C_1-C_6)$alkyl-.

In a further preferred embodiment, $R^1$ is substituted by $R^4S(O)_2R^5N—$.

In a further preferred embodiment, $R^1$ is substituted by $R^4S(O)_2R^5N(C_1-C_6)$alkyl-.

The $(C_2-C_9)$heterocycloalkyl substituent, when present on $R^1$ of the compound of formula I, is preferably a group of the formula:

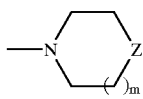

wherein m is as defined above, and

Z is $CH_2$, $NR^2$, O, S, SO, or $SO_2$.

For any of the aforementioned compositions of the present invention, $R^1$ of the compound of formula I is preferably a group of the formula:

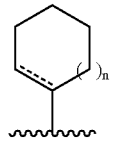

which is substituted as described above for $R^1$;

wherein n is 0, 1, or 2;

wherein the dashed line indicates an optional double bond at that position.

In a further preferred embodiment, n is 0 or 1.

In a further preferred embodiment, n is 0; and the dashed line represents a double bond at that position.

In a further preferred embodiment, n is 1.

In a further preferred embodiment, $R^1$ is substituted by $=O$, $=NOH$, $CH_2OH$ or

or a combination thereof.

In a further preferred embodiment, n is 0; $R^1$ is substituted by $=NOH$; and the dashed line represents a double bond at that position.

In further preferred embodiment, n is 1; and $R^1$ is substituted by $=O$, $=NOH$, $CH_2OH$, or

or a combination thereof.

The present invention further provides a topical pharmaceutical composition for lightening skin or reducing the pigmentation of skin in a human, comprising a pharmaceutically acceptable carrier, and a skin-lightening or pigmentation-reducing effective amount of a compound selected from the group consisting of:

4-(2,4-Dihydroxyphenyl)cyclohexanone oxime;

O-Methyl-4-(2,4-dihydroxyphenyl)cyclohexanone oxime;

O-Benzyl-4-(2,4-dihydroxyphenyl)cyclohexanone oxime;

3-(2,4-Dihydroxyphenyl)-2-cyclohexen-1-one oxime;

(±)-3-(2,4-Dihydroxyphenyl)cyclohexanone oxime;

(±)-N-[3-(2,4-Dihydroxyphenyl)cyclohexyl]methanesulfonamide;

(±)-4-[3-(Hydroxyamino)cyclohexyl]-1,3-benzenediol;

(±)-O-Methyl-3-(2,4-dihydroxyphenyl)cyclohexanone oxime;

(±)-O-Benzyl-3-(2,4-dihydroxyphenyl)cyclohexanone oxime;

3-(2,4-Dihydroxyphenyl)-2-cyclopentenone oxime;

(±)-3-(2,4-Dihydroxyphenyl)cyclopentanone oxime;

and a pharmaceutically acceptable salt thereof.

The present invention further provides a topical pharmaceutical composition for lightening skin or reducing the pigmentation of skin in a human, comprising a pharmaceutically acceptable carrier, and a skin-lightening or pigmentation-reducing effective amount of a compound selected from the group consisting of:

cis-N-[4-(2,4-Dihydroxyphenyl)cyclohexyl]-1-butanesulfonamide;

trans-N-[4-(2,4-Dihydroxyphenyl)cyclohexyl] methanesulfonamide;

cis-N-[4-(2,4-Dihydroxyphenyl)cyclohexyl] methanesulfonamide;

trans-4-(2,4-Dihydroxyphenyl)cyclohexyl) 4-(dimethylamino)benzoate;

trans-4-(2,4-Dihydroxyphenyl)cyclohexyl 4-tert-butylbenzoate;

trans-4-(2,4-Dihydroxyphenyl)cyclohexyl 4-fluorobenzoate;

trans-4-(2,4-Dihydroxyphenyl)cyclohexyl 4-trifluoromethylbenzoate;

trans-4-(2,4-Dihydroxyphenyl)cyclohexyl 4-methoxybenzoate;

trans-4-(2,4-Dihydroxyphenyl)cyclohexyl 4-methylbenzoate;

trans-4-(2,4-Dihydroxyphenyl)cyclohexyl 4-chlorobenzoate;

trans-4-(2,4-Dihydroxyphenyl)cyclohexyl 3,4-dimethylbenzoate;

trans-4-(2,4-Dihydroxyphenyl)cyclohexyl 3,4-dichlorobenzoate;

[4-(2,4-Dihydroxyphenyl)cyclohexyl]methyl propionate;

cis/trans-4-[4-(hydroxyamino)cyclohexyl]-1,3-benzenediol;

trans-4-[4-(methoxyamino)cyclohexyl]-1,3-benzenediol;

and a pharmaceutically acceptable salt thereof.

In a further preferred embodiment, the skin-lightening or pigmentation-reducing effective amount of a compound of formula I of the pharmaceutical composition of the present invention is a tyrosinase-inhibiting effective amount of the compound.

The present invention further provides a topical pharmaceutical composition for inhibiting tyrosinase in a human, comprising a pharmaceutically acceptable carrier, and a tyrosinase-inhibiting effective amount of a compound selected from among the compounds of any of the aforementioned pharmaceutical compositions of the present invention.

The present invention further provides a method of lightening skin or reducing the pigmentation of skin in a human, comprising administering to said human a skin-lightening or skin pigmentation-reducing effective amount of a compound of formula 1:

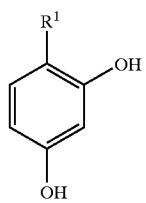

I or a pharmaceutically acceptable salt thereof, wherein:

$R^1$ is a $(C_3–C_8)$cycloalkyl ring or $(C_5–C_8)$cycloalkenyl ring, wherein either the cycloalkyl ring or cycloalkenyl ring is substituted by one to three substituents independently selected from the group consisting of cyano;

halo; $(C_1–C_6)$alkyl; aryl; $(C_2–C_9)$heterocycloalkyl; $(C_2–C_9)$heteroaryl; aryl$(C_1–C_6)$alkyl-; $=O$; $=CHO$ $(C_1–C_6)$alkyl; amino; hydroxy; $(C_1–C_6)$alkoxy; aryl $(C_1–C_6)$alkoxy-; $(C_1–C_6)$acyl; $(C_1–C_6)$alkylamino-; aryl$(C_1–C_6)$alkylamino-; amino$(C_1–C_6)$alkyl-; $(C_1–C_6)$alkoxy-CO—NH—; $(C_1–C_6)$alkylamino-CO—; $(C_2–C_6)$alkenyl; $(C_2–C_6)$alkynyl; hydroxy $(C_1–C_6)$alkyl-; $(C_1–C_6)$alkoxy$(C_1–C_6)$alkyl-; $(C_1–C_6)$acyloxy$(C_1–C_6)$alkyl-; nitro; cyano$(C_1–C_6)$alkyl-; halo $(C_1–C_6)$alkyl-; nitro$(C_1–C_6)$alkyl-; trifluoromethyl; trifluoromethyl$(C_1–C_6)$alkyl-; $(C_1–C_6)$acylamino-; $(C_1–C_6)$acylamino$(C_1–C_6)$alkyl-; $(C_1–C_6)$alkoxy $(C_1–C_6)$acylamino-; amino$(C_1–C_6)$acyl-; amino $(C_1–C_6)$acyl$(C_1–C_6)$alkyl-; $(C_1–C_6)$alkylamino $(C_1–C_6)$acyl-; $((C_1–C_6)$ alkyl$)_2$amino$(C_1–C_6)$acyl-; $—CO_2R^2$; $—(C_1–C_6)$alkyl-$CO_2R^2$; $—C(O)N(R^2)_2$; $—(C_1–C_6)$alkyl-$C(O)N(R^2)_2$; $R^2ON=$; $R^2ON=$ $(C_1–C_6)$alkyl-; $R^2ON=CR^2(C_1–C_6)$alkyl-; $—NR^2$ $(OR^2)$; $—(C_1–C_6)$alkyl-$NR^2(OR^2)$; $—C(O)(NR^2OR^2)$; $—(C_1–C_6)$alkyl-$C(O)(NR^2OR^2)$; $—S(O)_mR^2$; wherein each R2 is independently selected from hydrogen, $(C_1–C_6)$alkyl, aryl, or aryl$(C_1–C_6)$alkyl-; $R^3C(O)O—$, wherein $R^3$ is $(C_1–C_6)$alkyl, aryl, or aryl$(C_1–C_6)$alkyl-; $R^3C(O)O—(C_1–C_6)$alkyl-; $R^4R^5N—C(O)—O—$; $R^4R^5NS(O)_2—$; $R^4R^5NS(O)_2(C_1–C_6)$alkyl-; $R^4S(O)_2 R^5N—$; $R^4S(O)_2R^5N(C_1–C_6)$alkyl-; wherein m is 0, 1 or 2, and $R^4$ and $R^5$ are each independently selected from hydrogen or $(C_1–C_6)$alkyl; $—C(=NR^6)(N(R^4)_2)$; or $—(C_1–C_6)$alkyl-$C(=NR^6)(N(R^4)_2)$ wherein $R^6$ represents $OR^2$ or $R^2$ wherein $R^2$ is defined as above;

with the proviso that the cycloalkenyl ring is not aromatic;

with the proviso that when $R^1$ is a $(C_5–C_8)$cycloalkyl ring, or when $R^1$ is a $(C_5–C_8)$cycloalkenyl ring having the following structure:

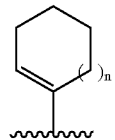

wherein n is 0, 1, 2 or 3, where such $(C_5–C_8)$cycloalkyl ring or $(C_5–C_8)$cycloalkenyl ring is substituted by hydroxy, $(C_1–C_6)$alkoxy-, aryl$(C_1–C_6)$alkoxy-, $—OC(O)(C_1–C_6)$ alkyl, $—OC(O)$aryl$(C_1–C_6)$alkyl, $—OC(O)$phenyl, halo, $(C_1–C_6)$alkyl-, aryl$(C_1–C_6)$alkyl-, $—SH$, $—S(C_1–C_6)$alkyl, aryl$(C_1–C_6)$alkyl-S—, $—NH_2$, $—NH(C_1–C_6)$alkyl, or aryl $(C_1–C_6)$alkyl-HN—; then the $(C_5–C_8)$cycloalkyl ring or the $(C_5–C_8)$cycloalkenyl ring must be di- or tri-substituted.

Where $R^1$ is a cyclohexyl or cyclohexenyl ring, the ring is preferably substituted at the 3- or 4-position, and more preferably at the 4-position.

Where $R^1$ is a cyclopentyl or cyclopentenyl ring, the ring is preferably substituted at the 3-position.

In a preferred embodiment, $R^1$ is monosubstituted.

In a further preferred embodiment, $R^1$ is disubstituted.

In a preferred embodiment, $R^1$ of the compound of the method is substituted by at least one of $R^3C(O)O—$, $R^3C(O)O—(C_1–C_6)$alkyl-, $R^2ON=$, $R^2ON=(C_1–C_6)$alkyl-, $R^2ON=CR^2(C_1–C_6)$alkyl-, $—NR^2(OR^2)$, $R^4R^5NS(O)_2—$, $R^4R^5NS(O)_2(C_1–C_6)$alkyl-, $R^4S(O)_2R^5N—$, or $R^4S(O)_2 R^5N(C_1–C_6)$alkyl-.

In a further preferred embodiment, $R^1$ of the compound of the method is substituted by at least one of $R^3C(O)O—$ or $R^3C(O)O—(C_1–C_6)$alkyl-.

In a further preferred embodiment, $R^1$ is substituted by at least one of $R^3C(O)O-$.

In a further preferred embodiment, $R^1$ is substituted by at least one of $R^3C(O)O-(C_1-C_6)$alkyl-.

In a further preferred embodiment, $R^1$ of the compound of the method is substituted by at least one of $R^2ON=$, $R^2ON=(C_1-C_6)$alkyl-, or $R^2ON=CR^2(C-C_6)$alkyl-.

In a further preferred embodiment, $R^1$ of the compound of the method is substituted by at least one of $R^2ON=$.

In a further preferred embodiment, $R^1$ of the compound of the method is substituted by at least one of $-NR^2(OR^2)$.

In a further preferred embodiment, $R^1$ of the compound of the method is substituted by at least one of $R^4R^5NS(O)_2-$, $R^4R^5NS(O)_2(C_1-C_6)$alkyl-, $R^4S(O)_2R^5N-$, or $R^4S(O)_2R^5N(C_1-C_6)$alkyl-.

In a further preferred embodiment, $R^1$ of the compound of the method is substituted by at least one of $R^4S(O)_2R^5N-$.

In a further preferred embodiment, $R^1$ of the compound of the method is substituted by at least one of $R^4S(O)_2R^5N(C_1-C_6)$alkyl-.

In a further preferred embodiment, $R^1$ of the compound of the method is substituted by at least one of hydroxy$(C_1-C_6)$alkyl-.

In a further preferred embodiment, $R^1$ is a $(C_3-C_8)$cycloalkyl ring or $(C_5-C_8)$cycloalkenyl ring, wherein either the cycloalkyl ring or cycloalkenyl ring is substituted by one of $R^3C(O)O-$, $R^3C(O)O-(C_1-C_6)$alkyl-, $R^2ON=$, $R^2ON=(C_1-C_6)$alkyl-, $R^2ON=CR^2(C_1-C_6)$alkyl-, $-NR^2(OR^2)$, $R^4R^5NS(O)_2-$, $R^4R^5NS(O)_2(C_1-C_6)$alkyl-, $R^4S(O)_2R^5N-$, or $R^4S(O)_2R^5N(C_1-C_6)$alkyl-; wherein $R^2$, $R^3$, $R^4$ and $R^5$ are as defined above.

In a further preferred embodiment, $R^1$ is a $(C_3-C_8)$cycloalkyl ring or $(C_5-C_8)$cycloalkenyl ring, wherein either the cycloalkyl ring or cycloalkenyl ring is substituted by one of $R^3C(O)O-$, $R^3C(O)O-(C_1-C_6)$alkyl-, $R^2ON=$, or $R^4S(O)_2R^5N-$; wherein $R^2$, $R^3$, $R^4$ and $R^5$ are as defined above.

In a preferred embodiment, $R^1$ is substituted by one of $R^3C(O)O-$ or $R^3C(O)O-(C_1-C_6)$alkyl-.

In a further preferred embodiment, $R^1$ is substituted by one of $R^3C(O)O-$.

In a further preferred embodiment, $R_1$ is substituted by one of $R^3C(O)O-(C_1-C_6)$alkyl-.

In a further preferred embodiment, $R^1$ is substituted by one of $R^2ON=$, $R^2ON=(C_1-C_6)$alkyl-, or $R^2ON=CR^2(C_1-C_6)$alkyl-.

In a further preferred embodiment, $R^1$ is substituted by one of $R^2ON=$.

In a further preferred embodiment, $R^1$ is substituted by one of $-NR^2(OR^2)$.

In a further preferred embodiment, $R^1$ is substituted by one of $R^4R^5NS(O)_2-$, $R^4R^5NS(O)_2(C_1-C_6)$alkyl-, $R^4S(O)_2R^5N-$, or $R^4S(O)_2R^5N(C_1-C_6)$alkyl-.

In a further preferred embodiment, $R^1$ is substituted by one of $R^4S(O)_2R^5N-$.

In a further preferred embodiment, $R^1$ is substituted by one of $R^4S(O)_2R^5N(C_1-C_6)$alkyl-.

In a further preferred embodiment, $R^1$ of the compound of the method is substituted by one of hydroxy$(C_1-C_6)$alkyl-.

The $(C_2-C_9)$heterocycloalkyl substituent, when present on $R^1$ of the compound of formula 1, is preferably a group of the formula:

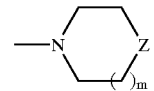

wherein m is as defined above, and

Z is $CH_2$, $NR^2$, O, S, SO, or $SO_2$.

For any of the aforementioned methods of the present invention, $R^1$ of the compound of formula I is preferably a group of the formula:

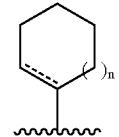

which is substituted as described above for $R^1$;

wherein n is 0, 1, or 2;

wherein the dashed line indicates an optional double bond at that position.

In a further preferred embodiment, n is 0 or 1.

In a further preferred embodiment, n is 0; and the dashed line represents a double bond at that position.

In a further preferred embodiment, n is 1.

In a further preferred embodiment, $R^1$ is substituted by =O, =NOH, $CH_2OH$ or

or a combination thereof.

In a further preferred embodiment, n is 0; $R^1$ is substituted by =NOH; and the dashed line represents a double bond at that position.

In further preferred embodiment, n is 1; and $R^1$ is substituted by =O, =NOH, $CH_2OH$, or

or a combination thereof.

In a preferred embodiment, the method of the present invention comprises administering to a human a skin-lightening or pigmentation-reducing effective amount of a compound selected from the group consisting of:

4-(2,4-Dihydroxyphenyl)cyclohexanone;

4-(2,4-Dihydroxyphenyl)cyclohexanone oxime;

O-Methyl-4-(2,4-dihydroxyphenyl)cyclohexanone oxime;

O-Benzyl-4-(2,4-dihydroxyphenyl)cyclohexanone oxime;

3-(2,4-dihydroxyphenyl)-2-cyclohexen-1-one;

(±)-3-(2,4-Dihydroxyphenyl)cyclohexanone;

3-(2,4-Dihydroxyphenyl)-2-cyclohexen-1-one oxime;

(±)-3-(2,4-Dihydroxyphenyl)cyclohexanone oxime;

(±)-4-[3-(1-Piperazinyl)cyclohexyl]-1,3-benzenediol;

(±)-N-[3-(2,4-Dihydroxyphenyl)cyclohexyl]methanesulfonamide;

(±)-4-[3-(Hydroxymethyl)cyclohexyl]-1,3-benzenediol;

(±)-4-[3-(Hydroxyamino)cyclohexyl]-1,3-benzenediol;
cis/trans-4-[4-(Hydroxymethyl)cyclohexyl]-1,3-benzenediol;
cis/trans-4-(4-Hydroxy-4-methylcyclohexyl)-1,3-benzenediol;
(±)-O-Methyl-3-(2,4-dihydroxyphenyl)cyclohexanone oxime;
(±)-3-(2,4-Dihydroxyphenyl)-1-methylcyclohexanol;
(±)-O-Benzyl-3-(2,4-dihydroxyphenyl)cyclohexanone oxime;
3-(2,4-Dihydroxyphenyl)-2-cyclopentenone oxime;
(±)-3-(2,4-Dihydroxyphenyl)cyclopentanone;
(±)-3-(2,4-Dihydroxyphenyl)cyclopentanone oxime;
and a pharmaceutically acceptable salt thereof.

In a further preferred embodiment, the method of the present invention comprises administering to a human a skin-lightening or pigmentation-reducing effective amount of a compound selected from the group consisting of:
4-(2,4-Dihydroxyphenyl)-3-cyclohexen-1-one;
cis/trans-N-[4-(2,4-Dihydroxyphenyl)cyclohexyl] acetamide;
cis-N-[4-(2,4-Dihydroxyphenyl)cyclohexyl]-1-butanesulfonamide;
trans-N-[4-(2,4-Dihydroxyphenyl)cyclohexyl] methanesulfonamide;
cis-N-[4-(2,4-Dihydroxyphenyl)cyclohexyl] methanesulfonamide;
4-[4-(4-Hydroxyphenyl)cyclohexyl]-1,3-benzenediol;
cis/trans-Methyl [4-(2,4-dihydroxyphenyl)cyclohexyl] acetate;
trans-Methyl [4-(2,4-dihydroxyphenyl)cyclohexyl] acetate;
cis-Methyl [4-(2,4-dihydroxyphenyl)cyclohexyl]acetate;
trans-[4-(2,4-Dihydroxyphenyl)cyclohexyl]acetic acid;
cis-[4-(2,4-Dihydroxyphenyl)cyclohexyl]acetic acid;
cis/trans-[4-(2,4-Dihydroxyphenyl)cyclohexyl]acetic acid;
cis/trans-[4-(2,4-Dihydroxyphenyl)cyclohexyl] acetonitrile;
cis/trans-4-[4-(2-Aminoethyl)cyclohexyl]-1,3-benzenediol;
(±)-4-(3,3-Difluorocyclohexyl)-1,3-benzenediol;
(±)-3-(2,4-Dihydroxyphenyl)cyclohexanecarboxamide;
(±)-3-(2,4-Dihydroxyphenyl)-N-hydroxycyclohexanecarboxamide;
(±)-3-(2,4-Dihydroxyphenyl)-N-ethylcyclohexanecarboxamide;
(±)-4-[3-Hydroxy-3-(hydroxymethyl)cyclohexyl]-1,3-benzenediol;
(±)-N-[3-(2,4-dihydroxyphenyl)cyclohexyl]acetamide;
trans-4-(2,4-Dihydroxyphenyl)cyclohexyl) 4-(dimethylamino)benzoate;
cis/trans-4-(2,4-Dihydroxyphenyl) cyclohexanecarboxylic acid;
trans-4-(2,4-Dihydroxyphenyl)cyclohexyl ethylcarbamate;
trans-4-(2,4-Dihydroxyphenyl)cyclohexyl cyclohexylcarbamate;
trans-4-(2,4-Dihydroxyphenyl)cyclohexyl 4-tert-butylbenzoate;
trans-4-(2,4-Dihydroxyphenyl)cyclohexyl 4-fluorobenzoate;
trans-4-(2,4-Dihydroxyphenyl)cyclohexyl 4-trifluoromethylbenzoate;
trans-4-(2,4-Dihydroxyphenyl)cyclohexyl 4-methoxybenzoate;
trans-4-(2,4-Dihydroxyphenyl)cyclohexyl 4-methylbenzoate;
trans-4-(2,4-Dihydroxyphenyl)cyclohexyl 4-chlorobenzoate;
trans-4-(2,4-Dihydroxyphenyl)cyclohexyl 3,4-dimethylbenzoate;
trans-4-(2,4-Dihydroxyphenyl)cyclohexyl 3,4-dichlorobenzoate;
trans-4-[4-(Phenylsulfanyl)cyclohexyl]-1,3-benzenediol;
trans-4-[4-(Phenylsulfonyl)cyclohexyl]-1,3-benzenediol;
[4-(2,4-Dihydroxyphenyl)cyclohexyl]methyl propionate;
ethyl 4-(2,4-dihydroxyphenyl)-1-hydroxycyclohexane carboxylate;
cis/trans-4-[4-(hydroxyamino)cyclohexyl]-1,3-benzenediol;
trans-4-[4-(methoxyamino)cyclohexyl]-1,3-benzenediol;
and a pharmaceutically acceptable salt thereof.

In a preferred embodiment, the method is carried out by administering a skin-lightening or pigmentation-reducing effective amount of a compound of the present invention to a human in need of said treatment.

In another preferred embodiment, the skin-lightening or pigmentation-reducing effective amount of a compound of the method of the present invention is a tyrosinase-inhibiting effective amount of the compound.

The present invention further provides a method of inhibiting tyrosinase in a human, comprising administering to said human a tyrosinase-inhibiting effective amount of a compound selected from among the compounds used in any of the aforementioned methods of the present invention. In a preferred embodiment, the method is carried out by administering a tyrosinase-inhibiting effective amount of a compound of the present invention to a human in need of said treatment.

The present invention further provides a topical or transdermal pharmaceutical composition for the treatment of an inflammatory disorder such as psoriasis, dermatitis or acne, or for the treatment of dandruff, in a human, comprising a pharmaceutically acceptable carrier, and an amount of a compound of formula I, or a pharmaceutically acceptable salt thereof, used in any of the aforementioned pharmaceutical compositions of the present invention, which amount is effective in treating such disorder or condition.

The present invention further provides a method of treating inflammatory disorders, such as psoriasis, dermatitis or acne, or a method of treating dandruff, in a human, comprising administering to said human an amount of a compound of formula I or a pharmaceutically acceptable salt thereof, used in any of the aforementioned methods of the present invention, which amount is effective in treating such disorder or condition.

The present invention further provides a use of any of the compounds used in any of the aforementioned methods of the present invention, or any of the compounds used in any of the aforementioned pharmaceutical compositions of the present invention, to prepare a medicament useful in lightening skin or reducing pigmentation of skin in a human.

The term "alkyl", as used herein, unless otherwise indicated, includes saturated monovalent hydrocarbon radicals having straight, branched or cyclic moieties or combinations thereof. Any substituents or functional groups on the alkyl group, as indicated herein, can be substituted anywhere on the alkyl group.

The term "aryl", as used herein, refers to phenyl or naphthyl optionally substituted with one or more substituents, preferably from zero to two substituents, independently selected from halogen, OH, $(C_1–C_6)$alkyl, $(C_1–C_6)$ alkoxy, amino, $(C_1–C_6)$alkylamino, di-$((C_1–C_6)$alkyl))amino, nitro, cyano and trifluoromethyl. Any substituents or functional groups on the aryl group, as indicated herein, can be substituted anywhere on the aryl group.

The term "one or more substituents", as used herein, refers to a number of substituents that equals from one to the maximum number of substituents possible based on the number of available bonding sites.

The "halo", as used herein, refers to halogen and, unless otherwise indicated, includes chloro, fluoro, bromo and iodo.

The term "acyl", as used herein, unless otherwise indicated, includes a radical of the general formula RCO wherein R is alkyl, alkoxy, aryl, arylalkyl, or arylalkyloxy and the terms "alkyl" or "aryl" are as defined above.

The term "acyloxy", as used herein, includes O-acyl groups wherein "acyl" is as defined above.

$(C_2–C_9)$Heterocycloalkyl, when used herein, refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2–C_9)$heterocycloalkyl ring can be through a carbon atom or through a nitrogen heteroatom where possible.

$(C_2–C_9)$Heteroaryl, when used herein, refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, etc. One of ordinary skill in the art will understand that the connection of said $(C_2–C_9)$ heterocycloalkyl rings can be through a carbon atom or through a nitrogen heteroatom where possible.

Compounds of formula I may contain chiral centers and therefore may exist in different enantiomeric and diastereomeric forms. This invention relates to all optical isomers, stereoisomers and tautomers of the compounds of formula I, and mixtures thereof, and to all pharmaceutical compositions and methods of treatment defined above that contain or employ them, respectively.

Formula I, as defined above, also includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

The present invention also relates to the pharmaceutically acceptable acid addition and base salts of any of the aforementioned compounds of formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1-methylene-bis-(2-hydroxy-3-naphthoate)) salts.

As used herein, a "skin-lightening or pigmentation reducing amount of a compound of formula I", and the like, means an amount or concentration of the compound capable of detectably lightening skin or reducing pigmentation in a human, as determined by any standard assay. The active compound is typically administered in a pharmaceutical composition and for a standard course of treatment that produces the desired result of skin depigmentation.

As used herein, a "tyrosinase-inhibiting effective amount of a compound of formula I", and the like, means an amount or concentration of the compound capable of detectably inhibiting tyrosinase activity in a human, as determined by any standard assay, such as those described below.

As used herein, an "amount of a compound of formula I capable of treating an inflammatory disorder such as psoriasis, dermatitis or acne, or treating dandruff", and the like, means an amount or concentration of the compound capable of detectably ameliorating, reducing, eliminating, slowing, or preventing the progression of, any symptom or condition associated with or caused by such disorder or condition, in a human, as determined by any standard assay.

DETAILED DESCRIPTION OF THE INVENTION

The compounds of formula I may be prepared as described in the following reaction schemes and discussion. Unless otherwise indicated, n, m, $R^2$, $R^3$, $R^4$, $R^5$, Z, and structural formula I in the reaction schemes and discussion that follow are as defined above.

Scheme 1

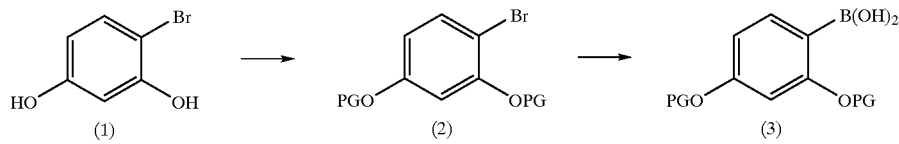

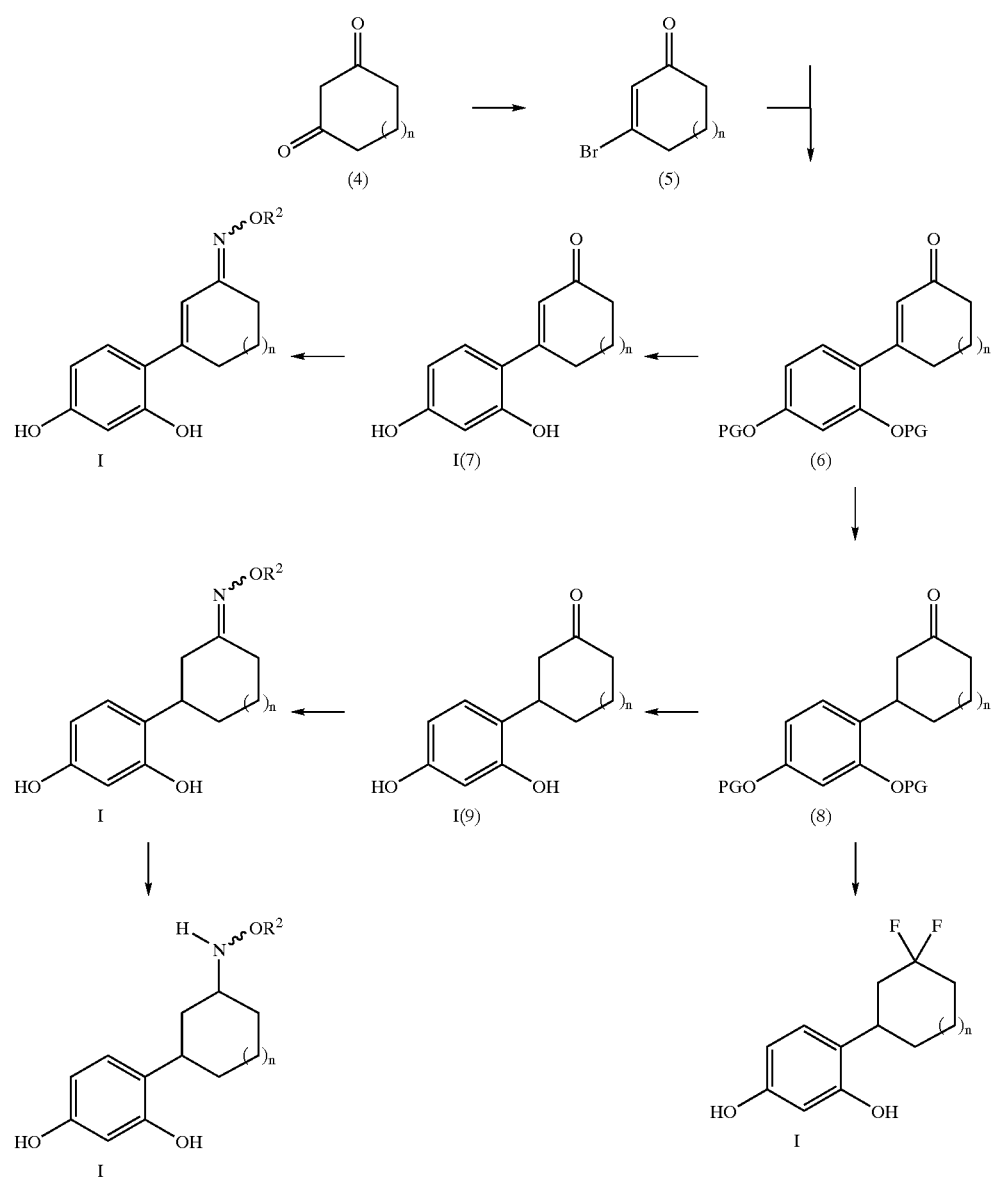
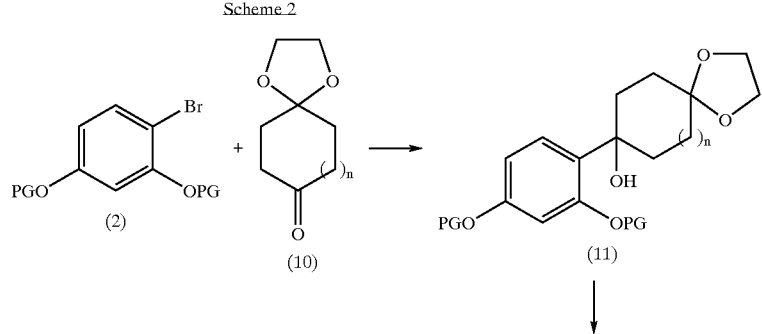
Scheme 2

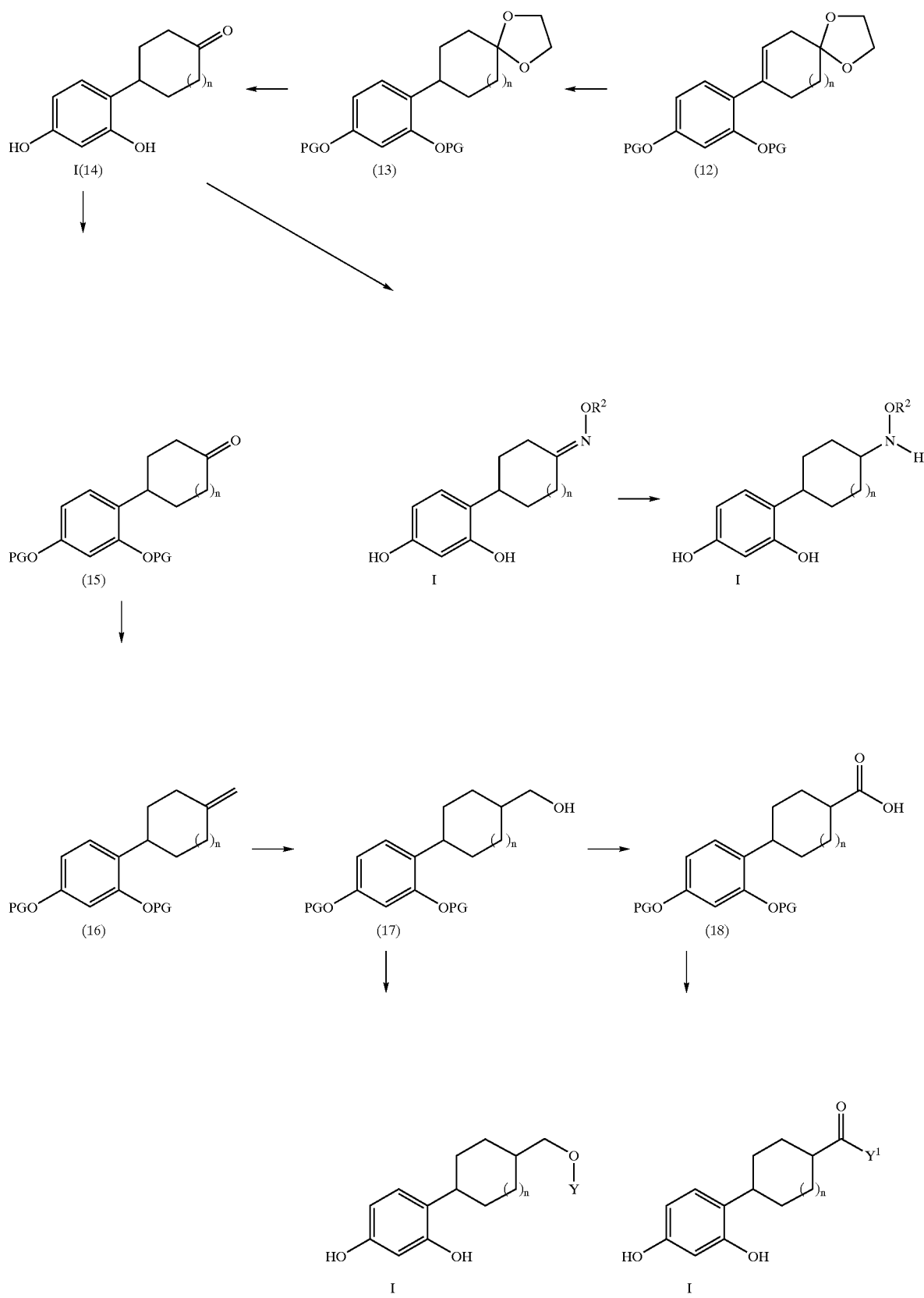

Scheme 3
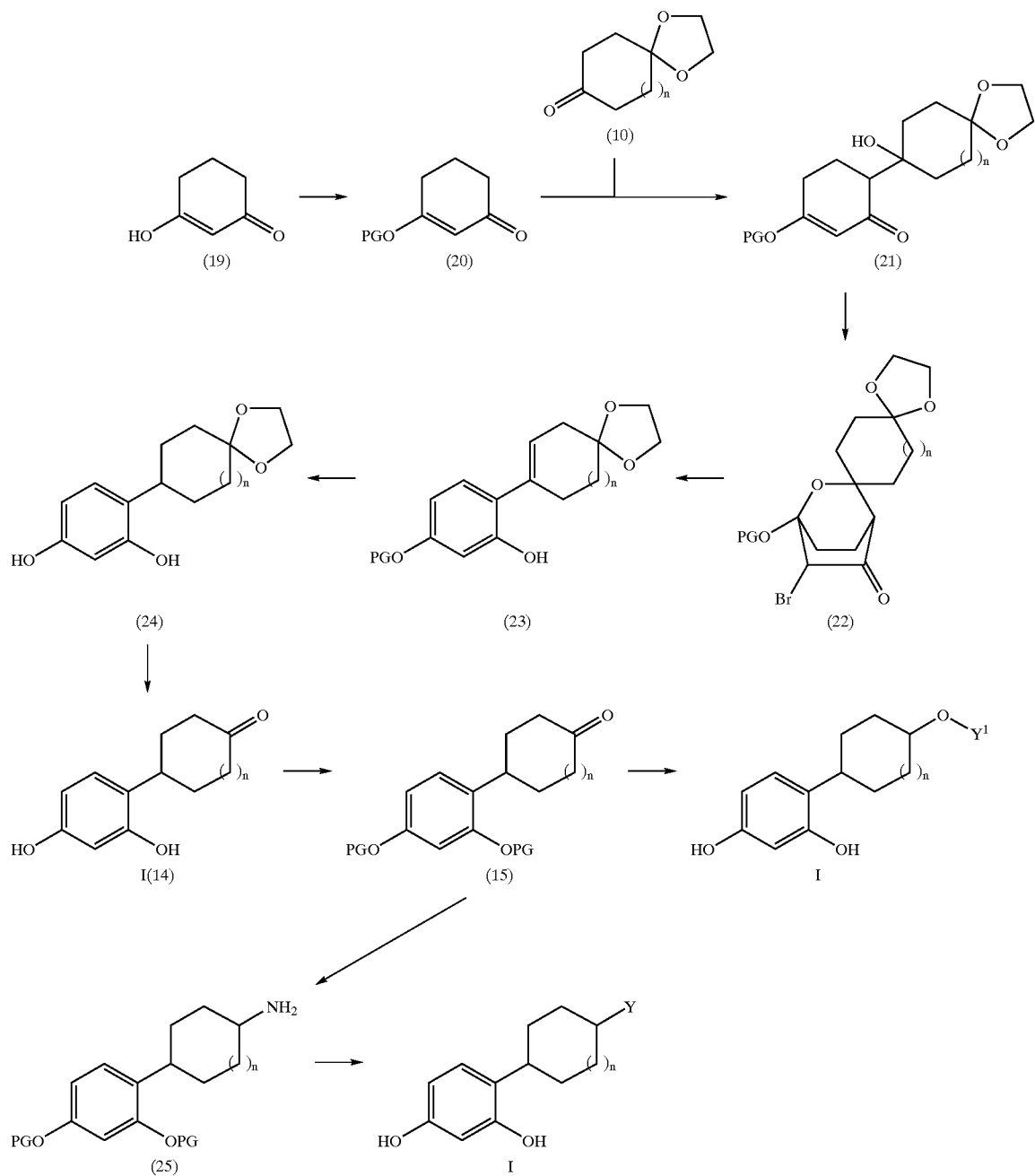
Scheme 4
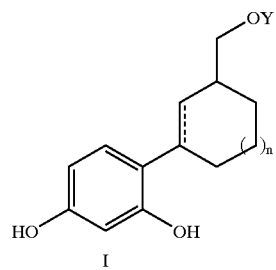

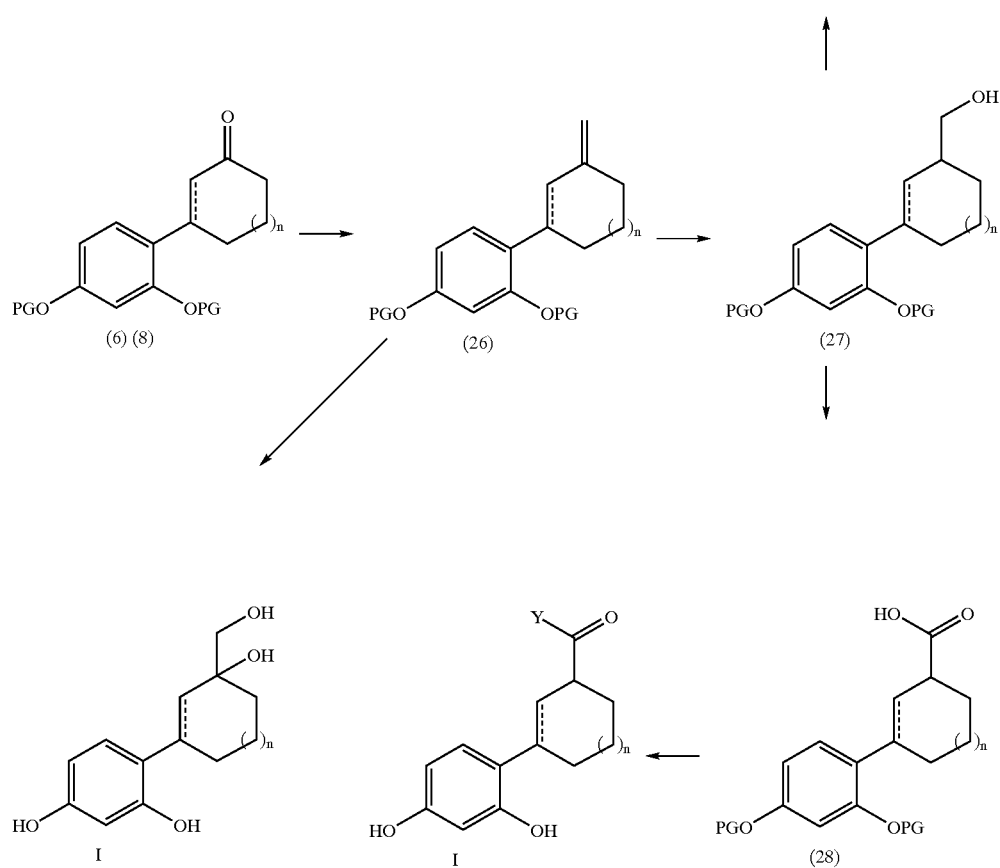
Scheme 5
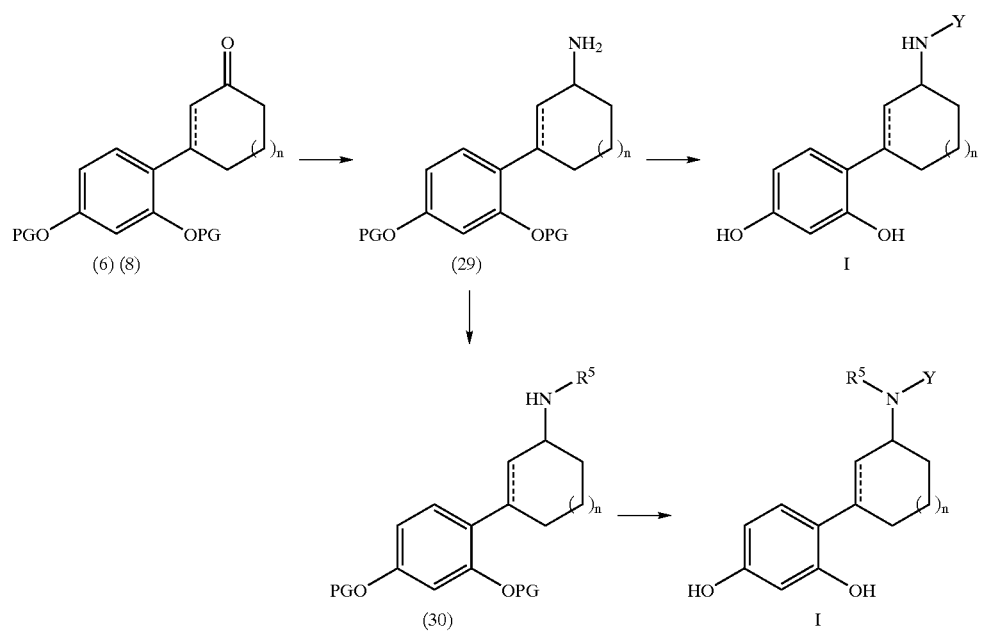

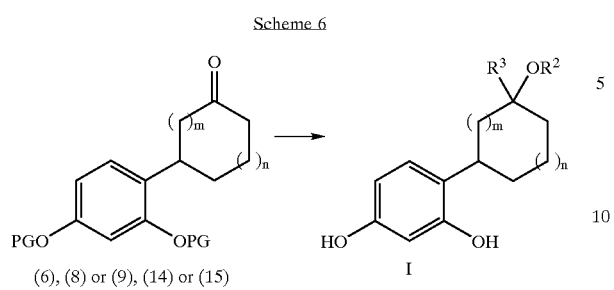
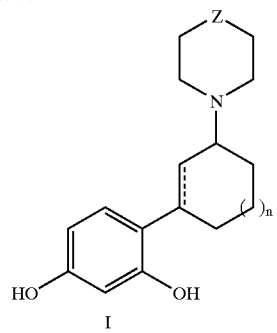

Scheme 10
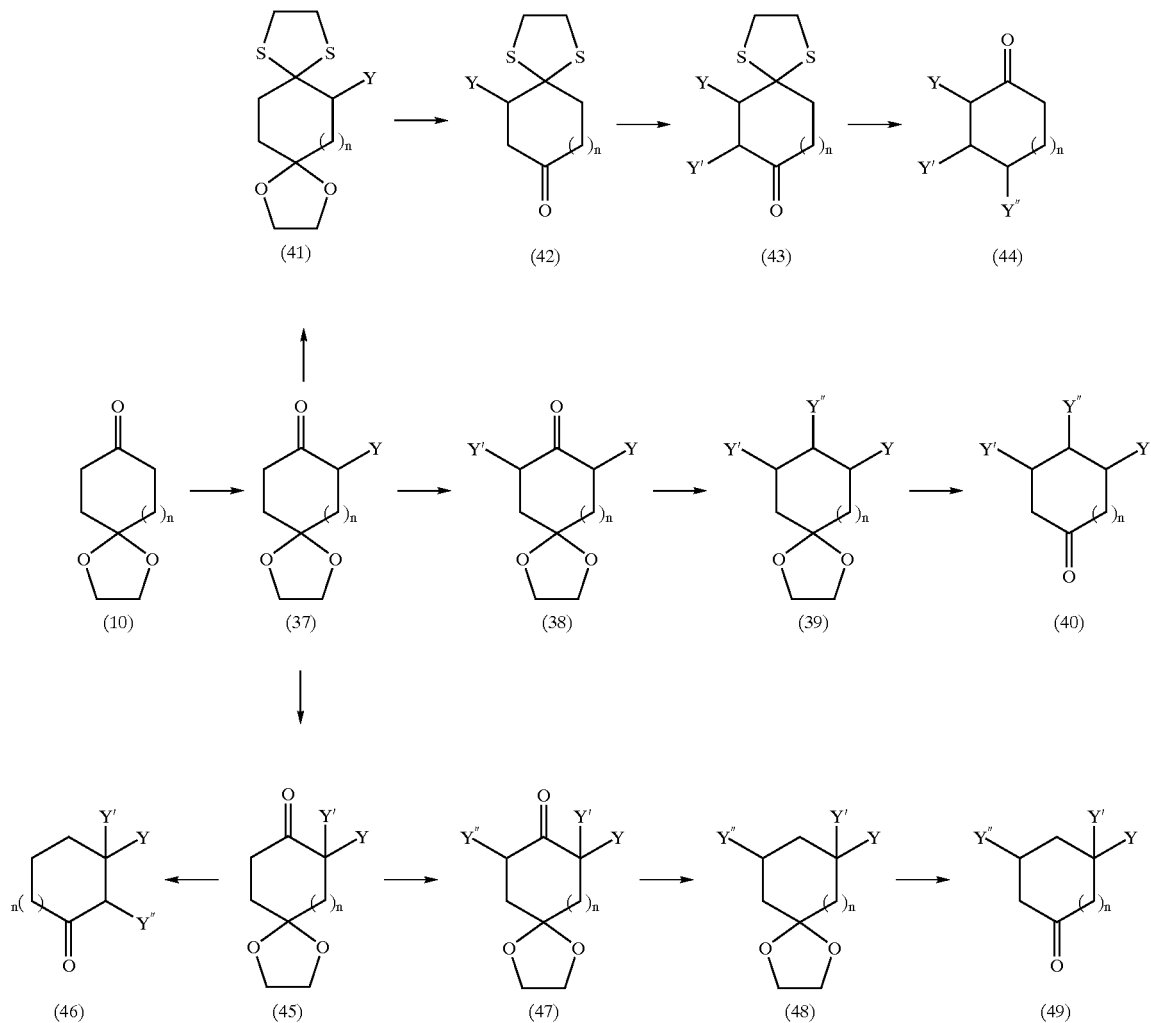
Scheme 11
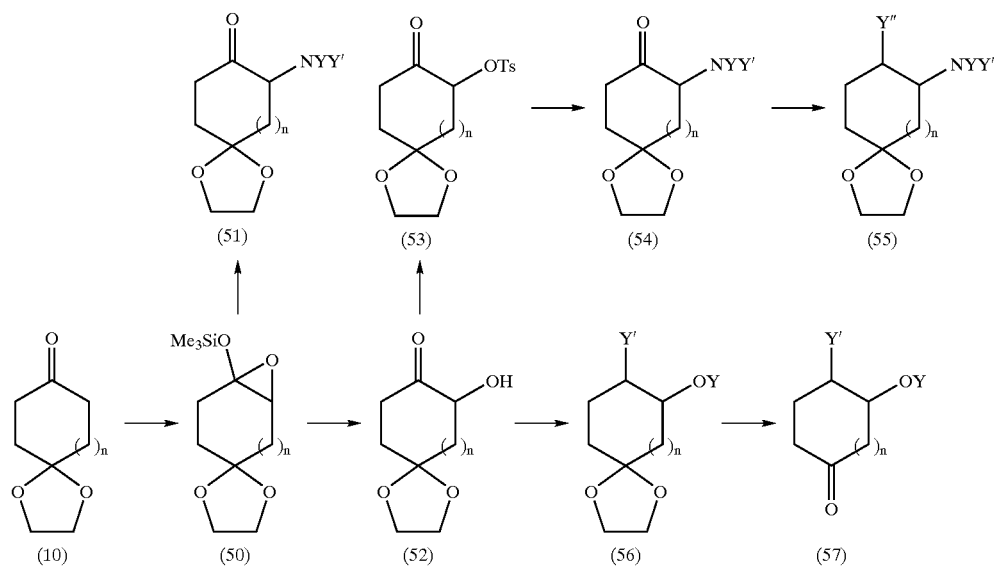

Scheme 12

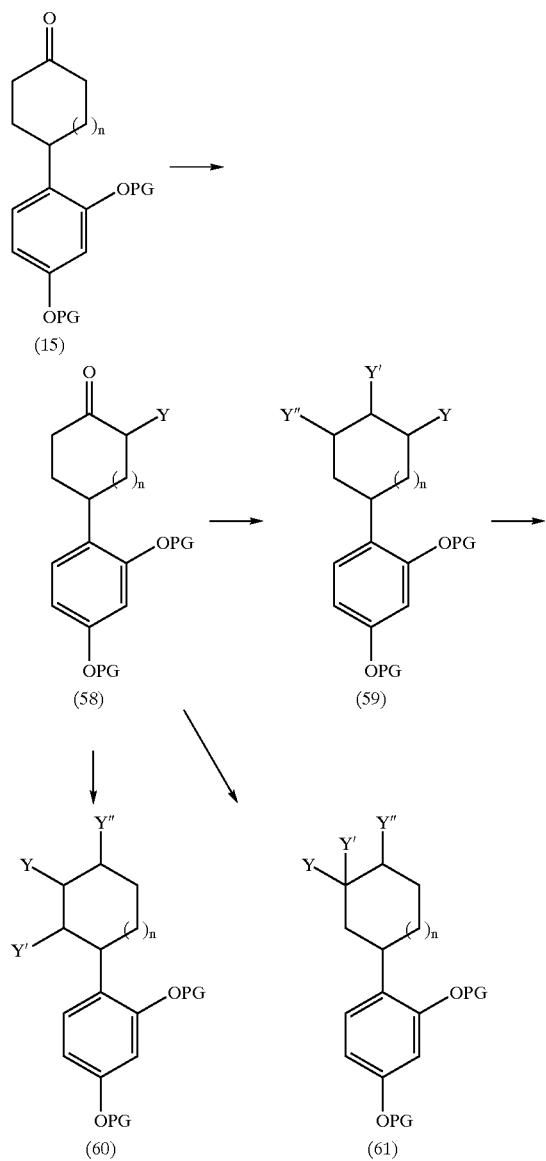

Y, Y', Y'' shown in the schemes above each independently represents any of the various substituents on $R^1$ as defined above, or hydrogen as appropriate.

Reaction Schemes 1 through 12 illustrate various methods of synthesizing compounds of formula I. PG refers to a protecting group.

Referring to Scheme 1, compounds of formula (2) can be formed by protecting commercially available 4-bromoresorcinol (1). A suitable protecting group such as methoxymethyl (MOM) can be introduced by conventional methods that are well known to those skilled in the art. For example, alkylation of 4-bromoresorcinol can occur with two equivalents of methoxymethyl chloride in the presence of diisopropylamine in a halogenated solvent at about 0° C. to room temperature.

Compounds of general formula (3) can be obtained using conventional methods. For example, the reaction of compounds of formula (2) with n-butyllithium in the presence of N,N,N',N'-tetramethylethylenediamine in a suitable solvent such as tetrahydrofuran, followed by quenching with triisopropyl borate and hydrolysing with aqueous acid, can yield compounds of formula (3).

Compounds of general formula (5) can be obtained using conventional methods. For example, the treatment of compounds of formula (4) with triphenylphosphine and bromine in a chlorinated solvent will yield compounds of formula (5). Compound (4) where n=1 is commercially available (Aldrich, Milwaukee, Wis., USA).

Compounds of formula (6) can be obtained by reacting compounds of formula (3) with compounds of formula (5) under Suzuki coupling conditions. For example, the Suzuki reaction can be carried out using palladium tetrakis (triphenylphosphine)palladium (five mole percent), sodium carbonate (two equivalents) and heating in a suitable solvent system (e.g., dimethoxyethane/water) at about 80° C. Conversion of compounds of formula (6) to compounds of formula (8) can occur under standard reducing conditions, such as, e.g., hydrogen gas and a metal catalyst such as rhodium on alumina, at about room temperature and atmospheric pressure. Deprotection of compounds of formula (6) or (8) under suitable conditions, e.g., where the protecting group is MOM, heating at 50° C. in methanol with acidic Dowex, gives compounds of formula I where $R^1$ is substituted with =O (7), (9). Compounds of formula (7) or (9) can be further derivatised under standard conditions to yield resorcinols of formula I where $R^1$ is substituted with =NOR 2. For example, heating compounds of formula (7) in a suitable solvent (e.g., ethanol) at about 80° C. with the required hydroxylamine hydrochloride salt and triethylamine yields the analogues of formula I. Compounds of formula I where $R^1$ is substituted with $NHOR^2$ can be prepared from compounds of formula I where $R^1$ is substituted with $=NOR^2$ by a reduction under standard reaction conditions, e.g., sodium cyanoborohydride in acetic acid at or about room temperature.

Compounds of formula (8) can be further derivatised under standard conditions to yield resorcinols of formula I where $R^1$ is disubstituted with fluoro. For example, treating compounds of formula (8) with diethylaminosulfur trifluoride in a suitable solvent, e.g. dimethoxyethane, after suitable deprotection, would give analogues of formula I.

Referring to Scheme 2, compounds of the general formula (10) are well known and can be obtained using conventional methods (see, e.g., Crombie et al., 1982, J. Chem. Soc. Perkin Trans. I, 1485). Compounds of formula (11) can be obtained from the reaction of compounds of formula (2) with n-butyllithium in the presence of N,N,N',N'-tetramethylethylenediamine in an ethereal solvent, followed by the addition of a compound of formula (10). Dehydration of compounds of formula (11) under standard conditions, e.g., heating compounds of formula (11) at about 110° C. in a Dean-Stark apparatus in the presence of camphor sulfonic acid in a suitable solvent (e.g., toluene), yields compounds of formula (12). Hydrogenation under standard conditions, e.g., using hydrogen gas and palladium on charcoal in ethanol, yields compounds of the general formula (13). Deprotection under suitable conditions yields resorcinols of formula I where $R^1$ is substituted with =O (14). Compounds of formula (14) can be further derivatised under standard conditions to yield resorcinols of formula I where $R^1$ is substituted with $=NOR^2$. For example, heating compounds of formula (14) in a suitable solvent (e.g., ethanol) at about 80° C. with the required hydroxylamine hydrochloride salt and triethylamine yields analogues of formula 1. Further reduction under standard conditions would yield compounds of formula 1, where $R^1$ is substituted with NHOR². Compounds of formula (14) can also be reprotected with a suitable protecting group such as tert-butyldimethylsilyl under standard reaction conditions to yield compounds of formula (15).

Compounds of formula (15) can be further derivatised using standard reaction conditions. For example, methylenation using an appropriate Wittig will yield compounds of formula (16), e.g., treatment of methyltriphenylphosphonium bromide with potassium t-butoxide in a suitable solvent (e.g., tetrahydrofuran) at a temperature between −78° C. and 0° C., followed by the addition of a compound of formula (15) will yield compounds of formula (16). Subsequent conversion to compounds of formula (18) under standard conditions, e.g. hydroboration, to give compounds of formula (17), and further oxidation using suitable conditions, such as pyridinium dichromate in dimethylformamide at room temperature, gives compounds of formula (18). Compounds of formula (17) can be treated with an alkyl bromide in a suitable solvent (e.g., acetone) in the presence of potassium carbonate to yield compounds of formula I where $R^1$ is substituted with an ether group after suitable deprotection has taken place, e.g. when the protecting group is tert-butyldimethylsilyl, tetrabutylammonium fluoride in tetrahydrofuran can be used. Alternatively, compounds of formula (17) can also be esterified under standard conditions, e.g. treatment with an acid chloride in the presence of triethylamine in a chlorinated solvent at about room temperature. Compounds of formula (18) can be derivatised to form analogues such as esters and amides under conditions well known to those with skill in the art. For example, conditions to form amides may involve treating compounds of formula (18) with iso-butylchloroformate and triethylamine in a chlorinated solvent at about 0° C., followed by the addition of a suitable amine. Deprotection under suitable conditions will yield compounds of formula I where $R^1$ is substituted with an amide. Deprotection of compounds of formula (16), (17) and (18) under standard conditions also provides compounds of formula I where $R^1$ is substituted with methylene, hydroxylmethyl or a carboxylic acid, respectively.

Referring to Scheme 3, compounds of formula (20) can be prepared starting with compound (19), which is commercially available. Conversion to compounds of formula (20) can occur under standard conditions such as, for example, where the protecting group is benzyl, condensation can occur between compound (19) and benzyl alcohol with the removal of water using a Dean-Stark apparatus in conjunction with well known methodology. Condensation of compounds of formula (20) with compounds of formula (10) can occur using standard techniques, for example, treatment of compounds of formula (20) with a base such as lithium diisopropylamide in an ethereal solvent followed by the addition of a compound of formula (10) would give compounds of formula (21). Treatment of compounds of formula (21) with a suitable reagent such as N-bromosuccinimide in a chlorinated solvent at about room temperature can give compounds of formula (22). Compounds of formula (23) can then be generated from compounds of formula (22) under suitable conditions. Such conditions can involve treating compounds of formula (22) with a base such as 1,8-diazobicyclo[5.4.0]undec-7-ene in a suitable solvent such as N,N-dimethylformamide at about 140° C. Treatment of compounds of formula (23) to standard hydrogenation conditions, e.g., hydrogen gas and palladium on charcoal in ethanol, yields compounds of the general formula (24) when the protecting group is benzyl. Compounds of formula (14) can then be obtained by treating compounds of formula (24) to acidic conditions.

Conversion of compounds of formula (14) to compounds of formula I may involve the need to use protecting groups that will be obvious to those of skill in the art. Some examples of such compounds of formula I are illustrated in Scheme 3. Conversion of compounds of formula (15) to compounds of formula I may involve the reduction of the ketone moiety under standard conditions, e.g., sodium borohydride in ethanol. Further derivitisation can occur, e.g. using chemistry described elsewhere in this document, to give compounds of formula I where $Y^1$ may be alkyl, acyl or a carbonylamino. In examples where protecting groups have been used, suitable deprotection will be required to yield compounds of formula I.

Alternatively, compounds of formula (15) can be manipulated to give compounds of formula I where $R^1$ is substituted with an amide or sulfonamide. Treatment of compounds of formula (15) with benzylamine under reductive amination conditions, e.g., one equivalent of sodium triacetoxyborohydride in a suitable solvent (dichloroethane) followed by hydrogenolysis under standard conditions, e.g., palladium on charcoal, hydrogen gas, ethanol, provides compounds of formula (25). Synthesis of compounds of formula I can be obtained using conventional methods. For example, compounds of formula (25) can react with sulfonyl chlorides and acid chlorides in a chlorinated solvent in the presence of a base (e.g. triethylamine) at about room temperature. Deprotection using suitable reaction conditions provides compounds of formula I where Y is a sulfonamide or amide group.

Referring to Scheme 4, compounds of formula (26) can be synthesized using standard methods. For example, compounds of formula (6) or (8) can be homologated using a Wittig reaction and further manipulated as described above to yield compounds of formula 1. Compounds of formula (26) or (16) from Scheme 2 can also undergo dihydroxylation under standard conditions, e.g. catalytic osmium tetroxide and N-methyl morpholine in an ethereal solvent, and after suitable deprotection yield compounds of formula I where $R^1$ is substituted with —(OH)(CH₂OH).

Referring to Scheme 5, compounds of formula (29) can be obtained by reacting compounds (6) or (8) as described above in Scheme 3. Compounds of formulae (29) and (25) can also be derivatised by treating with an alkylating agent, e.g., an alkyl iodide in a chlorinated solvent in the presence of triethylamine at about room temperature, to give compound (30) prior to sulfonylation or amide bond formation and deprotection, to yield compounds of formula I wherein Y is —N($R^5$)SO₂$R^4$ or equivalent amide where $R^5$ is not hydrogen.

Referring to Scheme 6, compounds of formula (6), (8) or (9), (14) or (15) can be treated with a suitable organometallic reagent, such as a Grignard reagent, in an ethereal solvent at a temperature between −78° C. and 0° C., followed by deprotection to yield compounds of formula I where $R^1$ is substituted with ($R^2$)OR².

Referring to Scheme 7, compounds of formula (31) can be formed under conditions well known to those skilled in the art. Treatment of compounds (6) or (8) with an amine, such as piperidine, in a suitable solvent (e.g., dichloroethane) and a reducing agent such as sodium triacetoxyborohydride, followed by deprotection will yield compounds of formula I where $R^1$ is substituted with a nitrogen-containing heterocycle.

Referring to Scheme 8, compounds of general formula (33) can be obtained using conventional methods. For example, the reaction of compounds of formula (2) with n-butyllithium in the presence of N,N,N',N'-tetramethylethylenediamine in a suitable solvent such as tetrahydrofuran, followed by quenching with ketone (32) (commercially available from Aldrich), and hydrolysing with aqueous acid, can yield compounds of formula (33). Functional group manipulation as outlined in Schemes 1–7 and Scheme 8 then allows the synthesis of compounds of formula 1.

Referring to scheme 9, compounds of formula (15), (6) or (8) can be further derivatised to yield compounds of formula (34) using standard Wittig or Wadworths-Emmons chemistry, followed by suitable deprotection. Compounds of formula (34) can be reduced using standard hydrogenation as described above to yield compounds where Y is OH, O-alkyl, or an aminoalkyl. Standard Wadworths-Emmons chemistry can also yield compounds of formula (35). Reduction under suitable conditions will yield compounds of formula (36), which can be further derivatised using standard chemistry described previously in this document to give compounds where $NY^IY^{II}$ is an amide, sulfonamide, or aminoalkyl.

Referring to Scheme 10, compounds of formula (10) can be converted into compounds of formula (37) using standard alkylation procedures. For example, compound (10) can be treated with a suitable base such as lithium diisopropyl amide in a suitable solvent such as tetrahydrofuran at a temperature between −78° C. and 0° C., followed by the addition of a suitable alkylating agent. Such alkylating agents are well known to those of skill in the art, and can include chloro, bromo, or iodoalkyl compounds; epoxides; aldehydes; aziridines; α,β-unsaturated esters, ketones or amides; acyl chlorides; electrophilic sources of oxygen such as $Mo(CO)_5$pyridine (Crimmons, M. T. et al., 1992, *J. Am. Chem. Soc.*, 114:5445); or electrophilic sources of nitrogen such as 2,4,6-triisopropylbenzene sulfonyl azide (Evans, P. A. et al., 1992, Tetrahedron Lett. 33:6959). Such alkylating reagents are commercially available or can be prepared by standard procedures well known to those of skill in the art.

Compounds of formula (37) can be further manipulated using methodology similar to that described above. For instance, alkylation of compounds of formula (37) under conditions of kinetic deprotonation (see, e.g., Kopka, I. and Rathke, M. W., 1981, *J. Org. Chem.* 46:3771), followed by alkylation as previously described, would yield compounds of formula (38). Alternatively, alkylation of compounds of formula (37) under conditions of thermodynamic deprotonation (Kopka and Rathke, 1981, above), followed by alkylation as previously described, would yield compounds of formula (45). Further alkylation or functional group manipulation known to those of skill in the art and, as described elsewhere in this document, followed by removal of the carbonyl protecting group under standard conditions, e.g., aqueous hydrochloric acid at about 0° C. to 50° C., would yield compounds of formulae (40), (46), and (49).

Compounds of formula (37) can also be protected with a suitable protecting group, e.g., ethylenedithio ketal, and after removal of the ketal protecting group under standard reaction conditions, e.g., aqueous hydrochloric acid at about 0° C. to 50° C., would allow further functionalisation of the cycloalkyl ring using the methodology described above to yield compounds of formula (44).

Referring to Scheme 11, compounds of formula (50) can be formed from compounds of formula (10) using known methodology (see, e.g., Adam, W. et al., 1989, *Tetrahedron Lett.* 30:6497) (Ts=tosyl). Standard functional group manipulation yields compounds of formula (55) and (57).

Oxirane ring cleavage by an amine yields compounds of formula (51). Alternatively, acid hydrolysis yields compounds of formula (52). Conversion of the corresponding alcohol to a leaving group such as para-toluenesulfonyl would allow the nucleophilic displacement with a range of nucleophiles under standard, well-known conditions. Such nucleophiles may include amines, thiolates, alkoxides, and carbon-based nucleophiles such as cyanide, which are commercially available or prepared by standard procedures well known to those of skill in the art.

Compounds of formula (40), (44) and (49) can be prepared using the above-described methods or other methods known in the art such that substituents on $R^1$ are as defined above.

Referring to Schemes 10 and 11, ketones of formulae (37), (38), (40), (42), (43), (44), (45), (46), (47), (49), (51), (54), (55), and (57) can be further manipulated as described in Schemes 1–9 above, and converted into compounds of formula I as described in Schemes 2 and 3.

Referring to Scheme 12, compounds of formula I can also be prepared using the methodology described above. Compounds of formula (58) can be converted into compounds of formula I using the chemistry as described in Schemes 1–11 above.

It will be appreciated by those of skill in the art that in the processes described above, the functional groups of intermediate compounds may need to be protected by protecting groups. The use of protecting groups is well-known in the art, and is fully described, among other places, in: *Protecting Groups in Organic Chemistry*, J. W. F. McOmie, (ed.), 1973, Plenum Press; and in: *Protecting Groups in Organic Synthesis*, $2^{nd}$ edition, T. W. Greene & P. G. M. Wutz, 1991, Wiley-Interscience, which are incorporated by reference in their entirety.

The compounds of the present invention can also be synthesized by application of alternative synthetic routes, such as those described in European Patent Application No. EP 1134207 A1 by Pfizer Products Inc, published Sep. 19, 2001.

The compounds of formula I that are basic in nature are capable of forming a wide variety of different salts with various inorganic and organic acids. Although such salts must be pharmaceutically acceptable for administration to animals, it is often desirable in practice to initially isolate a compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of formula I that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they can also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

Compounds of formula I and their pharmaceutically acceptable salts (hereinafter "the active compounds used in this invention") are useful in the treatment of disorders of human pigmentation, including solar and simple lentigines (including age/liver spots), melasma/chloasma and postinflammatory hyperpigmentation. Such compounds reduce skin melanin levels by inhibiting the production of melanin, whether the latter is produced constitutively or in response to UV irradiation (such as sun exposure). Thus, the active compounds used in this invention can be used to reduce skin melanin content in non-pathological states so as to induce a lighter skin tone, as desired by the user, or to prevent melanin accumulation in skin that has been exposed to UV irradiation. They can also be used in combination with skin peeling agents (including glycolic acid or trichloroacetic acid face peels) to lighten skin tone and prevent repigmentation. The appropriate dose regimen, the amount of each dose administered, and specific intervals between doses of the active compound will depend upon the particular active compound employed, the condition of the patient being treated, and the nature and severity of the disorder or condition being treated. Preferably, the active compound is administered in an amount and at an interval that results in the desired treatment of or improvement in the disorder or condition being treated.

An active compound used in the present invention can also be used in combination with sun screens (UVA or UVB blockers) to prevent repigmentation, to protect against sun or UV-induced skin darkening or to enhance their ability to reduce skin melanin and their skin bleaching action. An active compound used in the present invention can also be used in combination with retinoic acid or its derivatives or any compounds that interact with retinoic acid receptors and accelerate or enhance the invention's ability to reduce skin melanin and skin bleaching action, or enhance the invention's ability to prevent the accumulation of skin melanin. An active compound used in the present invention can also be used in combination with 4-hydroxyanisole.

The active compounds used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

Occurrences in the skin or hair of noticeable but undesired pigmentation as a result of melanin production, overproduction or underproduction can be treated using the methods of the present invention. Cosmetic applications for methods of the present invention include the topical application of compositions containing one or more of the compounds of the present invention to enhance or otherwise alter the visual appearance of skin or hair. The cosmetic compositions of the present invention are also useful to provide a smoother or softer skin appearance or texture.

As one skilled in the art would know in view of this disclosure, an active compound used in the methods of the present invention may be used alone or in combination with other compounds known in the art to affect melanin synthesis, particularly other melanin synthesis inhibitors, including tyrosinase inhibitors. Such inhibitors include those currently known in the art and those to be developed in the future. Known inhibitors include various resorcinol derivatives, kojic acid derivatives, hydroquinone, melamine, and various types of plant extracts, among others. For example, any of the compounds used according to a skin-lightening method of the present invention may be used in combination with a tyrosinase inhibitor or other skin-whitening agent, including any one or more of those agents, including compounds or extracts, described in the following patent publications: U.S. Pat. No. 4,278,656 to Nagai et al, issued Jul. 14, 1981, describing the use of kojic acid and its derivatives; U.S. Pat. No. 4,369,174 to Nagai et al., issued Jan. 18, 1983, describing the use of kojic acid and its derivatives; U.S. Pat. No. 4,959,393 to Torihara et al., issued Sep. 25, 1990, describing the use of 4-n-butylresorcinol, 4-isoamyl resorcinol and other resorcinol derivatives; U.S. Pat. No. 5,580,549 to Fukuda et al., issued Dec. 3, 1996, describing the use of various hydroxybenzoic acid derivatives; U.S. Pat. No. 6,123,959 to Jones et al., issued Sep. 26, 2000, describing the use of liposomes containing combinations of competitive inhibitors, such as arbutin, and non-competitive inhibitors, such as aloesin, of melanin synthesis; U.S. Pat. No. 6,132,740 to Hu, issued Oct. 17, 2000, describing the use of various resorcinol derivatives; U.S. Pat. No. 6,159,482 to Tuloup et a al., issued Dec. 12, 2000, describing the use of various hydroxyphenyl oxamate derivatives; WO 99/32077 by L'Oreal, published Jul. 1, 1999, describing the use of various phenolic amides; WO 99/64025 by Fytokem Prod. Inc., published Dec. 16, 1999, describing the use of various dicotyledonous plant extracts; WO 00/56702 by Pfizer Inc., published Sep. 28, 2000 describing various resorcinol derivatives; WO 00/76473 by Shiseido Co. Ltd., published Dec. 12, 2000, describing the use of Withania plant extracts; EP 997140 by L'Oreal SA, published May 3, 2000, describing the use of combinations of mulberry and skullcap extracts with salicylic acid derivatives; JP 5221846 by Kunimasa Tomoji, published Aug. 31, 1993, describing the use of kojic acid derivatives; JP 7242687 by Shiseido Co. Ltd., published Sep. 19, 1995, describing the use of Trichoderma extracts; JP 7324023 by Itogawa H, published Dec. 12, 1995, describing the use of *Pseudostellariae radix* extracts; JP 8012552 by Shiseido Co. Ltd., published Jan. 16, 1996, describing the use of *Amor seco* extracts; JP 8012554 by Shiseido Co. Ltd., published Jan. 16, 1996, describing the use of Jabonciilo extracts; JP 8012557 by Shiseido Co. Ltd., published Jan. 16, 1996, describing the use of Huaca extracts; JP 8012560 by Shiseido Co. Ltd., published Jan. 16, 1996, describing the use of Copaiba extracts; JP 8012561 by Shiseido Co. Ltd., published Jan. 16, 1996, describing the use of Arnica extracts; JP 8134090 by Fujisawa, published May 28, 1996, describing the use of galactosyl-kojic acid derivatives; JP 8168378 by Kirinjo KK, published Jul. 2, 1996, describing the use of lees from rice wine production; JP 8277225 by Kansai Koso KK, published Oct. 22, 1996, describing the use of *Autocarpus incisus* extracts; JP 9002967 by Sanki Shoji KK, published Jan. 7, 1997, describing the use of *Prunus domesticus* extracts; JP 9295927 by Yagi Akira, published Nov. 18, 1997, describing the use of Aloe vera extracts; JP 10072330 by Kansai Kouso, published Mar. 17, 1998, describing the use of oxydesberatrol derivatives; JP 10081626 by Kamiyama KK, published Mar. 31, 1998, describing the use of 4-substituted benzoic acids; JP 10101543 by Kansai Kouso KK, published Apr. 21, 1998, describing the use of flavonoids; JP 11071231 by Maruzen Pharm., published Mar. 16, 1999, describing the use of bakuchiol; JP 11079934 by Kyodo Nyugyo, published Mar. 23, 1999, describing the use of low molecular weight thiol from sake lees; JP 11246347 by Shiseido Co. Ltd., published Sep. 14, 1999, describing the use of Achillea millefolium extracts; JP 11246344 by Shiseido Co. Ltd., published Sep. 14, 1999, describing the use of Gliricidia extracts; JP 2000-080023 by Kanebo Ltd., published Mar. 21, 2000, describing the use of metallothionine inducers; JP 2000-095663 by Kose KK, published Apr. 4, 2000, describing the use of various plant extracts; JP 2000-159681 by Hai Tai Confectionary Co. Ltd., published Jun. 13, 2000, describing the use of grape seed extract; JP-7206753 by Nikken Food KK, published Aug. 8, 1995, describing the use of dihydroxy-curcumin derivatives; JP-5320025 by Kunimasa T, published Dec. 3, 1993, describing the use of kojic acid derivatives; and JP-59157009 by Yakurigaku Chuou K E, published Sep. 6, 1984, describing the use of P-thujaplicin, hydroquinone or a pyrone compound in combination with a melanin adsorbent; among others; which patent publications are incorporated herein by reference in their entireties.

This invention relates both to methods of lightening or reducing the pigmentation of skin in which the compound of formula I, or pharmaceutically acceptable salt thereof, and one or more of the other active ingredients referred to above are administered together, as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

The active compounds of the present invention are generally administered in the form of pharmaceutical compositions comprising at least one of the compounds of formula (I), together with a pharmaceutically acceptable vehicle or diluent. Alternatively, an active compound of this invention can be administered in the form of a cosmetic composition comprising at least one compound of formula (I), together with a cosmetically acceptable vehicle or diluent. Such compositions are generally formulated in a conventional manner utilizing solid or liquid vehicles or diluents as appropriate for topical administration, in the form of solutions, gels, creams, jellies, pastes, lotions, ointments, salves, aerosols and the like.

Examples of vehicles for application of the active compounds of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof. Such vehicles can include suitable viscosity enhancing agents, pH adjusting agents, stabilizers, fragrances, etc., as known in the art of topical formulations.

An effective dosage and treatment protocol can be determined by conventional means, starting with a low dose in laboratory animals and then increasing the dosage while monitoring the effects, and systematically varying the dosage regimen as well. Animal studies, preferably mammalian studies, are commonly used to determine the maximal tolerable dose, or MTD, of a bioactive agent per kilogram weight. Those skilled in the art can a extrapolate doses for efficacy and avoidance of toxicity to other species, including humans.

Before human studies of efficacy are undertaken, Phase I clinical studies in normal subjects can help establish safe doses. Numerous factors can be taken into consideration by a clinician when determining an optimal dosage for a given subject. Primary among these is the toxicity and half-life of the chosen compound. Additional factors include the size of the patient, the age of the patient, the general condition of the patient, the particular disease, condition, or disorder being treated, the severity of the disease, condition, or disorder being treated, the presence of other drugs in the patient, the effect desired, and the like. The trial dosages would be chosen after consideration of the results of animal studies and the clinical literature.

One of ordinary skill in the art will appreciate that the endpoint of treatment chosen in a particular case will vary according to the disease, condition, or disorder being treated, the outcome desired by the patient, subject, or treating physician, and other factors. Where the composition is being used to lighten skin color such as, for example, to reverse hyperpigmentation caused by, for example, inflammation or diseases such as melasma, or to lighten hair color, any one of a number of endpoints can be chosen. For example, endpoints can be defined subjectively such as, for example, when the subject is simply "satisfied" with the results of the treatment. For pharmacological compositions, the endpoint can be determined by the patient's, or the treating physician's, satisfaction with the results of the treatment. Alternatively, endpoints can be defined objectively. For example, the patient's or subject's skin or hair in the treated area can be compared to a color chart. Treatment is terminated when the color of the skin or hair in the treated area is similar in appearance to a color on the chart. Alternatively, the reflectance of the treated skin or hair can be measured, and treatment can be terminated when the treated skin or hair attains a specified reflectance. Alternatively, the melanin content of the treated hair or skin can be measured. Treatment can be terminated when the melanin content of the treated hair or skin reaches a specified value. Melanin content can be determined in any way known to the art, including by histological methods, with or without enhancement by stains for melanin.

In the depigmenting compositions according to the present invention, the concentration of the active compound of the invention is generally between 0.01 and 10%, preferably between 0.1 and 10%, relative to the total weight of the composition.

The compositions of this invention can optionally also contain a moistener, a surfactant, keratolytic, an anti-inflammatory agent, a complexing agent, an antioxidant, a preservative, a colorant, a fragrance, or a sunscreen.

The compositions of the present invention can be applied directly to the skin. Alternatively, they can be delivered by various transdermal drug delivery systems, such as transdermal patches as known in the art. For example, for topical administration, the active ingredient can be formulated in a solution, gel, lotion, ointment, cream, suspension, paste, liniment, powder, tincture, aerosol, patch, or the like in a pharmaceutically or cosmetically acceptable form by methods well known in the art. The composition can be any of a variety of forms common in the pharmaceutical or cosmetic arts for topical application to animals or humans, including solutions, lotions, sprays, creams, ointments, salves, gels, etc., as described below. Preferred agents are those that are viscous enough to remain on the treated area, those that do not readily evaporate, and/or those that are easily removed by rinsing with water, optionally with the aid of soaps, cleansers and/or shampoos. Actual methods for preparing topical formulations are known or apparent to those skilled in the art, and are described in detail in Remington's Pharmaceutical Sciences, 1990 (supra); and Pharmaceutical Dosage Forms and Drug Delivery Systems, 6th ed., Williams & Wilkins (1995).

In order to enhance the percutaneous absorption of the active ingredients, one or more of a number of agents can be added in the topical formulations including, but not limited to, dimethylsulfoxide, dimethylacetamide, dimethylformamide, surfactants, azone, alcohol, acetone, propylene glycol and polyethylene glycol. In addition, physical methods can also be used to enhance transdermal penetration such as, e.g., by iontophoresis or sonophoresis. Alternatively, or in addition, liposomes may be employed.

A topically applied composition of the invention contains a pharmaceutically effective agent that lightens skin as described herein, and those ingredients as are necessary for use as a carrier, such as an emulsion, a cream, an ointment, an aqueous solution, a lotion or an aerosol. Non-limiting examples of such carriers are described in more detail below and may be found in International Patent Publication WO 00/62742, published Oct. 26, 2000; U.S. Pat. No. 5,691,380 to Mason et al., issued Nov. 25, 1997; U.S. Pat. No. 5,968,528 to Deckner et al., issued Oct. 19, 1999; U.S. Pat. No. 4,139,619 to Chidsey, III, issued Feb. 13, 1979; and U.S. Pat. No. 4,684,635 to Orentreich et al., issued Aug. 4, 1987; which are incorporated herein by reference. Suitable pharmaceutical carriers are further described in Remington's Pharmaceutical Sciences, 17th ed., Mack Publishing Company, Easton, Pa. (1990), which is a standard reference text in this field.

The pharmaceutical compositions of the invention may optionally include components suitable for application to keratinous tissue, that is, when incorporated into the composition, they are suitable for use in contact with human keratinous tissue without undue toxicity, incompatibility, instability, allergic response, and the like within the scope of sound medical judgment. In addition, such optional components are useful provided that they do not unacceptably alter the benefits of the active compounds of the invention. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin and bisabolol and dipotassium glycyrrhizinate), skin treating agents, thickeners, and vitamins and derivatives thereof.

In addition to the pharmaceutically effective amount of an agent disclosed herein, the topical compositions of the present invention also comprise a dermatologically acceptable carrier. The phrase "dermatologically acceptable carrier", as used herein, means that the carrier is suitable for topical application to the skin, i.e., keratinous tissue, has good aesthetic properties, is compatible with the active agents of the present invention and any other components, and will not cause any safety or toxicity concerns. A safe and effective amount of carrier is from about 50% to about 99.99%, preferably from about 80% to about 99.9%, more preferably from about 90% to about 98%, and most preferably from about 90% to about 95% of the composition.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Preferred emulsions also contain a humectant, such as glycerin. Emulsions will preferably further contain from about 1% to about 10%, more preferably from about 2% to about 5%, of an emulsifier, based on the weight of the carrier. Emulsifiers may be nonionic, anionic or cationic. Suitable emulsifiers are described in, for example, U.S. Pat. No. 3,755,560 to Dickert et al., issued Aug. 28, 1973; U.S. Pat. No. 4,421,769 to Dixon, et al., issued Dec. 20, 1983; and McCutcheon's Detergents and Emulsifiers, North American Edition, pages 317–324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, most preferably about 5 centistokes or less. The emulsion may also contain an anti-foaming agent to minimize foaming upon application to the keratinous tissue. Anti-foaming agents include high molecular weight silicones and other materials well known in the art for such use.

One type of emulsion is a water-in-silicone emulsion. Water-in-silicone emulsions contain a continuous silicone phase and a dispersed aqueous phase. Preferred water-in-silicone emulsions of the present invention comprise from about 1% to about 60%, preferably from about 5% to about 40%, more preferably from about 10% to about 20%, by weight of a continuous silicone phase. The continuous silicone phase exists as an external phase that contains or surrounds the discontinuous aqueous phase described hereinafter.

The continuous silicone phase may contain a polyorganosiloxane oil. A preferred water-in-silicone emulsion system is formulated to provide an oxidatively stable vehicle for delivery of a pharmaceutically effective amount of an agent disclosed herein. The continuous silicone phase of these preferred emulsions comprises between about 50% and about 99.9% by weight of organopolysiloxane oil and less than about 50% by weight of a non-silicone oil. In an especially preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less than about 40%, more preferably less than about 30%, even more preferably less than about 10%, and most preferably less than about 2%, by weight of the continuous silicone phase. These useful emulsion systems may provide more oxidative stability over extended periods of time than comparable water-in-oil emulsions containing lower concentrations of the polyorganosiloxane oil. Concentrations of non-silicone oils in the continuous silicone phase are minimized or avoided altogether so as to possibly further enhance oxidative stability of the active compound of the invention in the compositions. Water-in-silicone emulsions of this type are described in U.S. Pat. No. 5,691,380 to Mason et al., issued Nov. 25, 1997.

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100 degrees Celsius. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes, which are known to those skilled in the art and commercially available.

The continuous silicone phase may contain one or more non-silicone oils. Concentrations of non-silicone oils in the continuous silicone phase are preferably minimized or avoided altogether so as to further enhance oxidative stability of the pharmaceutically effective agent in the compositions. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g. mineral oil, vegetable oils, synthetic oils, semisynthetic oils, etc.

Useful topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase.

The dispersed aqueous phase is a dispersion of small aqueous particles or droplets suspended in and surrounded by the continuous silicone phase described hereinbefore. The aqueous phase can be water, or a combination of water and one or more water soluble or dispersible ingredients. Non-limiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention typically comprise from about 25% to about 90%, preferably from about 40% to about 80%, more preferably from about 60% to about 80%, water in the dispersed aqueous phase by weight of the composition.

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, e.g., organically modified organopolysiloxanes, also known to those skilled in the art as silicone surfactants, non-silicon-containing emulsifiers, and mixtures thereof, known by those skilled in the art for use in topical personal care products.

Useful emulsifiers include a wide variety of silicone emulsifiers. These silicone emulsifiers are typically organically modified organopolysiloxanes, also known to those skilled in the art as silicone surfactants. Suitable emulsifiers are described, for example, in McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Other preferred topical carriers include oil-in-water emulsions, having a continuous aqueous phase and a hydrophobic, water-insoluble phase ("oil phase") dispersed therein. Examples of suitable carriers comprising oil-in-water emulsions are described in U.S. Pat. No. 5,073,371 to Turner et al., issued Dec. 17, 1991; and U.S. Pat. No. 5,073,372, to Turner et al., issued Dec. 17, 1991. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing Theological characteristics to the composition which contribute to the stability of the composition. The structuring agent may also function as an emulsifier or surfactant. Preferred compositions of this invention comprise from about 0.5% to about 20%, more preferably from about 1% to about 10%, most preferably from about 1% to about 5%, by weight of the composition, of a structuring agent. The preferred structuring agents of the present invention are selected from the group consisting of stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

The preferred oil-in-water emulsions comprise from about 0.05% to about 10%, preferably from about 1% to about 6%, and more preferably from about 1% to about 3% of at least one hydrophilic surfactant which can disperse the hydrophobic materials in the water phase (percentages by weight of the topical carrier). The surfactant, at a minimum, must be hydrophilic enough to disperse in water. Suitable surfactants include any of a wide variety of known cationic, anionic, zwitterionic, and amphoteric surfactants. See McCutcheon's. Detergents and Emulsifiers (1986), supra; U.S. Pat. No. 5,011,681 to Ciotti et al., issued Apr. 30, 1991; U.S. Pat. No. 4,421,769 to Dixon et al. issued Dec. 20, 1983; and U.S. Pat. No. 3,755,560 to Dickert et al., issued Aug. 28, 1973. The exact surfactant chosen depends upon the pH of the composition and the other components present. Preferred are cationic surfactants, especially dialkyl quaternary ammonium compounds, examples of which are described in U.S. Pat. No. 5,151,209 to McCall et al. issued Sep. 29, 1992; U.S. Pat. No. 5,151,210 to Steuri et al. issued Sep. 29, 1992; U.S. Pat. No. 5,120,532 to Wells et al, issued Jun. 9, 1992; U.S. Pat. No. 4,387,090 to Bolich Jr., issued Jun. 7, 1983; U.S. Pat. No. 3,155,591 to Hilfer, issued Nov. 3, 1964; U.S. Pat. No. 3,929,678 to Laughlin et al, issued Dec. 30, 1975; U.S. Pat. No. 3,959,461 to Bailey et al., May 25, 1976; McCutcheon's, Detergents & Emulsifiers (North American edition 1979) M.C. Publishing Co.; and Schwartz, et al., Surface Active Agents, Their Chemistry and Technology, New York: Interscience Publishers, 1949.

Alternatively, other useful cationic emulsifiers include amino-amides. Non-limiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

A wide variety of anionic surfactants are also useful herein. See, e.g., U.S. Pat. No. 3,929,678, to Laughlin et al., issued Dec. 30, 1975. In addition, amphoteric and zwitterionic surfactants are also useful herein.

The preferred oil-in-water emulsion comprises from about 25% to about 98%, preferably from about 65% to about 95%, more preferably from about 70% to about 90% water by weight of the topical carrier.

The hydrophobic phase is dispersed in the continuous aqueous phase. The hydrophobic phase may contain water-insoluble or partially soluble materials such as are known in the art, including but not limited to the silicones described herein in reference to silicone-in-water emulsions, and other oils and lipids such as described above in reference to emulsions.

The topical compositions of the subject invention, including but not limited to lotions and creams, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. See, e.g., Sagarin, Cosmetics, Science and Technology, 2nd Edition, Vol. 1, pp. 3243 (1972), which contains numerous examples of materials suitable as an emollient. A preferred emollient is glycerin. Glycerin is preferably used in an amount of from or about 0.001 to or about 20%, more preferably from or about 0.01 to or about 10%, most preferably from or about 0.1 to or about 5%, e.g., 3%.

Lotions and creams according to the present invention generally comprise a solution carrier system and one or more emollients. Lotions typically comprise from about 1% to about 20%, preferably from about 5% to about 10% of emollient; from about 50% to about 90%, preferably from about 60% to about 80% water; and a pharmaceutically effective amount of an agent described herein. A cream typically comprises from about 5% to about 50%, preferably from about 10% to about 20% of emollient; from about 45% to about 85%, preferably from about 50% to about 75% water; and a pharmaceutically effective amount of an agent described herein.

Ointments of the present invention may comprise a simple carrier base of animal or vegetable oils or semi-solid hydrocarbons (oleaginous); absorption ointment bases, which absorb water to form emulsions; or water soluble carriers, e.g., a water soluble solution carrier. Ointments may further comprise a thickening agent, such as described in Sagarin, Cosmetics, Science and Technology, 2nd Edition, Vol. 1, pp. 72–73 (1972), incorporated herein by reference, and/or an emollient. For example, an ointment may comprise from about 2% to about 10% of an emollient; from about 0.1% to about 2% of a thickening agent; and a pharmaceutically effective amount of an agent described herein.

By way of non-limiting example, 1000 g of topical cream is prepared from the following types and amounts of ingredients: a pharmaceutically effective amount of an agent disclosed herein, tegacid regular (150 g) (a self-emulsifying glyceryl monostearate from Goldschmidt Chemical Corporation, New York, N.Y.), polysorbate 80 (50 g), spermaceti (100 g), propylene glycol (50 g), methylparaben (1 g), and deionized water in sufficient quantity to reach 1000 gm. The tegacid and spermaceti are melted together at a temperature of 70–80° C. The methylparaben is dissolved in about 500 g. of water and the propylene glycol, polysorbate 80, and active compound are added in turn, maintaining a temperature of 75–800 C. The methylparaben mixture is added slowly to the tegacid and spermaceti melt, with constant stirring. The addition is continued for at least 30 minutes with additional stirring until the temperature has dropped to 40–45° C. Finally, sufficient water is added to bring the final weight to 1000 g. and the preparation stirred to maintain homogeneity until cooled and congealed.

By way of non-limiting example, 1000 g of a topical ointment is prepared from the following types and amounts of ingredients: a pharmaceutically effective amount of an agent disclosed herein, zinc oxide (50 g), calamine (50 g), liquid petrolatum (heavy) (250 g), wool fat (200 g), and enough white petrolatum to reach 1000 g. Briefly, the white petrolatum and wool fat are melted and 100 g of liquid petrolatum added thereto. The pharmaceutically effective amount of an agent disclosed herein, zinc oxide, and calamine are added to the remaining liquid petrolatum and the mixture milled until the powders are finely divided and uniformly dispersed. The mixture is stirred into the white petrolatum, melted and cooled with stirring until the ointment congeals.

By way of non-limiting example, 1000 g of an ointment containing a pharmaceutically effective amount of an agent disclosed herein is prepared from the following types and amounts of ingredients: a pharmaceutically effective amount of an agent disclosed herein, light liquid petrolatum (250 g), wool fat (200 g), and enough white petrolatum to reach 1000 g. Briefly, the pharmaceutically effective amount of an agent disclosed herein is finely divided and added to the light liquid petrolatum. The wool fat and white petrolatum are melted together, strained, and the temperature adjusted to 45–50° C. The liquid petrolatum slurry is added, and the ointment stirred until congealed.

By way of non-limiting example, 1000 ml of an aqueous solution containing a pharmaceutically effective amount of an agent disclosed herein is prepared from the following types and amounts of ingredients: a pharmaceutically effective amount of an agent disclosed herein, polyethylene glycol 4000 (120 g) myristyl-gamma-picolinium chloride (0.2 g), polyvinylpyrrolidone (1 g), and enough deionized water to reach 1000 milliliters. Briefly, the ingredients are dissolved in the water and the resulting solution is sterilized by filtration.

By way of non-limiting example, 1000 g of lotion containing a pharmaceutically effective amount of an agent disclosed herein is prepared from the following types and amounts of ingredients: a pharmaceutically effective amount of an agent disclosed herein, N-methyl pyrolidone (40 g), and enough propylene glycol to reach 1000 g.

By way of non-limiting example, an aerosol containing a pharmaceutically effective amount of an agent disclosed herein is prepared from the following types and amounts of materials: a pharmaceutically effective amount of an agent disclosed herein, absolute alcohol (4.37 g), dichlorodifluoroethane (1.43 g) and dichlorotetrafluoroethane (5.70 g). Briefly, the pharmaceutically effective amount of an agent disclosed herein is dissolved in the absolute alcohol and the resulting solution filtered to remove particles and lint. This solution is chilled to about minus 30° C. Then, to this is added the chilled mixture of dichlorodifluoromethane and dichlorotetrafluoroethane.

For oral administration, gelatin capsules or liquid-filled soft gelatin capsules can contain the active ingredient and powdered or liquid carriers, such as lactose, lecithin starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and to protect the tablet from the atmosphere, or enteric-coated for selective, targeted disintegration in the gastrointestinal tract. Liquid dosage forms for oral administration can contain coloring and/or flavoring to increase patient acceptance.

In general, sterile water, oil, saline, aqueous dextrose (glucose), polysorbate and related sugar solutions and glycols such as propylene glycol or polyethylene glycols, are suitable carriers for parenteral solutions. Solutions or emulsions for parenteral administration preferably contain about 5–15% polysorbate 80 or lecithin, suitable stabilizing agents and, if necessary, buffer substances. Anti-oxidizing agents such as, but not limited to, sodium bisulfite, sodium sulfite, or ascorbic acid, either alone or combined, are suitable stabilizing agents. Also useful are citric acid and its salts, and sodium EDTA. In addition, parenteral solutions can contain preservatives including, but not limited to, benzalkonium chloride, methyl- or propyl-paraben, and chlorobutanol.

Additional examples of particular formulations comprising an active compound of the present invention are provided below.

An example of the preparation of a topical gel follows.

TABLE 1

| Topical Gel: | |
|---|---|
| Ingredient | Percent by Weight |
| Active compound | 0.50 |
| Propylene glycol | 20.00 |
| Ethanol | 20.00 |
| Carboxyvinyl polymer [Carbomer 940 ™] | 1.00 |
| Hydroxyethyl cellulose | 0.40 |
| Benzyl alcohol | 1.00 |
| Sodium hydroxide 1N | to pH 6 |
| Distilled water | Balance |

The components other than sodium hydroxide are combined to yield a homogeneous dispersion. Addition of sodium hydroxide causes the mixture to gel yielding a ready-to-use semisolid.

An example of the preparation of a topical cream follows.

TABLE 2

| Topical Cream: | |
|---|---|
| Ingredient | Percent by Weight |
| Active compound | 0.50 |
| Stearic acid | 7.00 |
| Stearyl alcohol | 5.00 |
| Cetyl alcohol | 2.00 |
| Glycerin | 10.00 |
| Sodium laurylsulfate | 1.00 |
| Propylparaben | 0.05 |
| Methylparaben | 0.25 |
| Disodium edetate | 0.05 |
| Distilled water | Balance |

The first four ingredients are heated to approximately 70° C. to produce a uniform melt. The remaining ingredients are combined, heated to approximately 75° C., and added with mixing to the previously prepared melt. The emulsion thus formed is subsequently homogenized and cooled to yield a smooth white cream.

An example of the preparation of a topical lotion follows.

TABLE 3

| Topical Lotion: | |
|---|---|
| Ingredient | Percent by Weight |
| Active compound | 0.50 |
| Glyceryl monostearate | 1.00 |
| Isopropyl palmitate | 4.00 |
| Polyethylene glycol 400 distearate | 2.00 |
| Glycerin | 10.00 |
| Methylparaben | 0.10 |
| Sodium cetylsulfate | 5.00 |
| Distilled water | Balance |

The first four ingredients are combined and heated to approximately 70° C., then added with agitation to a mixture of the remaining ingredients, also at about 70° C. The emulsion is appropriately homogenized and cooled to produce a smooth, white, pourable lotion.

An example of the preparation of a topical solution follows.

TABLE 4

Topical Solution:

| Ingredient | Percent by Weight |
| --- | --- |
| Active compound | 0.50 |
| Propylene glycol | 20.00 |
| Ethanol | 50.00 |
| Benzyl alcohol | 1.00 |
| Disodium edetate | 0.01 |
| Propyl gallate | 0.10 |
| Citric acid | 0.20 |
| Sodium hydroxide 1N | to pH 6 |
| Distilled water | Balance |

All ingredients except sodium hydroxide are combined with agitation, and the pH of the resultant solution is adjusted with 1 N sodium hydroxide, to pH 6, to yield a free-flowing, quick-drying topical solution.

The topical formulations presented herein are examples of typical gel, cream, lotion, or solution dosage forms of active compounds for use in lightening skin. Other optional components can be added or excipient ratios can be adjusted to enhance cosmetic acceptability of the formulations. Additionally, these alterations can be made to customize the composition toward a particular active compound, for example, to ensure solubilization or to enhance chemical or physical stability. Optional components would include viscosity adjusters such as celluloses, emollient oils such as mineral oil or glycerides, humectants such as polyols, cosolvents such as isopropyl alcohol or acetone, emulsifying agents of the anionic, cationic and non-ionic types, preservatives, antioxidants, opacifiers, colorants and perfumes.

An example of the preparation of an oral tablet formulation follows.

TABLE 5

Tablet Formulation:

| Ingredient | Amount (mg) |
| --- | --- |
| Active Compound | 25 |
| Lactose | 50 |
| Cornstarch (for mix) | 10 |
| Cornstarch (paste) | 10 |
| Magnesium stearate (1%) | 5 |
| Total | 100 |

The active compound, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet.

An example of the preparation of an oral solution follows.

TABLE 6

Oral Solution:

| Ingredient | Percent by Weight |
| --- | --- |
| Active Compound | 2.0 |
| Ethyl alcohol | 10.0 |
| Benzyl alcohol | 1.0 |
| Peppermint flavor | 0.2 |
| Vanillin | 0.2 |
| Polysorbate 40 | 0.1 |
| Sucrose | 50.0 |
| Purified water | Balance |

The ingredients are combined and mixed to form a uniform solution.

The present invention further provides a kit comprising a container comprising a pharmaceutical composition of the present invention. The container is designed to prevent contamination, minimize evaporation or drying of the composition, etc. The composition may or may not be provided in a preset unit dose or usage amount. The kit may further comprise a package insert comprising printed instructions directing the use of the pharmaceutical composition for lightening the skin.

The ability of compounds of formula I to inhibit tyrosinase may be determined using any of the following procedures.

1. Tyrosinase (DOPA oxidase) Assay Using Cell Lysate:

Human melanoma cell line, SKMEL 188 (licensed from Memorial Sloan-Kettering), is used in the cell lysate assay and the screen. In the assay, compounds and L-dihydroxyphenylalanine (L-DOPA) (100 $\mu$g/ml) are incubated with the cell lysates containing human tyrosinase for 8 hrs before the plates are read at 405 nm. Potency of the compounds in DOPA oxidase assay is correlated very well with that in tyrosine hydroxylase assay using $^3$H-tyrosine as a substrate. Most of the compounds of formula I that were tested in this assay exhibited an $IC_{50}$ of less than 10 $\mu$M. For example, the compound of Example 23, i.e., (±)-3-(2,4-Dihydroxyphenyl)cyclopentanone oxime, had an $IC_{50}$ in this assay of about 2 $\mu$m.

2. Melanin Assay in Human Primary Melanocytes:

Compounds are incubated with human primary melanocytes in the presence of α-melanocyte stimulating hormone (α-MSH) for 2–3 days. Cells are then lysed with sodium hydroxide and sodium dodecyl sulfate (SDS) and melanin signals are read at 405 nm. Alternatively, $^{14}$C-DOPA is added to the cells in combination with tyrosinase inhibitors and acid-insoluble $^{14}$C-melanin is quantitated by a scintillation counter. $IC_{50}$'s reflect the inhibitory potency of the compounds in the new melanin synthesis that was stimulated by α-MSH.

3. Tyrosine Kinase Assay (TK):

TK assays can be performed using purified tyrosine kinase domains of c-met, erb-B2, or IGF-r. A specific antibody against phosphorylated tyrosine residue is used in the assay. Colorimetric signals are generated by horse radish peroxidase, which is conjugated to the antibody.

4. Human Skin Equivalent Model:

A mixture of human melanocytes and keratinocytes is grown in an air-liquid interphase. This tissue culture forms a three dimensional structure that histologically and microscopically resembles the human skin epidermis. Test compounds are added on top of the cells to mimic topical drug application. After incubation with the compounds (10 µM) for 3 days, the cells are washed extensively and lysed for DOPA oxidase assay.

5. IL-1 Assay (Interleukin-1 Assay):

An IL-1α ELISA assay (R&D system) can be used to evaluate the effect of compounds on IL-1 secretion in a human skin equivalent model. IL-1α is a pro-inflammatory cytokine and plays a role in UV-induced skin inflammation.

6. In vivo Study:

Black or dark brown guinea pigs with homogeneous skin color can be used in this study. A solution of the test compound of formula I (5% in ethanol:propylene glycol, 70:30) and the vehicle control are applied to the animals twice daily, 5 days per week for 4–8 weeks. Using this assay, depigmentation can be determined by subtracting the light reflectance of untreated skin from the light reflectance of treated skin.

The present invention is illustrated by the following examples. It will be understood, however, that the invention is not limited to the specific details of these examples. Melting points are uncorrected. Proton nuclear magnetic resonance spectra (400 MHz $^1$H NMR) were measured for solutions in $d_6$-DMSO, $CDCl_3$, or $d_4$-MeOH, and peak positions are expressed in parts per million (ppm) downfield from tetramethylsilane (TMS). The peak shapes are denoted as follows: s, singlet; d, doublet; t, triplet; q, quartet, m, multiplet, b, broad.

The following examples are illustrative only, and are not intended to limit the scope of the present invention.

EXAMPLES

Intermediate 1

1-Bromo-2,4-bis(methoxymethoxy)benzene

An oven dried 250 ml round bottomed flask equipped with magnetic stirrer, under an argon atmosphere, was loaded with 4-bromoresorcinol (9.45 g, 50 mmol) and $CH_2Cl_2$ (50 ml). The stirred suspension was cooled to 0° C. and diisopropylamine (19.1 ml, 110 mmol) was added in one portion via syringe. Stirring of the red solution was continued for a further ten minutes before methyl chloromethyl ether (10.7 ml, 120 mmol) was added dropwise, via syringe, ensuring the internal temperature did not exceed 10° C. The resulting yellow solution was then allowed to warm to room temperature overnight. Ammonium hydroxide solution (50 mL, 50%) was poured into the reaction vessel and stirring was continued for one hr. The mixture was poured into a separating funnel and the phases separated. The aqueous phase was then extracted with $CH_2Cl_2$ (3×30 ml) and the combined organics washed with brine (20 ml), dried over anhydrous magnesium sulphate, filtered and concentrated in vacuo affording an orange oil. Purification was achieved by flash column chromatography, ($SiO_2$, ethyl acetate/petroleum ether, 1:1, v/v), furnishing the title product (10.7 g, 77%) as a pale yellow oil. $\delta_H(CDCl_3)$ 7.42 (1H, d), 6.88 (1H, d), 6.64 (1H, dd), 5.24 (2H, s), 5.15 (2H, s), 3.53 (3H, s), 3.48 (3H, s).

Intermediate 2

8-[2,4-Bis(methoxymethoxy)phenyl]-1,4-dioxaspiror[4.5]decan-8-ol

A round bottomed flask, equipped with magnetic stirrer, under an argon atmosphere was loaded with 1-bromo-2,4-bis(methoxymethoxy)benzene (2.00 g, 7.2 mmol) and THF (50 mL). N,N,N',N'-Tetramethylethylene diamine (2.3 ml, 15.2 mmol) was added in one portion via syringe and the stirred solution was cooled to −78° C. n-Butyl lithium (9.5 ml, 15.2 mmol, 1.6M in hexane) was added dropwise via syringe. The resulting yellow solution was stirred for 1 hr at −78° C. and 1,4-cyclohexanedione monoethylene ketal (1.35 g, 8.7 mmol) was added as a solution in THF (25 ml) slowly, via syringe. The resulting solution was stirred at −78° C. for 1 hr and then allowed to warm to room temperature overnight. Hydrochloric acid (20 ml, 2M) was added and the reaction mixture stirred vigorously for 15 min. Ethyl acetate (100 ml) was added and the mixture poured into a separating funnel. The phases were separated and the aqueous phase was extracted with ethyl acetate (3×20 ml). The combined organics were washed with brine (20 ml), dried over anhydrous magnesium sulphate, filtered and concentrated affording an orange oil which was purified by flash column chromatography ($SiO_2$, ethyl acetate/petroleum ether, 45:55, v/v). The title product (1.42 g, 56%) was isolated as a colourless oil. m/z (ES$^+$) 337 (M−H$_2$O+H$^+$); $\delta_H(CDCl_3)$ 1.61–1.64(2H, m), 2.00–2.18(6H, m), 3.44(3H, s), 3.48(3H, s), 3.90–3.97(4H, m), 5.11(2H, s), 5.24(2H, s), 6.64(1H, dd), 6.82(1H, d), 7.20(1H, d).

Intermediate 3

8-[2,4-Bis(methoxymethoxy)phenyl]-1,4-dioxaspiro[4.5]dec-7-ene

8-[2,4-Bis(methoxymethoxy)phenyl]-1,4-dioxaspiro[4.5]decan-8-ol (1.40 g, 3.95 mmol) was placed in a 50 ml round bottomed flask equipped with magnetic stirrer and Dean-Stark apparatus. Toluene (30 ml) was added, followed by camphor sulphonic acid (10 mg). The stirred solution was then heated under reflux for 1 hr, cooled and saturated aqueous sodium bicarbonate solution (10 ml) added. The mixture was poured into a separating funnel and the phases separated. The aqueous phase was extracted with ethyl acetate (2×15 ml) and the combined organics were washed with brine (15 ml), dried over anhydrous magnesium sulphate, filtered and then concentrated in vacuo yielding an orange oil which was purified by flash column chromatography ($SiO_2$, ethyl acetate/petroleum ether, 45:55, v/v) to afford the title product (0.94 g) as a colourless oil. $\delta_H(CDCl_3)$ 1.84 (2H, t), 2.41–2.43 (2H, m), 2.56–2.62 (2H, m), 3.47 (6H, s), 3.98–4.02 (4H, m), 5.13 (4H, s), 5.58–5.63 (1H, m), 6.64 (1H, dd), 6.78 (1H, d), 7.08 (1H, d).

Intermediate 4

8-[2,4-Bis(methoxymethoxy)phenyl]-1,4-dioxaspiro[4.5]decane

8-[2,4-Bis(methoxymethoxy)phenyl]-1,4-dioxaspiro[4.5]dec-7-ene (0.950 g, 2.83 mmol) and palladium (200 mg, 10% on carbon) were stirred under an atmosphere of hydrogen for 15 hr. The mixture was then filtered through a plug of Celite, washing with ethyl acetate. The filtrate was then evaporated to dryness, affording the desired product (0.955 g, 100%) as a colourless oil. $\delta_H(CDCl_3)$ 1.67–1.87 (8H, m), 2.90–2.99 (1H, m), 3.46 (3H, s), 3.48 (3H, s), 3.97 (4H, s), 5.12 (2H, s), 5.18 (2H, s), 6.65 (1H, dd), 6.78 (1H, d), 7.12 (1H, d).

Intermediate 5

4-[2,4-Bis(methoxymethoxy)phenyl]cyclohexanone

A round bottomed flask equipped with magnetic stirrer was charged with 8-[2, 4-bis(methoxymethoxy)phenyl]-1,4- dioxaspiro[4.5]decane (3.20 g 9.47 mmol) and methanol (50 ml). Over a 20 min period, aqueous hydrochloric acid (50 ml, 1.00M) was added to the stirred solution, at room temperature and the reaction mixture stirred for 1.5 hr. Solid sodium bicarbonate was added until the reaction mixture was neutralised and the solvent was removed under reduced pressure. The residue was partitioned between ethyl acetate (30 ml) and water (10 ml), and the aqueous layer was extracted with ethyl acetate (3×20 ml). The combined organic layers were washed with brine (10 ml), dried over magnesium sulfate, filtered and concentrated in vacuo. The crude product was purified via flash column chromatography (SiO$_2$, ethyl acetate/petroleum ether, 1:4, v/v), affording the title compound (2.20 g, 60%) as a white powder. $\delta_H$(CDCl$_3$) 1.85–1.96 (2H, m), 2.14–2.22 (2H, m), 2.46–2.59 (4H, m), 3.39 (1H, tt), 3.49 (3H, s), 3.52 (3H, s), 5.16 (2H, s), 5.23 (2H, s), 6.67–6.71 (1H, m), 6.85 (1H, m), 7.08 (1H, d).

Intermediate 6

3-[2,4-bis(methoxymethoxy) phenyl]-2-cyclohexen-1-one

Aqueous sodium carbonate (2 ml of a 6M solution) and 2,4-bis(methoxymethoxy)phenylboronic acid (120 mg) in ethanol (2 ml) were added to a solution of palladium tetrakis(triphenylphosphine) (57 mg) and 3-bromo-2-cyclohexen-1-one (87 mg) in dimethoxyethane (3 ml) and the mixture was heated under reflux. After 6 hr, the mixture was partitioned between water (50 ml) and ethyl acetate (100 ml). The organic layer was dried over magnesium sulfate and evaporated in vacuo to furnish an oil that was purified by flash column chromatography (SiO$_2$, ethyl acetate/petroleum ether, 1:3, v/v) to furnish the title compound as an oil (120 mg, 83%). $\delta_H$(CDCl$_3$) 2.10 (2H, quintet), 2.47 (2H, t), 2.74 (2H, m), 3.476 (3H, s), 3.484 (3H, s), 5.185 (2H, s), 5.190 (2H, s), 6.21 (1H, m), 6.71 (1H, dd), 6.85 (1H, d), 7.16 (1H, d).

Intermediate 7

(±)-3-[2,4-Bis(methoxymethoxy)phenyl] cyclohexanone

A suspension of 3-[2,4-bis(methoxymethoxy)phenyl]-2-cyclohexen-1-one (300 m g) and palladium catalyst (50 mg, 10% palladium on carbon) in ethanol was stirred at ambient temperature under 1 atmosphere of hydrogen. After 16 hr, the mixture was filtered through celite and the filtrate was evaporated in vacuo. The product was dissolved in dichloromethane (15 ml). Celite and pyridinium chlorochromate (430 mg) were added and the mixture was stirred at room temperature. After 3 hr, the mixture was filtered through a pad of silica and eluted with petroleum ether/ethyl acetate (10:3, v/v), then purified by flash column chromatography (SiO$_2$, petroleum ether/ethyl acetate 4:1 v/v) to furnish the title compound as an oil (200 mg, 70%). $\delta_H$(CDCl$_3$) 1.7–1.9 (2H, overlapping m), 2.05 (1H, m), 2.15 (1H, m), 2.35–2.60 (4H, overlapping m), 3.37 (1H, m), 3.490 (3H, s), 3.492 (3H, s), 5.15 (2H, s), 5.20 (2H, s), 6.70 (1H, dd), 6.82 (1H, d), 7.09 (1H, d).

Intermediate 8

3-(2,4-Dimethoxymethoxyphenyl)-2-cyclohexen-1-one Oxime

3-[2,4-Bis(methoxymethoxy)phenyl]-2-cyclohexen-1-one (200 mg), hydroxylamine hydrochloride (72 mg) and triethylamine (0.14 ml) were heated under reflux in ethanol (10 ml). After 3 hr, the cooled reaction mixture was partitioned between water and ethyl acetate. The organic layer was dried over magnesium sulfate and evaporated in vacuo to furnish the title compound as an oil (206 mg, 99%). m/z (ES$^+$) 308 (M+H)$^+$.

Intermediate 9

(±)-1-{3-[2,4-Bis(methoxymethoxy)phenyl] cyclohexyl}piperazine (±)-3-[2,4-Bis(methoxymethoxy)phenyl]cyclohexanone (80 mg) and piperazine (24 mg) were dissolved in dichloroethane (5 ml) and stirred at ambient temperature for 1 hr under argon. Tetramethylammonium triacetoxyborohydride (79 mg) was added and stirring continued under argon. After 16 hr, additional portions of piperazine (24 mg) and tetramethylammonium triacetoxyborohydride (79 mg) were added and stirring continued. After a further 6 hr, glacial acetic acid was added dropwise until a solution was obtained, and stirring continued at ambient temperature. After a further 16 hr, the reaction mixture was partitioned between sodium hydrogen carbonate (20 ml of a saturated solution) and ethyl acetate. The aqueous layer was extracted with ethyl acetate (3×20 ml), and the combined organic extracts were dried over magnesium sulfate and evaporated in vacuo. The crude residue was purified by flash column chromatography chromatography (SiO$_2$, dichloromethane/methanol, 9:1 v/v) to furnish the title compound as an off white solid (52 mg, 53%) and mixture of diastereoisomers; m/z (ES$^+$) 365 (M+H)$^+$.

Intermediate 10

(±)-3-[2,4-Bis(methoxymethoxy)phenyl] cyclohexylamine

Nickel chloride hexahydrate (77 mg) and sodium borohydride (24 mg) were added to a stirred solution of (±)-3-[2,4-bis(methoxymethoxy)phenyl]cyclohexanone oxime (50 mg) in methanol (2 ml). After 0.5 hr, water was added until effervescence ceased, the reaction mixture was filtered, and the residue was washed thoroughly with methanol. The combined filtrate and washings were evaporated in vacuo and the crude residue was purified by flash column chromatography (SiO$_2$, dichloromethane/methanol, 9:1 v/v) to furnish the title compound as a colourless oil (31 mg, 65%) and a mixture of diastereoisomers; m/z (ES$^+$) 295 (M+H)$^+$.

Intermediate 11

(±)-N-{3-[2,4-Bis(methoxymethoxy)phenyl] cyclohexyl}methanesulfonamide

Triethylamine (0.014 ml) and methanesulfonyl chloride (8 µl) were added to a solution of (±)-3-[2,4-bis (methoxymethoxy)phenyl]cyclohexylamine (27 mg) in dichloromethane (1 ml), and the mixture was stirred under argon at ambient temperature. After 1 hr, the mixture was partitioned between ethyl acetate (20 ml) and sodium hydrogen carbonate (20 ml of a saturated aqueous solution). The aqueous layer was extracted with ethyl acetate (2×20 ml), and the combined organic extracts were dried over magnesium sulfate and evaporated in vacuo to furnish the title compound as an oil and a mixture of diastereoisomers; m/z (ES$^+$) 374 (M+H)$^+$.

Intermediate 12

(±)-2,4-Bis(methoxymethoxy)-1-(3-methylenecyclohexyl)benzene

Potassium tert-butoxide (50 mg) was added to a suspension of methyltriphenylphosphonium bromide in tetrahydrofuran (4 ml) at 0° C. After 0.5 hr, a solution of (±)-3-[2,4-bis(methoxymethoxy)phenyl]cyclohexanone (100 mg) in tetrahydrofuran (1 ml) was added, and the mixture was allowed to warm to ambient temperature. After 16 hr, the reaction mixture was partitioned between ammonium chloride (30 ml of a saturated aqueous solution) and ethyl acetate. The aqueous layer was extracted with further ethyl acetate (2×30 ml), and the combined organic extracts were washed with brine (30 ml), dried over magnesium sulfate, and evaporated in vacuo. The crude residue was purified by flash column chromatography (SiO$_2$, ethyl acetate/petrol, 4:1 v/v) to furnish the title compound as pale yellow oil (80 mg, 81%). $\delta_H$(CDCl$_3$) 1.50 (2H, m), 1.90 (2H, m), 2.05 (1H, m), 2.16 (1H, m), 2.35 (1H, m), 2.44 (1H, m), 2.97 (1H, m), 3.44 (3H, s), 3.48 (3H, s), 4.64 (1H, s), 4.69 (1H, s), 5.13 (2H, s), 5.17 (2H, s), 6.68 (1H, m), 6.77 (1H, m), 7.12 (1H, d).

Intermediate 13

(±)-{3-[2,4-Bis(methoxymethoxy)phenyl]cyclohexyl}methanol

9-Borabicyclononane (2.7 ml of a 0.5M solution in tetrahydrofuran) was added to a stirred solution of (±)-2,4-bis(methoxymethoxy)-1-(3-methylenecyclohexyl)benzene (80 mg) in tetrahydrofuran (2 ml) at 0° C. under argon. After 1 hr at 0° C., the reaction mixture was allowed to warm to ambient temperature and stirring continued. After 2 hr, the reaction mixture was cooled to 0° C. and water (0.1 ml) was added. After the effervescence had subsided, hydrogen peroxide (1 ml of a 30% w/v solution) and sodium hydroxide (1 ml of a 2M solution) were added and the mixture was allowed to warm to ambient temperature. After a further 16 hr, the reaction mixture was cooled to 0° C. Saturated aqueous sodium metabisulfite was added until no oxidant could be detected by starch iodide paper, and the reaction mixture was extracted with ethyl acetate (3×30 ml). The combined organic extracts were washed with water (20 ml), dried over magnesium sulfate, and evaporated in vacuo. The crude residue was purified by flash column chromatography (SiO$_2$, ethyl acetate/petrol, 1:1 v/v) to furnish the title compound as a pale brown oil (46 mg, 54%); m/z (ES$^+$) 311 (M+H)$^+$.

Intermediate 14

(±)-3-[2,4-Bis(methoxymethoxy)phenyl]cyclohexanone Oxime

Hydroxylamine hydrochloride (71 mg), triethylamine (0.17 ml) and (±)-3-[2,4-bis(methoxymethoxy)phenyl]cyclohexanone (200 mg) were heated under reflux in ethanol (8 ml). After 0.75 hr, the reaction mixture was evaporated in vacuo and the residue was partitioned between ethyl acetate (100 ml) and water (100 ml). The aqueous layer was extracted with ethyl acetate (2×100 ml), and the combined organic extracts were dried over magnesium sulfate and evaporated in vacuo. The crude residue was purified by flash column chromatography (SiO$_2$, ethyl acetate/petrol, 1:1 v/v) to furnish the title compound as a pale yellow oil (197 mg, 94%); m/z (ES$^+$) 310 (M+H)$^+$.

Intermediate 15

(±)-N-{3-[2,4-Bis(methoxymethoxy) phenyl]cyclohexyl}hydroxylamine

Borane (0.412 ml of a 1M solution in tetrahydrofuran) was added to a stirred solution of (±)-3-[2,4-bis(methoxymethoxy)phenyl]cyclohexanone oxime (85 mg) in tetrahydrofuran (2 ml) at 0° C. under argon. After 2 hr, acetic acid (1 ml) was added and the mixture was allowed to warm to ambient temperature. After 16 hr, sodium hydrogen carbonate (20 ml of a saturated aqueous solution) was added, the mixture was extracted with ethyl acetate (3×20 ml) and the combined organic extracts were dried over magnesium sulfate and evaporated in vacuo. The crude residue was purified by flash column chromatography (SiO$_2$, dichloromethane/methanol, 9:1 v/v) to furnish two compounds as clear gums which were identified as diastereoisomers of the title compound; trans-isomer (12 mg, 14%) m/z (ES$^+$) 312 (M+H)$^+$; cis-isomer (0.017 g, 20%) m/z (ES$^+$) 312 (M+H)$^+$.

Intermediate 16

4-(2,4-Bis{[tert-butyl(dimethyl)silyl]oxy}phenyl)cyclohexanone 4-(2,4-Dihydroxyphenyl)cyclohexanone (400 mg) was dissolved in dimethyl formamide (3 ml) with stirring. tert-Butyldimethylsilyl chloride (704 mg), imidazole (660 mg) and 4-dimethylaminopyridine (3 mg) were added sequentially. After 4 hr, the solvent was removed in vacuo and the residue partitioned between ethyl acetate (20 ml) and water (5 ml). The aqueous phase was extracted with ethyl acetate (2×10 ml), and the combined organic phases were washed with brine (10 ml), dried over anhydrous magnesium sulphate, and concentrated under reduced pressure to give a brown oil. Purification via flash column chromatography (SiO$_2$ eluting with ethyl acetate/petroleum ether, 1:9 v/v) furnished the title compound as white flakes (750 mg, 89%). $\delta_H$(CDCl$_3$): 0.18 (6H, s), 0.20 (6H, s), 0.97 (9H, s), 1.03 (9H, s), 1.72–1.87 (2H, m), 2.15–2.17 (2H, m), 2.42–2.48 (4H, m), 3.33 (1H, tt), 6.32 (1H, d), 6.39 (1H, dd), 6.94 (1H, d); m/z (ES$^+$) 435 (M+1)$^+$.

Intermediate 17 tert-Butyl [3-{[tert-butyl(dimethyl)silyl]oxy}-4-(4-methylenecyclohexyl)phenoxy]dimethyl Silane To a stirred suspension of methyltriphenylphosphonium bromide (329 mg) in anhydrous THF (10 ml) at 0° C. was added potassium tert-butoxide (103 mg) in one portion. After stirring for 30 min, a solution of 4-(2,4-bis{[tert-butyl(dimethyl)silyl]oxy}phenyl) cyclohexanone (200 mg) in THF (5 ml) was added. The reaction mixture was stirred for a further 30 min at 0° C., and saturated aqueous ammonium chloride solution (20 ml) was added. The layers were separated and the aqueous layer extracted with ethyl acetate (3×20 ml). The combined organic phases were washed with brine (20 ml), dried over anhydrous magnesium sulphate, and concentrated in vacuo. Purification via flash column chromatography (SiO$_2$ eluting with diethyl ether:petroleum ether, 1:4 v/v) furnished the title compound as a colourless oil (135 mg, 68%). $\delta_H$(CDCl$_3$): 0.19 (6H, s), 0.24 (6H, s), 0.97 (9H, s), 1.03 (9H, s), 1.41 (2H, dq), 1.84–1.93 (2H, m), 2.16 (2H, dt), 2.33–2.42 (2H, m), 3.01 (1H, tt), 4.66 (2H, s), 6.29 (1H, dd), 6.40 (1H, dd), 6.94 (1H, d).

Intermediate 18 trans/cis-[4-(2,4-Bis{[tert-butyl(dimethyl)silyl]oxy}phenyl)cyclohexyl]methanol tert-Butyl[3-{[tert-butyl(dimethyl)silyl]oxy}-4-(4-methylenecyclohexyl)phenoxy]dimethyl silane (135 mg)

was dissolved in anhydrous THF (5 ml) with stirring and cooled to −78° C. 9-Borabicyclo[3.3.1]nonane (3.13 ml, 0.5M in THF) was added to the stirred solution and the resulting reaction mixture allowed to warm to room temperature over 3 hr and then stirred for 3 days. Cooling to 0° C. was followed by addition of hydrogen peroxide (1 ml, 30% aqueous solution) and sodium hydroxide (1 ml, 2M aqueous solution). The reaction mixture was allowed to warm to room temperature with stirring over 1 hr. cooled to 0° C., and saturated aqueous sodium metabisulphate solution (30 ml) was added. The layers were separated and the aqueous layer extracted with ethyl acetate (3×20 ml). The combined organic phases were washed with brine (20 ml), dried over anhydrous magnesium sulphate, and concentrated in vacuo. Purification via flash column chromatography (SiO$_2$ eluting with petroleum ether:diethyl ether, 3:17 v/v) afforded the desired product as a yellow oil (73 mg, 52%). $\delta_H$(CDCl$_3$): 0.18 (6H, s), 0.22 (6H, s), 0.97 (9H, s), 1.00 (9H, s), 1.03–1.15 (0.5H, m), 1.22–1.33 (0.5H, m), 1.43–1.61 (4H, m), 1.77–1.94 (4H, m), 2.75–2.92 (1H, m), 3.47 (1H, d), 3.70 (1H, d), 6.26–6.29 (1H, m), 6.37–6.40 (1H, m), 6.93–6.97 (1H, m).

Intermediate 19 trans/cis-4-(2,4-Bis{[tert-butyl(dimethyl)silyl] oxy}phenyl)-1-methylcyclohexanol 4-(2,4-Bis(tert-butyldimethylsilyloxy)) phenylcyclohexanone (50 mg) was dissolved in anhydrous THF (10 ml) and cooled to 0° C. Methylmagnesium chloride (59 ml, 22% w/v in THF) was added dropwise and the reaction mixture allowed to warm to room temperature with stirring over 2 days. The reaction mixture was partitioned between aqueous HCl (10 ml, 0.5M) and ethyl acetate (10 ml). The aqueous phase was extracted with ethyl acetate (2×10 ml) and the combined organic phases were washed with saturated aqueous sodium bicarbonate solution (10 ml), brine (10 ml), and then dried over anhydrous magnesium sulphate. Removal of the solvent under reduced pressure afforded an oil which was purified via flash column chromatography (SiO$_2$ eluting with ethyl acetate:petroleum ether, 1:4 v/v) affording the title compound as a white solid and a mixture of diastereoisomers (29 mg, 56%). $\delta_H$(CDCl$_3$): 0.19 (6H, s), 0.23 (6H, s), 0.97 (9H, s), 1.02 (9H, s), 1.26 (1.5H, s), 1.32 (1.5H, s), 1.36–1.82 (8H, m), 2.73–2.91 (1H, m), 6.29–6.31 (1H, m), 6.39–6.42 (1H, m), 6.80 (0.5H, d), 7.20 (0.5H, d).

Intermediate 20 trans/cis-4-(2,4-Bis{[tert-butyl(dimethyl)silyl] oxy}phenyl)cyclohexylamine

4-[2,4-Bis(tert-butyldimethylsilyloxy)phenyl] cyclohexanone oxime (120 mg) was dissolved in anhydrous methanol (10 ml) with stirring. The solution was cooled to −40° C., and nickel chloride hexahydrate (133 mg) was added. Stirring was continued for 10 min before sodium borohydride (42 mg) was added in one portion. The reaction mixture was stirred at −40° C. for 20 min and water (0.5 ml) was added. The reaction mixture was allowed to warm to room temperature with stirring. Silica gel was added and the solvent removed in vacuo. Purification via flash column chromatography (SiO$_2$ eluting with CH$_2$Cl$_2$:MeOH:NH$_4$OH, 44:50:6 v/v) afforded the desired product as a pale brown oil (83 mg, 71%) and a mixture of diastereoisomers. $\delta_H$(CD$_3$OD): 0.22 (6H, s), 0.27 (6H, s), 1.02 (9H, s), 1.08 (9H, s), 1.24–1.40 (1H, m), 1.42–1.57 (1H, m), 1.57–1.68 (1H, m), 1.71–1.90 (4H, m), 1.99–2.07 (1H, m), 2.84–2.98 (1H, m), 4.28–4.40 (1H, m), 6.34 (1H, d), 6.44 (1H, t), 7.04 (0.5H, d), 7.16 (0.5H, d); m/z (ES$^+$) 436 (M+1)$^+$.

Intermediate 21 trans/cis-N-[4-(2,4-Bis{[tert-butyl(dimethyl)silyl] oxy}phenyl)cyclohexyl]acetamide trans/cis-4-(2,4-Bis{[tert-butyl(dimethyl)silyl] oxy}phenyl)cyclohexylamine (27 mg) was dissolved in pyridine (0.5 ml). Acetyl chloride (6 μl) and 4-dimethylaminopyridine (2 mg) were added sequentially and the reaction mixture stirred for 24 hr. The solvent was removed in vacuo and the residue partitioned between ethyl acetate (10 ml) and water (2 ml). The aqueous phase was extracted with ethyl acetate (2×5 ml) and the combined organic phases were washed with brine (10 ml), dried over anhydrous magnesium sulphate, and concentrated to give a brown oil. Purification via flash column chromatography (SiO$_2$ eluting with ethyl acetate:petroleum ether, 7:3 v/v) afforded the title product as a white solid (15 mg, 50%) and a mixture of diastereoisomers. $\delta_H$(CDCl$_3$): 0.17 (3H, s), 0.19 (3H, s), 0.21 (3H, s), 0.22 (3H, s), 0.96 (9H, s), 1.02 (9H, s), 1.06–1.20 (2H, m), 1.36–1.54 (2H, m), 1.60–1.75 (2H, m), 1.80–1.92 (2H, m), 1.95 (1.5H, s), 2.00 (1.5H, s), 2.75–2.90 (1H, m), 3.76–3.87 (1H, m), 5.34–5.39 (0.5H, d), 5.72–5.77 (0.5H, d), 6.26–6.29 (1H, m), 6.38–6.41 (1H, m), 6.93 (0.5H, d), 6.95 (0.5H, d); m/z (ES$^+$) 478 (M+1)$^+$.

Intermediate 22

3-[2,4-Bis(methoxymethoxy)phenyl]-2-cyclopenten-1-one 1,3-Bis(methoxymethoxy)-4-bromobenzene (1.0 g) was dissolved in THF (20 ml) and cooled to −78° C. under argon. N,N,N',N'-Tetramethylethylene diamine was added followed by dropwise addition of n-BuLi (3.4 ml of a 2.2M solution in hexanes) over 10 mins. After stirring at −78° C. for 1 hr, a solution of 3-methoxy-2-cyclopentene-1-one (605 mg) in THF (5 ml) was added slowly. The reaction mixture was stirred at −78° C. for 1 hr before warming to 0° C. 1 M HCl (20 ml) was added, and after 10 min the mixture was extracted with ethyl acetate (2×50 ml). The combined organic phases were washed with brine (30 ml), dried over magnesium sulfate, and concentrated in vacuo. The crude residue was purified by flash column chromatography (SiO$_2$, ethyl acetate/petrol, 1:1 v/v) to furnish the title compound as yellow oil (128 mg, 13%); m/z (ES$^+$) 279 (M+1)$^+$.

Intermediate 23

(±)-3-[2,4-Bis(methoxymethoxy)phenyl] cyclopentanone

3-[2,4-Bis(methoxymethoxy)phenyl]-2-cyclopenten-1-one (50 mg) and palladium (10 mg, 10% on carbon) were stirred under an atmosphere of hydrogen for 15 hr. The mixture was then filtered through a plug of Celite, washing with ethyl acetate, and the filtrate was concentrated in vacuo. The residue was purified by flash column chromatography (SiO$_2$, ethyl acetate/petrol, 1:1 v/v) to furnish the title compound as a colourless oil (8 mg, 16%); m/z (ES$^+$) 583 (2M+Na)$^+$.

Intermediate 24

3-(Benzyloxy)-2-cyclohexen-1-one

To a round bottomed flask equipped with magnetic stirrer and Dean-Stark apparatus was added 1,3-cyclohexanedione (60.0 g, 535 mmol), toluene (450 ml), p-toluenesulfonic acid monohydrate (1.35 g, 5.20 mmol) and benzyl alcohol (52.6 g, 487 mmol). The resulting solution was heated to reflux temperature for 12 hr. The reaction mixture was cooled to room temperature and then washed with saturated aqueous sodium carbonate solution (2×100 ml). The organic layer was then washed with brine (100 ml), dried over magnesium sulfate, filtered and concentrated in vacuo, affording a brown oil (94.9 g) which crystallised upon standing for 17 hr. The crude crystalline material was slurried in isopropyl ether (20 ml). The mixture was filtered and the crystalline material was washed with ice cold isopropyl ether (3×30 ml), then with cold petroleum ether (2×20 ml). The resulting peach coloured crystalline solid was dried overnight under reduced pressure, furnishing the desired product (74.4 g, 76%). m/z (ES$^+$) 203 (M+H$^+$).

Intermediate 25

(±)-3-(Benzyloxy)-6-(8-hydroxy-1,4-dioxaspiro[4.5] dec-8-yl)-2-cyclohexen-1-one

To a round bottomed flask equipped with magnetic stirrer was added anhydrous tetrahydrofuran (600 ml) and diisopropylamine (38.1 ml, 272 mmol). The stirred solution was cooled to −78° C. and n-butyl lithium (113.4 ml, 272 mmol, 2.4M in cyclohexanes) was added dropwise via syringe in 20 ml portions. The resulting yellow solution was stirred for 35 min at −78° C., then 3-(benzyloxy)-2-cyclohexen-1-one (50.0 g, 248 mmol) was added as a solution in anhydrous tetrahydrofuran (100 ml). The solution was stirred for 1 hr prior to the addition of cyclohexane-1,4-dione monoethylene ketal (38.7 g, 248 mmol) as a solution in anhydrous tetrahydrofuran (100 ml). The solution was stirred for 2 hr at −78° C., then allowed to warm slowly to room temperature over 1 hr. Saturated aqueous ammonium chloride (80 ml) was added, followed by dichloromethane (700 ml), and the mixture was stirred until no solids remained. The layers were separated and the aqueous phase extracted with dichloromethane (2×100 ml). The combined organic layers were washed with brine (50 ml), dried over magnesium sulfate, then concentrated in vacuo. Trituration of the resulting solid with methanol afforded the title compound (78.4 g, 88%). m/z (ES$^+$) 359 (M+H$^+$).

Intermediate 26

(±)-1-(Benzyloxy)-6-bromo-3-(1,4-dioxaspiro[4.5] dec-8-yl)-2-oxabicyclo [2.2.2]octan-5-one A round bottomed flask equipped with magnetic stirrer was charged with (±)-3-(benzyloxy)-6-(8-hydroxy-1,4-dioxaspiro[4.5]dec-8-yl)-2-cyclohexen-1-one (78.4 g, 219 mmol) and dichloromethane (600 ml). To the stirred solution was added N-bromosuccinimide (40.9 g, 230 mmol) in one portion, followed by aqueous hydrobromic acid (3 drops, 48% solution) when no more solid remained. The resulting solution was stirred at room temperature for 2 hr then poured into a separating funnel containing aqueous sodium metabisulfite solution (150 ml) and dichloromethane (200 ml), then the funnel was shaken vigorously. The layers were separated and the organic layer was washed with brine (200 ml), dried over magnesium sulfate, filtered, then concentrated in vacuo to give a solid. Trituration with methanol (500 ml) afforded the desired compound (82.8 g, 86%) as a white solid. m/z (ES$^+$) 437 and 439 [(1:1), M+H$^+$].

Intermediate 27

5-(Benzyloxy)-2-(1,4-dioxaspiro[4.5]dec-7-en-8-yl) phenol

A round bottomed flask was charged with (±)-1-(benzyloxy)-6-bromo-3-(1,4-dioxaspiro[4.5]dec-8-yl)-2-oxabicyclo[2.2.2]octan-5-one (13.8 g, 31.6 mmol) and anhydrous N,N-dimethylformamide (140 ml). To the stirred solution was added 1,8-diazabicyclo[5.4.0]undec-7-ene (9.92 ml, 66.3 mmol) in one portion. The solution turned dark brown in colour immediately and was then heated to 140° C. for 12 hr with vigorous stirring. The reaction mixture was allowed to cool to room temperature and most of the solvent was removed under reduced pressure. The remaining oil was partitioned between ethyl acetate (200 ml) and water (100 ml), then the layers were separated and the aqueous phase was extracted with ethyl acetate (3×50 ml). The combined organic layers were back extracted with water (3×30 ml) to remove any residual N,N-dimethylformamide. The organic phase was washed with brine (20 ml), dried over magnesium sulfate, filtered and concentrated in vacuo to afford a brown oily solid, which was adsorbed onto silica gel. Purification via flash column chromatography (SiO$_2$, ethyl acetate/petroleum ether, 1:1, v/v) furnished the desired product (7.1 g, 66%) as a white solid. m/z (ES$^+$) 339(M+H$^+$).

Intermediate 28

4-(1,4-Dioxaspiro[4.5]dec-8-yl)-1,3-benzenediol

A round bottomed flask with magnetic stirrer was charged with 5-(benzyloxy)-2-(1,4-dioxaspiro[4.5]dec-7-en-8-yl)phenol (6.90 g, 20.4 mmol), ethanol (300 ml) and palladium (2.00 g, 10% on activated carbon). The reaction vessel was then evacuated and placed under a hydrogen atmosphere. This process was repeated 15 times before stirring vigorously for 64 hr under a hydrogen atmosphere. The reaction mixture was filtered through a celite plug, washing with ethyl acetate. The filtrate was concentrated in vacuo, furnishing the title compound (5.10 g, 100%) as a solid. m/z(ES$^+$) 251(M+H$^+$).

Intermediate 29 cis-N-Benzyl-N-[4-(2,4-bis{[tert-butyl(dimethyl) silyl]oxy}phenyl)cyclohexyl]amine To a round bottomed flask equipped with magnetic stirrer was loaded 4-(2,4-bis{[tert-butyl(dimethyl)silyl] oxy}phenyl)cyclohexanone (3.20 g, 7.36 mmol). Anhydrous 1,2-dichloroethane (85 ml) was added, and to the stirred solution was added benzylamine (0.97 ml, 8.83 mmol) as a solution in 1,2-dichloroethane (20 ml). Activated powdered 4 Å molecular sieves (5.80 g) were added and the reaction mixture stirred vigorously for 2.5 hr. Tetramethylammoniumtriacetoxyborohydride (2.90 g, 11.0 mmol) was added in one portion and the reaction mixture stirred for 64 hr at room temperature. Aqueous sodium hydroxide solution (30 ml, 0.4M) was added and vigorous stirring was continued for 0.5 hr. The reaction mixture was then filtered through celite, washing with dichloromethane (100 ml). The layers were separated and the aqueous layer was extracted with dichloromethane (2×50 ml). The combined organic phases were washed with brine (100 ml), dried over magnesium sulfate, filtered and concentrated in vacuo affording the crude product. Purification via flash column chromatography (SiO$_2$, ethyl acetate/petroleum ether, gradient elution using 1:9, 1:4, then 3:7 v/v) furnished the title product (2.69 g, 70%) as a pale yellow oil. δ$_H$(CDCl$_3$) 0.01 (6H, s), 0.05 (6H, s), 0.77 (9H, s), 0.83 (9H, s), 1.31 (1H, br), 1.39 (4H, m), 1.52 (2H, m), 1.70 (2H, m), 2.69 (1H, m), 2.75 (1H, m), 6.10 (1H, d), 6.23 (1H, dd), 6.84 (1H, d), 7.15 (5H, m).

Intermediate 30

N-Benzyl-N-[4-(2,4-bis{[tert-butyl(dimethyl)silyl] oxy}phenyl) cyclohexylidene]amine To a round bottomed flask equipped with magnetic stirrer was added 4-(2,4-bis{[tert-butyl(dimethyl)silyl]

oxy}phenyl)cyclohexanone (817 mg, 1.88 mmol). Anhydrous dichloromethane (50 ml) was added followed by benzylamine (0.82 ml, 7.52 mmol) and activated 4 Å molecular sieves (10.0 g). The reaction mixture was stirred vigorously for 15 hr, then dichloromethane (50 ml) was added and the reaction mixture filtered through celite, washing with dichloromethane (50 ml). The filtrate was concentrated in vacuo affording the desired product (1.00 g, 86%) as a yellow oil. $\delta_H$(CDCl$_3$) 0.19 (6H, s), 0.26 (6H, s), 0.98 (9H, s), 1.03 (9H, s), 1.51 (1H, m), 1.72 (1H, m), 2.03 (2H, m), 2.45 (1H, m), 2.60 (1H, m), 3.04 (1H, m), 3.22 (1H, m), 4.55 (1H, d), 4.60 (1H, d), 6.31 (1H, d), 6.41 (1H, dd), 6.93 (1H, d), 7.33 (5H, m).

Intermediate 31 trans-N-Benzyl-N-[4-(2,4-bis{[tert-butyl(dimethyl)silyl]oxy} phenyl) cyclohexyl]amine To a round bottomed flask equipped with magnetic stirrer was added N-benzyl-N-[4-(2,4-bis{[tert-butyl(dimethyl)silyl]oxy}phenyl)cyclohexylidene]amine (4.00 g, 7.63 mmol) and anhydrous tetrahydrofuran (480 ml) followed by anhydrous methanol (120 ml). To the solution was added sodium borohydride (1.16 g, 30.5 mmol) and the reaction mixture stirred for 17 hr. The reaction mixture was then diluted with diethyl ether (600 ml) and aqueous sodium hydroxide (400 ml, 0.4M) was added. After stirring for 10 min, the layers were separated and the aqueous layer extracted with dichloromethane (3×100 ml). The combined organic phases were washed with brine (50 ml), dried over magnesium sulfate and concentrated in vacuo to give a yellow oil. Purification via flash column chromatography (SiO$_2$, ethyl acetate/petroleum ether, gradient elution using 1:9, 1:4, then 3:7, v/v) furnished the desired product as a cream coloured solid (2.09 g, 54%). $\delta_H$(CDCl$_3$) 0.01 (6H, s), 0.05 (6H, s), 0.80 (9H, s), 0.85 (9H, s), 1.18 (4H, m), 1.66 (2H, m), 1.87 (2H, m), 2.19 (1H, m), 2.68 (1H, M), 6.12 (1H, d), 6.23 (1H, dd), 6.77 (1H, d), 7.17 (5H, m).

Intermediate 32 trans-4-(2,4-Bis{[tert-butyl(dimethyl)silyl]oxy}phenyl)cyclohexylamine

To a round bottom flask was added trans-N-benzyl-N-[4-(2,4-bis{[tert-butyl(dimethyl)silyl]oxy} phenyl) cyclohexyl]amine (500 mg, 0.95 mmol) and ethanol (20 ml). To the stirred solution was added palladium (10% w/w on activated carbon, 200 mg, 0.19 mmol) as a slurry in ethanol (5 ml). The reaction vessel was evacuated, then placed under hydrogen (10 cycles). The reaction mixture was stirred vigorously under an atmosphere of hydrogen for 18 hr, then filtered through a celite plug, washing with methanol (100 ml). The solvent was removed in vacuo affording the desired product (402 mg, 97%) as a colourless oil. $\delta_H$(CDCl$_3$) 0.01 (6H, s), 0.05 (6H, s), 0.78 (9H, s), 0.82 (9H, s), 1.08 (2H, m), 1.21 (2H, m), 1.62 (2H, m), 1.78 (2H, m), 2.59 (2H, m), 6.11 (1H, d), 6.22 (1H, dd), 6.78 (1H, d).

Intermediate 33 cis-4-(2,4-bis{[tert-butyl(dimethyl)silyl]oxy}phenyl)cyclohexylamine

To a round bottom flask equipped with magnetic stirrer was added cis-N-benzyl-N-[4-(2,4-bis{[tert-butyl(dimethyl)silyl]oxy}phenyl)cyclohexyl]amine (700 mg, 1.33 mmol) and ethanol (30 ml). To the stirred solution was added palladium (10% w/w on activated carbon, 283 mg, 0.27 mmol) as a slurry in ethanol (5 ml). The reaction vessel was evacuated then placed under hydrogen (10 cycles). The reaction mixture was stirred vigorously under an atmosphere of hydrogen for 18 hr then filtered through a celite plug, washing with methanol (100 ml). The solvent was removed in vacuo affording the desired product (561 mg, 97%) as a colourless oil. $\delta_H$(CDCl$_3$) 0.01 (6H, s), 0.04 (6H, s), 0.78 (9H, s), 0.83 (9H, s), 1.21–1.55 (10H, m), 2.64 (1H, m), 3.05 (1H, m), 6.11 (1H, d), 6.22 (1H, dd), 6.84 (1H, d).

Intermediate 34 cis-N-[4-(2,4-Bis{[tert-butyl(dimethyl)silyl]oxy}phenyl)cyclohexyl] Methane Sulfonamide A round bottomed flask equipped with magnetic stirrer was charged with cis-4-(2,4-bis{[tert-butyl(dimethyl)silyl]oxy}phenyl)cyclohexylamine (47 mg, 0.108 mmol) and 1,2-dichloroethane (4 ml). To the stirred solution was added methanesulfonyl chloride (10 µl, 0.12 mmol), triethylamine (30 µl, 0.22 mmol) and 4-dimethylaminopyridine (catalytic amount). The solution was stirred for 17 hr then partitioned between aqueous sodium hydroxide (5 ml, 0.2M) and dichloromethane (5 ml). The aqueous phase was extracted with dichloromethane (2×5 ml) and the combined organic layers were washed with brine (8 ml), dried over magnesium sulfate and concentrated in vacuo. The crude product was adsorbed onto silica gel and purified via flash column chromatography (SiO$_2$, ethyl acetate/petroleum ether, gradient elution using 1:9, 1:4, then 1:3, v/v) to give the title compound (39 mg, 70%) which solidified on standing. $\delta_H$(CDCl$_3$) 0.17 (6H, s), 0.23 (6H, s), 0.97 (9H, s), 1.00 (9H, s), 1.53 (2H, m), 1.71 (4H, m), 1.94 (2H, m), 2.85 (1H, m), 2.99 (3H, s), 3.78 (1H, m), 4.83 (1H, d), 6.28 (1H, d), 6.42 (1H, dd), 6.97 (1H, d).

Intermediate 35 trans-N-[4-(2,4-Bis{[tert-butyl(dimethyl)silyl]oxy}phenyl)cyclohexyl] Methane Sulfonamide To a round bottomed flask equipped with magnetic stirrer was added trans-4-(2,4-bis{[tert-butyl(dimethyl)silyl]oxy}phenyl)cyclohexylamine (248 mg, 0.57 mmol) and 1,2-dichloroethane (25 ml). To the stirred solution was added triethylamine (191 µl, 1.37 mmol) followed by methanesulfonyl chloride (53 µl, 0.68 mmol) and three crystals of 4-dimethylaminopyridine. The resulting solution was stirred at room temperature for 18 hr and then poured into a separating funnel containing dichloromethane (100 ml) and water (20 ml). The layers were separated and the aqueous phase extracted with dichloromethane (1×50 ml). The combined organic phases were washed with brine (50 ml), dried over magnesium sulfate, filtered and concentrated in vacuo affording the title compound as a pale yellow oil (320 mg, 100%). $\delta_H$(CDCl$_3$) 0.02 (6H, s), 0.05 (6H, s), 0.78 (9H, s), 0.82 (9H, s), 1.22 (4H, m), 1.70 (2H, m), 1.99 (2H, m), 2.61 (1H, m), 2.81 (3H, s), 3.19 (1H, m), 3.92 (1H, d), 6.13 (1H, d), 6.22 (11H, dd), 6.66 (1H, d).

Intermediate 36

4-(4-{[tert-Butyl(dimethyl)silyl]oxy}phenyl)cyclohexanone

To a round bottomed flask equipped with magnetic stirrer was added 4-(4-hydroxy)phenylcyclohexanone (1.00 g, 5.26 mmol) (commercially available from Aldrich) and anhydrous N,N-dimethylformamide (5 ml). To the stirred solution was added imidazole (0.90 g, 13.20 mmol), tert-butyl (dimethyl)silyl chloride (1.19 g, 7.89 mmol) and 4-dimethylaminopyridine (catalytic amount). The reaction mixture was stirred for 17 hr at room temperature and then the N,N-dimethylformamide removed in vacuo. The residue was partitioned between ethyl acetate (100 ml) and water (5 ml). The layers were separated and the aqueous phase was extracted with ethyl acetate (3×20 ml). The combined organic layers were washed with brine, dried over magnesium sulfate, filtered and concentrated in vacuo. Purification via flash column chromatography (SiO$_2$, ethyl acetate/petroleum ether, 2:3, v/v) afforded the title compound (1.39 g, 87%) as a pale yellow solid. $\delta_H$(CDCl$_3$) 0.19 (6H, s), 0.98 (9H, s), 1.87 (2H, m), 2.20 (2H, m), 2.46 (4H, m), 2.99 (1H, m), 6.77 (2H, d), 7.07 (2H, d).

Intermediate 37

4-(4-{[tert-Butyl(dimethyl)silyl]oxy}phenyl)-1-[2,4-bis(methoxymethoxy)phenyl]cyclohexanol A round bottomed flask equipped with magnetic stirrer was charged with 1-bromo-2,4-bis(methoxymethoxy) benzene (277 mg, 1.00 mmol) and anhydrous tetrahydrofuran (5 ml). The stirred solution was cooled to −78° C. and N,N,N',N'-tetramethylethylene diamine (0.32 ml, 2.10 mmol) was added followed by dropwise addition of n-butyl lithium (0.88 ml, 2.10 mmol, 2.40M solution in cyclohexanes). The resulting solution was stirred for 40 min at −78° C., then 4-(4-{[tert-butyl(dimethyl)silyl] oxy}phenyl) cyclohexanone (304 mg, 1.00 mmol) was added via syringe as a solution in anhydrous tetrahydrofuran (2 ml) and the reaction mixture stirred for 30 min at −78° C., then allowed to warm to room temperature over 3 hr. The reaction was quenched with aqueous hydrochloric acid (5 ml, 0.10M), then poured into a separating funnel containing ethyl acetate (50 ml) and water (10 ml). The layers were separated and the aqueous phase extracted with ethyl acetate (3×5 ml). The combined organic layers were washed with brine (10 ml), dried over magnesium sulfate, filtered and concentrated in vacuo. The resulting oil was purified via flash column chromatography (SiO$_2$, ethyl acetate/petroleum ether, 3:7, v/v) furnishing the title compound as a white solid (127 mg, 25%) and a mixture of diastereoisomers. $\delta_H$(CDCl$_3$) 0.19 (6H, s), 0.98 (6H, s), 1.63 (2H, m), 1.84 (2H, m), 1.96 (2H, m), 2.56 (2H, m), 2.70 (1H, m), 3.48 (3H, s), 3.49 (3H, s), 3.85 (1H, s), 5.15 (2H, s), 5.24 (2H, s), 6.68 (1H, dd), 6.73 (2H, d), 6.85 (1H, d), 7.05 (2H, d), 7.33 (1H, d).

Intermediate 38 tert-Butyl (4-{4-[2,4-bis(methoxymethoxy)phenyl]-3-cyclohexen-1-yl}phenoxy) dimethylsilane A round bottomed flask equipped with magnetic stirrer was charged with 4-(4-{[tert-butyl(dimethyl)silyl] oxy}phenyl)-1-[2,4-bis(methoxymethoxy) phenyl] cyclohexanol (125 mg, 0.25 mmol), toluene (10 ml) and p-toluene sulfonic acid monohydrate (3 crystals). The reaction mixture was heated to reflux temperature for 30 min, then cooled to room temperature before adding saturated aqueous sodium bicarbonate (5 ml). The layers were separated and the aqueous layer was extracted with ethyl acetate (3×10 ml). The combined organic layers were washed with brine (10 ml), dried over magnesium sulfate, filtered and concentrated in vacuo. The title compound was isolated without further purification as an oil (118 mg, 98%) and a mixture of diastereoisomers. $\delta_H$(CDCl$_3$) 0.19 (6H, s), 0.98 (9H, s), 1.84 (1H, m), 2.00 (1H, m), 2.27 (1H, m), 2.44 (2H, m), 2.56 (1H, m), 3.48 (3H, s), 3.49 (3H, s), 5.15 (2×2H, s), 5.79 (1H, m), 6.67 (1H, dd), 6.77 (2H, d), 6.78 (1H, d), 7.07 (2H, d), 7.11 (1H, d).

Intermediate 39 tert-Butyl (4-{4-[2,4-bis(methoxymethoxy)phenyl] cyclohexyl}phenoxy) Dimethyl Silane To a round bottomed flask equipped with magnetic stirrer was added tert-butyl (4-{4-[2,4-bis(methoxymethoxy) phenyl]-3-cyclohexen-1-yl}phenoxy) dimethylsilane (118 mg, 0.24 mmol) and ethanol (15 ml). To the stirred solution, palladium (catalytic amount, 10% on activated carbon) was added in one portion. The reaction vessel was then evacuated and placed under an atmosphere of hydrogen. This process was repeated for 10 cycles before leaving under a hydrogen atmosphere. The reaction mixture was stirred vigorously for 17 hr then filtered through celite, washing with ethyl acetate. The filtrate was concentrated in vacuo affording the title compound as a colourless oil (118 mg, 100%) and a mixture of diastereoisomers. $\delta_H$(CDCl$_3$) 0.15 (6H, s), 0.92 (9H, s), 1.51 (2H, m), 1.63 (2H, m), 1.81 (2H, m), 1.94 (2H, m), 2.43 and 2.90 (1H, m), 2.84 and 3.02 (1H, m), 3.38 and 3.39 (3H, s), 3.40 (2×1.5H, s), 5.04 and 5.06 (2H, s), 5.08 and 5.10 (2H, s), 6.56 and 6.61 (1H, m), 6.70 (3H, m), 7.03 (2H, m), 7.11 (1H, d).

Intermediate 40

(±)-Methyl {4-[2,4-bis(methoxymethoxy)phenyl] cyclohexylidene}acetate

A round bottomed flask equipped with magnetic stirrer was loaded with sodium hydride (0.20 g, 5.10 mmol, 60% dispersion in mineral oil) which was washed with petroleum ether (4×20 ml). The excess petroleum ether was removed under reduced pressure. Anhydrous tetrahydrofuran (120 ml) was added and the stirred solution was cooled to 0° C. Trimethylphosphonoacetate (756 µl, 5.10 mmol) was added dropwise via syringe and the stirred mixture was allowed to warm to room temperature over 1 hr. The mixture was cooled to 0° C. prior to the addition of 4-[2,4-bis (methoxymethoxy)phenyl] cyclohexanone (1.00 g, 3.40 mmol) as a solution in tetrahydrofuran (30 ml). The pale yellow mixture was heated to reflux temperature for 0.75 hr, then cooled to room temperature and partitioned between ethyl acetate (100 ml) and saturated aqueous ammonium chloride solution (30 ml). The layers were separated and the aqueous layer was extracted with ethyl acetate (3×30 ml). The combined organic layers were washed with brine (30 ml), dried over magnesium sulfate, filtered and concentrated in vacuo, affording a yellow oil. Purification via flash column chromatography (SiO$_2$, ethyl acetate/petroleum ether, 1:2, v/v) furnished the title compound as a yellow oil (1.13 g, 95%). $\delta_H$(CD$_3$OD) 1.53–1.70 (2H, m), 2.00–2.13 (4H, m), 2.45 (2H, m), 3.26 (1H, m), 3.48 (3H, s), 3.53 (3H, s), 3.71 (3H, s), 5.17 (2H, s), 5.24 (2H, s), 5.73 (1H, s), 6.67 and 6.68 (1H, d), 6.83 (1H, d), 7.08 (1H, d).

Intermediate 41 cis/trans-Methyl {4-[2,4-bis(methoxymethoxy) phenyl]cyclohexyl} acetate

To a round bottomed flask equipped with magnetic stirrer was added (±)-methyl {4-[2,4-bis(methoxymethoxy)phenyl]

cyclohexylidene}acetate (1.13 g, 3.23 mmol) and ethanol (50 ml). To the stirred solution was added palladium (catalytic amount, 10% on activated carbon) in one portion. The reaction vessel was evacuated and placed under an atmosphere of hydrogen. This process was repeated for 10 cycles before leaving under a hydrogen atmosphere and then stirred vigorously for 17 hr. The reaction mixture was filtered through celite, washing with ethanol and the filtrate was evaporated to dryness, furnishing the title compound (1.13 g, 99%) as a colourless oil and a mixture of diastereoisomers. $\delta_H$(CD$_3$OD) 1.53 (2H, m), 1.62–1.78 (2H, m), 1.87 (4H, m), 2.93 (1H, m), 3.47 (3H, s), 3.51 (3H, s), 3.71 and 3.72 (3H, s), 5.16 and 5.17 (2H, s), 5.22 and 5.23 (2H, s), 6.66 and 6.68 (1H, d), 6.79 and 6.80 (1H, s), 7.12 and 7.15 (1H, d).

Intermediate 42

(±)-{4-[2,4-Bis(methoxymethoxy)phenyl]cyclohexylidene}acetic Acid

To a round bottomed flask equipped with magnetic stirrer was added trimethylsilyidiethylphosphonoacetate (1.08 ml, 3.83 mmol) and anhydrous tetrahydrofuran (25 ml). The stirred solution was cooled to 0° C. and n-butyl lithium (1.80 ml, 3.83 mmol, 2.2M in cyclohexanes) was added dropwise, via syringe over 5 min. The reaction mixture was allowed to warm slowly to room temperature and stirred for 17 hr. 4-[(2, 4-Bis(methoxymethoxy)phenyl)]cyclohexanone (750 mg, 2.55 mmol) was added via syringe as a solution in tetrahydrofuran (25 ml). After 2 hr stirring at room temperature, the reaction mixture was poured into a separating funnel containing aqueous sodium hydroxide solution (10 ml, 10% w/v). After extracting once with diethyl ether (10 ml), the aqueous layer was acidified by adding concentrated hydrochloric acid (10 ml), then extracted with diethyl ether (3×20 ml). The combined organic layers were washed with water (10 ml), dried over magnesium sulfate, filtered and concentrated in vacuo affording the title compound (422 mg, 52%) as an oil. $\delta_H$(CDCl$_3$) 1.86 (2H, m), 2.00–2.13 (4H, m), 2.42 (2H, m), 3.19 (1H, m), 3.48 (3H, s), 3.51 (3H, s), 5.14 (2H, s), 5.21 (2H, s), 5.71 (1H, s), 6.67 (1H, dd), 6.81 (1H, d), 7.05 (1H, d).

Intermediate 43

(±)-{4-[2,4-Dihydroxyphenyl]cyclohexylidene}acetic Acid

A round bottomed flask equipped with magnetic stirrer was loaded with (±)-{4-[2,4-bis(methoxymethoxy)phenyl]cyclohexylidene}acetic acid (25 mg, 74 μmol), acidic dowex resin (75 mg) and methanol (15 ml) then stirred at 60° C. for 3 hr. The reaction mixture was filtered through a celite plug, washing with methanol. The solvent was removed under reduced pressure to give a yellow oil (15 mg) which was purified by preparative TLC (ethyl acetate/petroleum ether, 3:1, v/v), furnishing the title compound (6.5 mg, 35%) as an oil. m/z(ES$^+$) 339 (M+H$^+$).

Intermediate 44

(±)-{4-[2,4-Bis(methoxymethoxy)phenyl]cyclohexylidene}acetonitrile

To a round bottomed flask equipped with magnetic stirrer was added sodium hydride (40 mg, 0.95 mmol, 60% dispersion in mineral oil). After washing the sodium hydride with petroleum ether (2×20 ml), the excess solvent was removed under reduced pressure. 1,2-Dimethoxyethane (10 ml) was added and the stirred suspension cooled to 0° C. Diethyl cyanomethylphosphonate (102 μl, 0.95 mmol) was added dropwise. The reaction mixture was allowed to warm slowly to room temperature over 2 hr. 4-[(2,4-Bis(methoxymethoxy)phenyl)]cyclohexanone (200 mg, 0.68 mmol) was then added as a solution in 1,2-dimethoxyethane (10 ml) and the reaction mixture stirred for 17 hr at room temperature. The reaction mixture was poured into a separating funnel containing water (50 ml) and diethyl ether (50 ml). The layers were separated and the aqueous phase extracted with diethyl ether (2×20 ml). The combined organic layers were washed with brine (20 ml), dried over magnesium sulfate, filtered and concentrated in vacuo, to give an oil. Purification via flash column chromatography (SiO$_2$, ethyl acetate/petroleum ether, 1:2, v/v) afforded the title compound (141 mg, 66%) as a pale yellow oil. $\delta_H$(CD$_3$OD) 1.57–1.70 (2H, m), 2.02–2.25 (2H, m), 2.34–2.49 (2H, m), 2.60 (1H, m), 3.03 (1H, m), 3.24 (1H, m), 3.47 (3H, s), 3.52 (3H, s), 5.17 (2H, s), 5.23(2H, s), 5.33 (1H, s), 6.66 and 6.69 (1H, d), 6.83 (1H, d), 7.09 (1H, d Intermediate 45

(±)-[4)-(2,4-Dihydroxyphenyl)cyclohexylidene]acetonitrile

To a round bottomed flask equipped with magnetic stirrer was added (±)-{4-[2,4-bis(methoxymethoxy)phenyl]cyclohexylidene}acetonitrile (141 mg, 0.45 mmol) and methanol (5 ml). The reaction mixture was stirred, the solution was heated to reflux temperature and aqueous hydrochloric acid (5 ml, 1.0M) was added slowly. Heating was continued for 1 hr and the reaction mixture was allowed to cool to room temperature prior to the addition of saturated aqueous sodium bicarbonate solution (12 ml). The reaction mixture was then partitioned between ethyl acetate (30 ml) and water (10 ml). The aqueous layer was extracted with ethyl acetate (3×15 ml) and the combined organic layers washed with brine (20 ml), dried over magnesium sulfate, filtered and concentrated in vacuo. The residue was purified via flash column chromatography (SiO$_2$, ethyl acetate/petroleum ether, 1:1, v/v) to afford the title compound as a white solid (90 mg, 88%). m/z (ES$^-$) 228 (M–H$^+$); $\delta_H$(CD$_3$OD) 1.56–1.68 (2H, m), 2.02–2.14 (2H, m), 2.33–2.48 (2H, m), 2.57 (1H, m), 3.01 (1H, m), 3.14 (1H, m), 5.31 (1H, s), 6.26 and 6.28 (1H, d), 6.32 (1H, d), 6.80 (1H, d).

Intermediate 46

(±)-1-(3,3-Difluorocyclohexyl)-2,4-bis(methoxymethoxy)benzene

Diethylaminosulfur trifluoride (34 μl) was added to a stirred solution of (±)-3-[2,4-bis(methoxymethoxy)phenyl]cyclohexanone (40 mg) in anhydrous 1,2-dimethoxyethane at room temperature under argon. After 1 hr further diethylaminosulfur trifluoride (170 μl) was added. After 48 hr, the reaction mixture was partitioned between water (20 ml) and ethyl acetate (20 ml). The aqueous layer was extracted with ethyl acetate (2×20 ml) and the combined organic extracts were dried over magnesium sulfate and evaporated in vacuo. The crude residue was purified by flash column chromatography (SiO$_2$, ethyl acetate/petrol, 1:1 v/v) to give the title compound as a gum (31 mg); m/z (ES$^+$) 317 (M+H)$^+$, R$_f$ (ethyl acetate/petrol, 1:1 v/v) 0.5.

Intermediate 47

(±)-3-[2,4-Bis(methoxymethoxy)phenyl]cyclohexanecarboxylic Acid

A solution of (±)-{3-[2,4-bis(methoxymethoxy)phenyl]cyclohexyl}methanol (50 mg) in acetone (1 ml) was added to a stirred solution of chromium (VI) oxide (64 mg) in 2M sulfuric acid (0.64 ml) at 0° C. over 3 hr. After 3 hr at 0° C. and then 16 hr at room temperature, the reaction mixture was partitioned between water (10 ml) and ethyl acetate (20 ml). The layers were separated and the aqueous layer was extracted with ethyl acetate (2×20 ml). The combined organic extracts were washed with water (20 ml), dried over magnesium sulfate and evaporated in vacuo. The residue was purified by flash column chromatography (SiO$_2$, ethyl acetate/petrol, 4:1 v/v) to give the title compound as a colourless oil (15 mg, 29%). R$_f$(ethyl acetate/petrol, 4:1 v/v) 0.5.

Intermediate 48

(±)-3-[2,4-Bis(methoxymethoxy)phenyl] cyclohexanecarboxamide

Triethylamine (16 µl) and isobutylchloroformate (14 µl) were added to a stirred solution of (±)-3-[2,4-bis (methoxymethoxy)phenyl]cyclohexanecarboxylic acid in anhydrous tetrahydrofuran (2 ml) at 0° C. under argon. After 30 min, aqueous ammonia solution (0.5 ml, 28% w/w) was added. The reaction mixture was partitioned between water (20 ml) and ethyl acetate (50 ml). The aqueous layer was extracted with ethyl acetate (2×20 ml) and the combined organic extracts were dried over magnesium sulfate and evaporated in vacuo to give the title compound (26 mg, 87%) as a mixture of diastereoisomers; m/z (ES$^+$) 324 (M+H)$^+$.

Intermediate 49

(±)-3-[2,4-Bis(methoxymethoxy)phenyl]-N-hydroxycyclohexanecarboxamide

Triethylamine (11 µl) and isobutylchloroformate (10 µl) were added to a stirred solution of (±)-3-[2,4-bis (methoxymethoxy)phenyl]cyclohexanecarboxylic acid in anhydrous tetrahydrofuran (2 ml) at 0° C. under argon. After 30 min, aqueous hydroxylamine solution (0.5 ml, 50 wt %) was added. The reaction mixture was partitioned between water (20 ml) and ethyl acetate (50 ml). The aqueous layer was extracted with ethyl acetate (2×20 ml) and the combined organic extracts were dried over magnesium sulfate and evaporated in vacuo to give the title compound as a solid (26 mg, quant.) and a mixture of diastereoisomers; m/z (ES$^+$) 340 (M+H)$^+$.

Intermediate 50

(±)-3-[2,4-Bis(methoxymethoxy)phenyl]-N-ethylcyclohexanecarboxamide

Triethylamine (11 µl) and isobutylchloroformate (10 µl) were added to a stirred solution of (±)-3-[2,4-bis (methoxymethoxy)phenyl]cyclohexanecarboxylic acid in anhydrous tetrahydrofuran (2 ml) under argon at 0° C. After 30 min, ethylamine (0.5 ml, 2M solution in tetrahydrofuran) was added. The reaction mixture was partitioned between water (20 ml) and ethyl acetate (50 ml). The aqueous layer was extracted with ethyl acetate (2×20 ml) and the combined organic extracts were dried over magnesium sulfate and evaporated in vacuo to give the title compound as a solid (24 mg, quant.) and a mixture of diastereoisomers; m/z (ES$^+$) 352 (M+H)$^+$.

Intermediate 51

(±)-3-[2,4-Bis(methoxymethoxy)phenyl]-1-(hydroxymethyl)cyclohexanol

N-Methyl morpholine N-oxide (120 mg) and osmium tetroxide (100 µl, 2.5 wt % in tert-butanol) were added to a solution of (±)-2,4-bis(methoxymethoxy)-1-(3-methylenecyclohexyl) benzene (30 mg) in tetrahydrofuran (0.7 ml) and water (0.3 ml) at room temperature. After 16 hr, celite was added to the reaction mixture followed by water (5 ml) and sodium persulfite (20 mg). The reaction mixture was filtered, the filtrate was adjusted to pH 4 with 2M hydrochloric acid solution and the aqueous volume was made up to 20 ml. The aqueous layer was extracted with ethyl acetate (3×20 ml), the combined organic extracts were washed with brine (20 ml), dried over magnesium sulfate and evaporated in vacuo. The residue was purified by flash column chromatography (SiO$_2$, ethyl acetate) to give the title compound as a solid (30 mg, 89%) and a mixture of diastereoisomers; m/z (ES$^+$) 327 (M+H)$^+$.

Intermediate 52

(±)-N-{3-[2,4-bis(methoxymethoxy)phenyl] cyclohexyl}acetamide

Triethylamine (15 µl) and acetic anhydride (10 ml) were added to a stirred solution of (±)-3-[2,4-bis (methoxymethoxy)phenyl]cyclohexylamine (29 mg) in anhydrous 1,2-dichloroethane (2 ml) at room temperature. After 0.5 hr, the reaction mixture was partitioned between water (20 ml) and ethyl acetate (50 ml) and the aqueous layer was extracted with ethyl acetate (3×20 ml). The combined organic extracts were dried over magnesium sulfate and evaporated in vacuo to give the title compound as a solid (22 mg, 66%) and a mixture of diastereoisomers; m/z (ES$^+$) 338 (M+H)$^+$.

Intermediates 53 and 54 trans-4-(2,4-Bis{[tert-butyl(dimethyl)silyl] oxy}phenyl)cyclohexanol cis-4-(2,4-Bis{[tert-butyl (dimethyl)silyl]oxy}phenyl)cyclohexanol Sodium borohydride (164 mg) was added to a stirred solution of 4-(2,4-bis{(tert-butyl(dimethyl)silyl] oxy}phenyl)cyclohexanone (1.57 g) in ethanol (50 ml) at 0° C. After 2 hr at 0° C. and then 18 hr at room temperature, the reaction mixture was partitioned between 2M HCl (20 ml), water (40 ml) and ethyl acetate (50 ml) and the aqueous layer was re-extracted with ethyl acetate (2×50 ml). The combined organic extracts were washed with brine (40 ml), dried over magnesium sulfate and evaporated in vacuo. The residue was purified using flash column chromatography (SiO$_2$, ethyl acetate/petrol, 3:17 v/v) to give the trans-title compound as a white solid (546 mg, 35%), and the cis-title compounds as a white solid (83 mg, 5%).

trans-δ$_H$(CDCl$_3$) 0.18 (6H, s), 0.22 (6H, s), 0.98 (9H, s), 1.02 (9H, s), 1.18–1.22 (4H, m), 1.80–1.84 (3H, m), 2.00–2.05 (2H, m), 2.78–2.86 (1H, m), 3.60–3.70 (1H, m), 6.28 (1H, d), 6.39 (1H, dd), 6.94 (1H, d).

cis-δ$_H$(CDCl$_3$) 0.18 (6H, s), 0.22 (6H, s), 0.98 (9H, s), 1.02 (9H, s), 1.58–1.78 (6H, m), 1.84–1.92 (2H, m), 2.70–2.80 (1H, m), 4.12 (1H, bs), 6.28 (1H, d), 6.40 (1H, dd), 7.02 (1H, d).

Intermediate 55 trans-4-(2,4-Bis{[tert-butyl(dimethyl)silyl] oxy}phenyl)cyclohexyl 4-(dimethylamino) benzoate Triethylamine (20 µl), 4-dimethylaminopyridine (catalytic amount) and 4-dimethylaminobenzoyl chloride (26 mg) were added to a stirred solution of trans-4-(2,4-bis{ [tert-butyl(dimethyl)silyl]oxy}phenyl)cyclohexanol (30 mg) in dry dichloromethane (2 ml) at room temperature under argon. After 24 hr, the solvent was removed under reduced pressure and the residue was partitioned between water (10 ml) and ethyl acetate (20 ml). The aqueous layer was extracted with ethyl acetate (2×20 ml) and the combined organic extracts were washed with brine (10 ml), dried over magnesium sulfate and evaporated in vacuo. The residue was purified by flash column chromatography ($SiO_2$, ethyl acetate/petrol, 1:24 v/v) to give the title compound as a white solid (18 mg, 45%); m/z ($ES^+$) 585 $(M+H)^+$.

Intermediate 56 cis/trans-4-(2,4-Bis{[tert-butyl(dimethyl)silyl] oxy}phenyl)cyclohexanecarboxylic Acid Pyridinium dichromate (146 mg) was added to a stirred solution of cis/trans-[4-(2,4-bis{[tert-butyl(dimethyl)silyl] oxy}phenyl)cyclohexyl]methanol (50 mg) in N,N-dimethylformamide (1 ml) at room temperature under argon. After 24 hr, the reaction mixture was partitioned between water (20 ml) and diethyl ether (30 ml). The layers were separated and the aqueous layer was extracted with diethyl ether (2×30 ml). The combined organic extracts were dried over magnesium sulfate and evaporated in vacuo. The residue was purified by flash column chromatography ($SiO_2$, ethyl acetate/petrol, 1:9 v/v) to give the title compound as a cream solid (23 mg, 44%); m/z ($ES^+$) 465 $(M+H)^+$.

Intermediate 57 trans-4-(2,4-Bis{[tert-butyl(dimethyl)silyl] oxy}phenyl)cyclohexyl Ethylcarbamate N,N-Diisopropylethylamine (199 μl) and ethyl isocyanate (90 μl) were added to a stirred solution of trans-4-(2,4-bis{ [tert-butyl(dimethyl)silyl]oxy}phenyl)cyclohexanol (50 mg) in dry dichloroethane (1 ml) at room temperature under argon. The reaction mixture was heated to 40° C. for 120 h, and was partitioned between water (50 ml) and ethyl acetate (50 ml). The layers were separated and the aqueous layer was extracted with ethyl acetate (2×50 ml). The combined organic extracts were dried over magnesium sulfate and evaporated in vacuo. The residue was purified by flash column chromatography ($SiO_2$, ethyl acetate/petrol, 1:2 v/v) to give the title compound as a solid (55 mg, 95%); $R_f$ (ethyl acetate/petrol, 1:2 v/v) 0.65.

Intermediate 58 trans-4-(2,4-Bis{[tert-butyl(dimethyl)silyl] oxy}phenyl)cyclohexyl Cyclohexylcarbamate N,N-Diisopropylethylamine (199 μl) and cyclohexyl isocyanate (128 μl) were added to a stirred solution of 4-(2,4-bis{[tert-butyl(dimethyl)silyl]oxy}phenyl)cyclohexanol (50 mg) in dry dichloroethane (1 ml) at room temperature under argon. The reaction mixture was heated to 40° C. for 120 h, and was partitioned between water (50 ml) and ethyl acetate (50 ml). The layers were separated and the aqueous layer was extracted with ethyl acetate (2×50 ml). The combined organic extracts were dried over magnesium sulfate and evaporated in vacuo. The residue was purified by flash column chromatography ($SiO_2$, ethyl acetate/petrol, 1:2 v/v) to give the title compound as a pale yellow solid (30 mg, 47%); $δ_H$($CDCl_3$) 0.12 (6H, s), 0.18 (6H, s), 0.90 (9H, s), 0.95 (9H, s), 1.00–2.10 (18H, m), 2.70–2.80 (1H, m), 3.36–3.50 (1H, m), 4.40–4.48 (1H, m), 4.50–4.62 (1H, m), 6.20 (1H, d), 6.32 (1H, dd), 6.86 (1H, d).

Intermediate 59 trans-4-(2,4-Dihydroxyphenyl)cyclohexanol 4-(2,4-Dihydroxyphenyl)cyclohexanone (18 mg) was placed in a round-bottomed flask equipped with magnetic stirrer. Ethanol (5 ml) was added, followed by sodium borohydride (3.3 mg), and the reaction mixture was stirred for 16 hr. Aqueous HCl (20 ml, 1M), followed by ethyl acetate (20 ml), was added, and the organic phase removed and washed with brine (15 ml), dried over anhydrous magnesium sulphate, filtered, and then concentrated in vacuo. The residue was purified by flash column chromatography ($SiO_2$, ethyl acetate/petroleum ether, 60:40, v/v) to afford the title compound (14 mg, 78%) as a white solid. $δ_H$($CD_3OD$) 1.38–1.56 (4H, m), 1.85–1.88 (2H, m), 2.04–2.07 (2H, m), 2.80 (1H, tt), 3.58–3.65 (1H, m), 6.24–6.29 (2H, m), 6.90 (1H, d); m/z ($ES^-$) 267 ((M+AcOH)−1)

Intermediate 60 cis-4-(2,4-Bis{[tert-Butyl(dimethyl)silyl] oxy}phenyl)cyclohexyl Methanesulfonate To a round bottom flask containing cis-4-(2,4-bis{[tert-butyl(dimethyl)silyl]oxy}phenyl) cyclohexanol (200 mg, 0.46 mmol) was added dichloromethane (10 ml) followed by triethylamine (96 μl, 0.69 mmol) and dimethylaminopyridine (catalytic amount). The flask was purged with argon and methane sulfonyl chloride (53 μl, 0.69 mmol) was added with stirring. Stirring was continued for a further 24 hr and the reaction mixture was poured into water and extracted with dichloromethane (4×20 ml). The combined organic extracts were washed with brine, dried over magnesium sulfate and concentrated in vacuo. Purification via flash column chromatography ($SiO_2$, ethyl acetate/petrol, 1:9) afforded the title compound as an oil (194 mg, 82%). $δ_H$($CDCl_3$) 0.19 (6H, s), 0.22 (6H, s), 0.97 (9H, s), 1.01 (9H, s), 1.20–1.35 (2H, m), 1.65–1.78 (4H, m), 2.15–2.22 (2H, m), 2.85–2.95 (1H, m), 3.02 (3H, s), 5.06 (1H, s), 6.30 (1H, d), 6.43 (1H, dd), 7.00 (1H, d).

Intermediate 61

[4-(2,4-Bis{[tert-butyl(dimethyl)silyl]oxy}phenyl) cyclohexyl]methyl Propionate

4-Dimethylaminopyridine (catalytic amount), triethylamine (68 μl) and propionyl chloride (42 μl) were added to a stirred solution of [4-(2,4-bis{[tert-butyl(dimethyl)silyl] oxy}phenyl) cyclohexyl]methanol in anhydrous dichloromethane (3 ml) at room temperature under argon. After 16 hr, the reaction mixture was partitioned between water (10 ml) and ethyl acetate (20 ml). The layers were separated and the aqueous layer was extracted with ethyl acetate (2×20 ml). The combined organic extracts were dried over magnesium sulfate and evaporated in vacuo. The residue was purified by flash column chromatography ($SiO_2$, ethyl acetate/petrol, 1:19 v/v) to give the title compound as a yellow oil and a mixture of diastereoisomers (114 mg, 92%); $δ_H$($CDCl_3$) −0.04 (6H, s), 0.02 (6H, s), 0.96 (9H, s), 1.00 (9H, s), 1.08–1.18 (3H, m), 1.20–2.10 (9H, m), 2.24–2.40 (2H, m), 2.76–2.92 (1H, m), 3.94 (0.6H, d), 4.18 (0.4H, d), 6.26 (1H, m), 6.40 (1H, dd), 6.94–6.98 (1H, m).

Intermediates 62 and 63

Diastereoisomers of Ethyl 4-(2,4-bis{[tert-butyl (dimethyl)silyl]oxy}phenyl)-1-hydroxycyclohexanecarboxylate A round bottom flask equipped with stirrer bar was charged with tetrahydrofuran (6 ml), ethyl vinyl ether (0.28 ml, 2.92 mmol) and cooled to −78° C. A solution of tert-butyl lithium (1 ml, 1.7 M, 1.7 mmol) was added dropwise and the flask allowed to reach 0° C. The flask was maintained at this temperature until the bright yellow colour had been discharged before being re-cooled to −78° C. A solution of 4-(4-{[tert-butyl(dimethyl)silyl]oxy}phenyl) cyclohexanone (250 mg, 0.58 mmol) in THF (4 ml) was added dropwise. After 30 min the reaction was quenched with wet THF (0.5 ml water in 5 ml of THF), poured into water (10 ml) and extracted with diethyl ether (3×10 ml). The combined organic extracts were washed with brine, dried over magnesium sulfate and concentrated in vacuo. This residue was dissolved in methanol (40 ml), cooled to −78° C. and ozonised oxygen passed through the solution for 10 min. After this time the excess ozone was removed by passing oxygen through the solution. The reaction mixture was allowed to warm to room temperature and concentrated in vacuo. Purification via flash column chromatography ($SiO_2$, ethyl acetate/petrol, 1:6) afforded the title compounds. First eluted diastereoisomer (31 mg, 11%); $\delta_H(CDCl_3)$ 0.18 (6H, s), 0.25 (6H, s), 0.97 (9H, s), 1.02 (9H, s), 1.30 (3H, t), 1.80–1.95 (8H, m), 2.82–2.95 (2H, m), 4.23 (2H, q), 6.28 (1H, d), 6.42 (1H, dd), 7.05 (1H, d). Second eluted diastereoisomer (32 mg, 12%); 5H ($CDCl_3$) 0.20 (6H, s), 0.25 (6H, s), 0.95 (9H, s), 1.00 (9H, s), 1.36 (3H, t), 1.62–1.85 (6H, m), 2.10–2.22 (2H, m), 2.87–2.98 (2H, m), 4.28 (2H, q), 6.28 (1H, d), 6.42 (1H, dd), 6.97 (1H, d).

Intermediate 64

4-{2,4-Bis [tert-butyl(dimethyl)silyloxy]phenyl Cyclohexanone Oxime

To a round bottomed flask equipped with magnetic stirrer was added 4-{2,4-bis [tert-butyl(dimethyl)silyloxy]phenyl cyclohexanone (100 mg, 0.23 mmol) and ethanol (5 ml). To the stirred suspension was added hydroxylamine hydrochloride (32 mg, 0.46 mmol) and triethylamine (103 μl, 0.74 mmol), then the solution was heated under reflux temperature for 2.5 hr. The solution was allowed to cool to room temperature then evaporated to dryness in vacuo. The residue was partitioned between ethyl acetate (20 ml) and water (10 ml) and the layers separated. The aqueous layer was extracted with ethyl acetate (3×20 ml) and the combined organic layers washed with brine (10 ml), dried over magnesium sulfate, filtered and concentrated in vacuo. The title compound was isolated (103 mg, 100%) as a white. $\delta_H(CDCl_3)$ 0.19 (6H, s), 0.24 (6H, s), 0.95 (9H, s), 1.02 (9H, s), 1.43–1.62 (2H, m), 1.77–1.87 (1H, m), 1.93–2.04 (2H, m), 2.18–2.24 (1H, m), 2.46–2.53 (1H, m), 3.05–3.15 (1H, m), 3.41–3.50 (1H, m), 6.30 (1H, d), 6.40 (1H, dd), 6.79 (1H, br), 6.92 (1H, d).

Example 1

4-(2,4-Dihydroxyphenyl)-3-cyclohexen-1-one

A round bottomed flask equipped with magnetic stirrer was charged with 8-[2,4-bis(methoxymethoxy)phenyl]-1,4-dioxaspiro[4.5]dec-7-ene (1.50 g, 4.24 mmol) and methanol (30 ml). To the stirred solution was added aqueous hydrochloric acid (30 ml, 1.0M) and the solution was heated to reflux temperature for 1.5 hr. After cooling to room temperature, saturated aqueous sodium bicarbonate (20 ml) was added and the layers separated. The aqueous layer was extracted with ethyl acetate (4×20 ml) and the combined organic layers washed with brine (20 ml), dried over magnesium sulfate, filtered and concentrated in vacuo. The resulting oil was purified via flash column chromatography ($SiO_2$, ethyl acetate/petroleum ether, 1:3, v/v) to afford the title compound as a yellow solid (323 mg, 37%). m/z (ES⁻) 203 (M−H⁺); $\delta_H(CD_3OD)$ 2.62 (2H, t), 2.86 (2H, t), 3.04 (2H, m), 5.78 (1H, m), 6.28 (1H, m), 6.32 (1H, m), 6.96 (1H, d).

Example 2a 4-(2,4-Dihydroxyphenyl)cyclohexanone

A round bottomed flask equipped with magnetic stirrer was loaded 8-[2,4-bis(methoxymethoxy)phenyl]-1,4-dioxaspiro[4.5]decane (1.30 g, 3.9 mmol) and methanol (15 ml). To the resulting stirred solution was added aqueous HCl (15 ml, 1M) in one portion. After stirring for one hr at room temperature the acid was quenched by adding saturated aqueous sodium bicarbonate solution (10 ml). After stirring vigorously for 10 min, the reaction mixture was transferred to a separating funnel and the phases separated and the aqueous phase was extracted with ethyl acetate (3×20 ml). The combined organic phases were washed with brine and the solvent evaporated. To the slightly wet crude product was added methanol (30 ml) and acidic ion exchange resin (4 g). The resulting mixture was heated under reflux, with stirring, for 5 hr. Filtering through a plug of Celite, washing with ethyl acetate, followed by removal of solvent in vacuo afforded an orange oil. Purification by flash column chromatography, ($SiO_2$, ethyl acetate/petroleum ether, 1:1, v/v) furnished the title compound as a white powder (0.54 g, 68%). m/z (ES⁻) 411 (2M−1); $\delta_H(CD_3OD)$ 1.94 (2H, ddd), 2.16–2.23 (2H, m), 2.41 (2H, dt), 2.62 (1H, t), 2.63 (1H, t), 6.24 (1H, dd), 6.31 (1H, d), 6.92 (1H, d).

Example 2b 4-(2,4-Dihydroxyphenyl)cyclohexanone

A round bottomed flask equipped with magnetic stirrer was charged with 4-(1,4-dioxaspiro[4.5]dec-8-yl)-1,3-benzenediol (11.3 g, 45.2 mmol), acetone (250 ml) and water (50 ml). To the stirred solution was added pyridinium p-toluenesulfonate (1.14 g, 4.52 mmol) in one portion and the reaction mixture was then heated to reflux temperature for 8 hr. After allowing the reaction mixture to cool to room temperature, most of the acetone was removed in vacuo and the remaining mixture was partitioned between ethyl acetate (200 ml) and water (50 ml). The aqueous layer was extracted with ethyl acetate (3×50 ml) and the combined organic layers were washed with brine (30 ml), dried over magnesium sulfate, filtered and concentrated under reduced pressure to afford an off white powder. After washing the powder with dichloromethane (100 ml) and removal of excess solvent under reduced pressure, the desired product (9.30 g, 100%) was obtained as an off-white white powder. m/z (ES⁺) 207 (M+H⁺); $\delta_H(CD_3OD)$ 1.84–1.97 (2H, m), 2.15–2.23 (2H, m), 2.36–2.45 (2H, m), 2.58–2.68 (2H, m), 3.39 (1H, tt), 6.26 (1H, dd), 6.34 (1H, d), 6.96 (1H, d).

Example 3

4-(2,4-Dihydroxyphenyl)cyclohexanone Oxime

To a round bottomed flask, equipped with magnetic stirrer was added 4-(2,4-dihydroxyphenyl)cyclohexanone (100 mg, 0.49 mmol), anhydrous ethanol (5 ml), triethylamine (102 ml) and hydroxylamine hydrochloride (51 mg, 0.73 mmol). The reaction mixture was heated under reflux for 3 hr, then evaporated in vacuo. The resulting solid was purified by flash column chromatography, ($SiO_2$, ethyl acetate/ petroleum ether, 35:65, v/v), furnishing the title compound as short white needles (107 mg, 100%). $\delta_H$(CD$_3$OD) 1.44–1.61 (2H, m), 1.81–1.88 (1H, m), 1.94–2.00 (2H, m), 2.19–2.27 (1H, m), 2.43 (1H, d), 3.04–3.10 (1H, m), 3.38 (1H, m), 6.22–6.25 (1H, m), 6.28 (1H, d), 6.84–6.86 (1H, m); m/z (EI$^-$) 220.

Example 4

O-Methyl-4-(2,4-dihydroxyphenyl)cyclohexanone Oxime

To a round bottomed flask, equipped with magnetic stirrer was added 4-(2,4-dihydroxyphenyl)cyclohexanone (21 mg, 0.10 mmol), anhydrous ethanol (3 ml), sodium acetate (16 mg, 0.20 mmol) and O-methylhydroxylamine hydrochloride (9 mg, 0.22 mmol). The reaction mixture was heated under reflux for 6 hr, then partitioned between ethyl acetate (10 ml) and water (10 ml). The organic layer was dried over anhydrous calcium sulphate, filtered and evaporated in vacuo furnishing a colourless oil. Purification via flash column chromatography (SiO$_2$, ethyl acetate/petroleum ether, 1:1, v/v), afforded the title compound as a white solid (11 mg, 47%). $\delta_H$(CD$_3$OD) 1.43–1.63 (2H, m), 1.81–1.92 (2H, m), 1.93–2.20 (2H, m), 2.24 (1H, dt), 2.38–2.44 (1H, m), 3.07 (1H, tt), 3.78 (3H, s), 6.20–6.23 (1H, m), 6.26 (1H, d), 6.85 (1H, d); m/z (ES$^-$) 234.

Example 5

O-Benzyl-4-(2,4-dihydroxyphenyl)cyclohexanone Oxime

To a round bottomed flask, equipped with magnetic stirrer, was added 4-(2,4-dihydroxyphenyl)cyclohexanone (21 mg, 0.10 mmol), anhydrous ethanol (3 ml), sodium acetate (17 mg, 0.21 mmol) and O-benzylhydroxylamine hydrochloride (18 mg, 0.21 mmol). The reaction mixture was heated under reflux for 6 hr, then partitioned between ethyl acetate (10 ml) and water (10 ml). The organic layer was dried over anhydrous calcium sulphate, filtered and evaporated in vacuo furnishing a pale pink oil which was purified by flash column chromatography (SiO$_2$, ethyl acetate/petroleum ether, 1:1, v/v) to afford the title compound as a colourless oil (11 mg, 32%). $\delta_H$ (400, CDCl$_3$) 1.47–1.68 (2H, m), 1.86–1.95 (1H, m), 1.97–2.08 (2H, m), 2.25 (1H, dt), 2.49–2.57 (1H, m), 3.02 (1H, tt), 3.42–3.50 (1H, m), 4.78 (1H, s), 4.89 (1H, s), 6.25–6.29 (1H, m), 6.33–6.37 (1H, m), 6.94 (1H, d), 7.26–7.39 (5H, m); m/z (ES$^-$) 310.

Example 6

3-(2,4-dihydroxyphenyl)-2-cyclohexen-1-one

3-[2,4-Bis(methoxymethoxy)phenyl]-2-cyclohexen-1-one (50 m g) was heated to 50° C. in methanol (4 ml) containing acidic ion exchange resin (500 mg). After 2 hr, the mixture was filtered and the filtrate was evaporated in vacuo and purified by flash column chromatography (SiO$_2$, ether/petroleum ether, 9:1, v/v) to furnish the title compound as a yellow solid (31 mg, 76%). $\delta_H$ (DMSO) 1.95 (2H, quintet), 2.30 (2H, t), 2.69 (2H, t), 6.26 (2H, overlapping m), 6.35 (1H, m), 7.10 (1H, d), 9.67 (1H, bs), 9.86 (1H, bs); m/z (ES$^-$) 407 (2M–H)$^-$.

Example 7

(±)-3-(2,4-Dihydroxyphenyl)cyclohexanone (±)-3-[2,4-Bis(methoxymethoxy)phenyl]cyclohexanone (35 mg) in methanol (4 ml) containing acidic ion exchange resin (300 mg) was stirred at 50° C. for 6 hr, and then at ambient temperature for 16 hr. The mixture was evaporated in vacuo and the residue was redissolved in acetone (4 ml) containing water (2 drops) and stirred at 50° C. for 8 hr, then at ambient temperature for 64 hr. The mixture was filtered through celite and purified by flash column chromatography (SiO$_2$, petroleum ether/ethyl acetate 1:1 v/v) to furnish the title compound as a white solid containing an equilibrium mixture of cyclized and uncyclized forms (31 mg, 76%). $\delta_H$ (DMSO) 1.1–2.3 (8H, overlapping m), 3.0 (1H, m), 6.08 (0.5H, bs), 6.16 (1H, bd), 6.25 (0.5H, bs), 6.53 (0.5H, bs), 6.75 (0.5H, d), 6.89 (0.5H, b), 8.98 (0.5H, bs), 9.02 (0.5H, bs), 9.17 (0.5H, bs); m/z (ES$^-$) 205 (M–H)$^-$.

Example 8

3-(2,4-Dihydroxyphenyl)-2-cyclohexen-1-one Oxime

3-[2,4-Bis(methoxymethoxy)phenyl]-2-cyclohexen-1-one oxime (0.1 g) was heated to 50° C. in methanol (5 ml) containing acidic ion exchange resin (0.3 g). After 4 hr, the mixture was filtered and the resin was washed with ammonia solution (50 ml). Filtrate and washings were combined, evaporated in vacuo and purified by flash column chromatography (SiO$_2$, ethyl acetate/petroleum ether, 3:2, v/v) to furnish the title compound as a yellow solid (0.058 g, 81%). $\delta_H$ (DMSO) (mixture of stereoisomers) 1.68 (2H, m, major), 1.76 (2H, m, minor), 2.26 (2H, m, minor), 2.40–2.54 (4H major+2H minor, overlapping m), 6.15–6.30 (3H major+2H minor, overlapping m), 6.85–6.95 (1H major+2H minor, overlapping m), 9.26 (1H, bs, major), 9.32 (1H, bs, minor), 9.35 (1H, bs, major), 9.40 (1H, bs, minor), 10.17 (1H, s, minor), 10.49(1H, s, major); m/z (ES$^-$) 437 (2M–H)$^-$.

Example 9

(±)-3-(2,4-Dihydroxyphenyl)cyclohexanone Oxime (±)-3-(2,4-Dihydroxyphenyl)cyclohexanone (13 mg), hydroxylamine hydrochloride (0.0065 g), and triethylamine (16 μl) were heated at 80° C. in DMF (3 ml). After 3 hr, the reaction mixture was partitioned between ethyl acetate and water. The organic layer was washed with brine, dried over magnesium sulfate, and evaporated in vacuo. The residue was purified by flash column chromatography (SiO$_2$, petroleum ether/ethyl acetate 3:2 v/v) to furnish the title compound as a white solid (12 mg, 86%). $\delta_H$(CD$_3$OD) 1.4–2.0 (6H, overlapping m), 2.10 (0.5H, m), 2.20 (0.5H, m), 2.35 (0.5H, m), 2.46 (0.5H, m), 2.94 (1H, m), 6.22–6.26 (2H, overlapping m), 6.92–6.95 (1H, overlapping m); m/z (ES$^+$) 222 (M+H)$^-$.

Example 10

(±)-4-[3-(1-Piperazinyl)cyclohexyl]-1,3-benzenediol Trifluoroacetic Acid Salt (±)-1-{3-[2,4-Bis(methoxymethoxy)phenyl] cyclohexyl}piperazine (35 mg) was heated under reflux in methanol containing acidic ion exchange resin (0.3 g) for 5 hr. The reaction mixture was filtered, and the resin was washed with methanol and aqueous ammonia, and the combined filtrate and washings were concentrated in vacuo. The crude residue was purified by preparative HPLC to furnish the title compound as an off white solid (14 mg, 38%). $\delta_H$ (d$_4$-MeOH) 1.7–1.9 (6H, overlapping m), 2.05 (1H, m), 2.20 (1H, m), 3.1–3.5 (10H, overlapping m), 6.26 (2H, overlapping m), 6.94 (1H, d); m/z (ES$^+$) 277 (M+H)$^+$.

Example 11

(±)-N-[3-(2,4-Dihydroxyphenyl)cyclohexyl]
methanesulfonamide (±)-N-{3-[2,4-Bis(methoxymethoxy)phenyl]
cyclohexyl}methanesulfonamide (34 mg) was heated under reflux in methanol (2 ml) containing acidic ion exchange resin (0.3 g) for 5 hr. The reaction mixture was filtered and the resin was washed with methanol. The combined filtrate and washings were evaporated in vacuo and the crude residue was purified by preparative HPLC to furnish a mixture of diastereoisomers of the title compound as a pale pink solid (10 mg, 38%). $\delta_H$ (d$_4$-MeOH) 1.20–2.00 (7H, overlapping m), 2.07 (1H, m), 2.90 (0.5H, m), 2.93 (1.5H, s), 2.97 (1.5H, s), 3.13 (0.5H, m), 3.30 (0.5H, m), 3.80(0.5H, m), 6.21–6.26 (1H, dd), 6.87 (0.5H, d), 6.89 (0.5H, d); m/z (ES$^-$) 284 (M–H)$^-$.

Example 12

(±)-4-[3-(Hydroxymethyl)cyclohexyl]-1,3-
benzenediol (±)-{3-[2,4-Bis(methoxymethoxy)phenyl]
cyclohexyl}methanol (35 mg) was heated at 50° C. in methanol (3.5 ml) containing acidic ion exchange resin (350 mg). After 6 hr, the mixture was filtered, the resin was washed with ethyl acetate, and the combined filtrate and washings were evaporated in vacuo. The crude residue was purified by flash column chromatography (SiO$_2$, ethyl acetate/petrol, 1:1 v/v) to furnish a mixture of diastereoisomers of the title compound as a white solid (2 mg, 8%). $\delta_H$ (d$_4$-MeOH) 0.9–1.9 (9H, overlapping m), 2.80 (0.5H, m), 2.90 (0.5H, m), 3.20–3.40 (2H, overlapping m), 6.15 (2H, m), 6.80 (0.5H, d), 6.85 (0.5H, d); m/z (ES$^-$) 221 (M–H)$^-$.

Example 13

(±)-4-[3-(Hydroxyamino)cyclohexyl]-1,3-
benzenediol Trifluoroacetate Salt

Cis-N-{3-[2,4-bis(methoxymethoxy)phenyl]
cyclohexyl}hydroxylamine (0.015 g) was heated under reflux in methanol (2 ml) containing acidic ion exchange resin (0.3 g) for 5 hr. The reaction mixture was filtered, and the resin was washed with aqueous ammonia and methanol and the combined filtrate and washings were concentrated in vacuo. The crude residue was purified by preparative HPLC to furnish the title compound as an off white solid (0.005 g, 46%). $\delta_H$ (d$_4$-MeOH) 1.25–1.60 (4H, overlapping m), 1.82 (1H, bd), 2.02 (1H, m), 2.17 (2H, overlapping m), 2.93 (1H, m), 3.36 (1H, m) 6.24 (1H, dd), 6.27 (1H, d), 6.88 (1H, d); m/z (ES$^+$) 224 (M+H)$^+$.

Example 14

4-(4-Methylenecyclohexyl)-1,3-benzenediol

Tetrabutylammonium fluoride (230 µl) was added to a stirred solution of tert-butyl-[3-{[tert-butyl(dimethyl)silyl]
oxy}-2-(4-methylenecyclohexyl)phenoxy](isopropyl)
dimethylsilane (40 mg) in tetrahydrofuran (2 ml) at room temperature. After 24 hr, further tetrabutylammonium fluoride (50 µl) was added, and after 2 hr the solvent was removed under reduced pressure. The residue was partitioned between water (20 ml) and ethyl acetate (20 ml). The layers were separated and the aqueous layer was extracted with ethyl acetate (2×20 ml). The combined organic extracts were washed with brine, dried over magnesium sulfate and evaporated in vacuo. The residue was purified by flash column chromatography (SiO$_2$, ethyl acetate/petrol, 2:3 v/v) to give the title compound as a white solid (17 mg, 90%). $\delta_H$(CD$_3$OD) 1.25–1.40 (2H, m), 1.75–1.82 (2H, m), 2.04–2.15 (2H, m), 2.22–2.30 (2H, m), 2.86 (1H, tt), 3.20 (1H, m), 4.50 (2H, s), 6.10–6.16 (2H, m), 6.72 (1H, d); m/z (ES$^+$) 205 (M+H)$^+$.

Example 15 cis/trans-4-[4-(Hydroxymethyl)cyclohexyl]-1,3-
benzenediol cis/trans-[4-(2,4-Bis{[tert-butyl(dimethyl)silyl]
oxy}phenyl)cyclohexyl]methanol (24 mg) was dissolved in THF (5 ml), and tetrabutylammonium fluoride (0.12 ml, 1.0M in THF) was added. The resulting solution was stirred at room temperature for 15 hr and then partitioned between ethyl acetate (20 ml) and water (2 ml). The aqueous phase was extracted with ethyl acetate (3×20 ml) and the combined organic phases were washed with brine (20 ml), dried over anhydrous magnesium sulphate, and concentrated in vacuo. Purification via flash column chromatography (SiO$_2$ eluting with ethyl acetate:petroleum ether, 1:1 v/v) furnished the desired compound (7 mg, 59%) as a white solid. $\delta_H$(CD$_3$OD): 0.95–1.06 (0.5H, m), 1.24–1.38 (0.5H, m), 1.43–1.60 (4H, m), 1.69–1.83 (4H, m), 2.62–2.77 (1H, m), 3.30 (1H, d), 3.56 (1H, d), 6.11–6.17 (2H, m), 6.76–7.01 (1H, m); m/z (ES$^-$) 281 (M–1+60)$^-$.

Example 16 cis/trans-4-(4-Hydroxy-4-methylcyclohexyl)-1,3-
benzenediol cis/trans-4-(2,4-Bis{[tert-butyl(dimethyl)silyl]
oxy}phenyl)-1-methylcyclohexanol (29 mg) was dissolved in THF (8 ml), and tetrabutylammonium fluoride (0.14 ml, 1.0M in THF) was added in one portion with stirring. The resulting solution was stirred for 17 hr and then partitioned between ethyl acetate (30 ml) and water (5 ml). The aqueous phase was extracted with ethyl acetate (2×10 ml), and the combined organic phases washed with brine (20 ml), dried over anhydrous magnesium sulphate, and concentrated in vacuo. Purification via flash column chromatography (SiO$_2$ eluting with ethyl acetate:petroleum ether, 1:19 v/v gradually increasing polarity to 3:7 v/v) afforded the title product as the individual 1,4-cis (5 mg, 36%) and 1,4-trans (9 mg, 64%) diastereoisomers (white solids). Cis isomer: $\delta_H$(CD$_3$OD): 1.30 (3H, s), 1.50–1.66 (4H, m), 1.69–1.77 (4H, m), 2.74–2.82 (1H, m), 6.20–6.26 (2H, m), 6.89 (1H, d); m/z (ES$^-$) 281 (M–1+60). Trans isomer: $\delta_H$ (CD$_3$OD): 1.22 (3H, s), 1.46–1.60 (4H, m), 1.69–1.82 (4H, m), 2.75 (1H, tt), 6.22–6.26 (2H, m), 6.93 (1H, d); m/z (ES$^-$) 281 (M–1+60).

Example 17 cis/trans-N-[4-(2,4-Dihydroxyphenyl)cyclohexyl]
acetamide

To a round bottomed flask equipped with magnetic stirrer was added cis/trans-N-[4-(2,4-bis{[tert-butyl(dimethyl)
silyl]oxy}phenyl)cyclohexyl] acetamide (15 mg, 31 µmol), tetrahydrofuran (3 ml) and tetra-n-butylammonium fluoride (93 µl, 93 µmol, 1.0M solution in tetrahydrofuran). The resulting solution was stirred for 3 hr. Tetra-n-butylammonium fluoride (90 µl, 90 µmol, 1.0M solution in tetrahydrofuran) was added and the solution stirred for a further 64 hr. Saturated aqueous sodium bicarbonate solution (3 ml) was added and the solvents removed in vacuo. The residue was partitioned between ethyl acetate (20 ml) and water (5 ml) and the aqueous layer extracted with ethyl acetate (3×10 ml). The combined organic layers were washed with brine (10 ml), dried over magnesium sulfate, filtered and concentrated in vacuo. Purification via flash column chromatography ($SiO_2$, methanol/dichloromethane, 1:9, v/v) afforded an oily solid (6 mg) which was a mixture of isomers by NMR. Further purification via HPLC afforded the title compound (0.5 mg, 6%) as a mixture of diastereoisomers and a colourless oil. m/z (ES$^-$) 308 (M−1+ 60{acetate}); $\delta_H$(CD$_3$OD) 1.41 (1H, m), 1.57 (1H, m), 1.70 (2H, m), 1.83 (1H, m), 1.87 (1H, m), 1.93 (1H, m), 1.96 (1.5H, m), 2.04 (1.5H, m), 2.05 (1H, m), 2.82 (1H, m), 3.72 (0.5H, m), 4.14 (0.5H, m), 6.28 (2H, m), 6.92 (0.5H, dd), 6.97 (0.5H, dd).

Example 18

(±)-O-Methyl-3-(2,4-dihydroxyphenyl) cyclohexanone Oxime (±)-3-(2,4-Dihydroxyphenyl)cyclohexanone (22 mg), methoxylamine hydrochloride (18 mg) and sodium acetate (18 mg) were heated under reflux in ethanol. After 6 hr, further methoxylamine (36 mg) and sodium acetate (36 mg) were added and the mixture heated under reflux for a further 1 hr. The reaction mixture was evaporated in vacuo and the residue was partitioned between ethyl acetate (20 ml) and water (20 ml). The aqueous layer was extracted with ethyl acetate (2×20 ml), and the combined organic extracts were dried over magnesium sulfate and evaporated in vacuo. The crude residue was purified by flash column chromatography ($SiO_2$, ethyl acetate/petrol, 1:1 v/v) to furnish the title compound as a mixture of isomers (18 mg, 72%). $\delta_H$(CDCl$_3$) 1.5–2.2 (6H, overlapping m), 2.42 (0.5H, bd), 2.69 (0.5H, bd), 2.92 (0.5H, m), 3.06 (0.5H, m), 3.24–3.38 (1H, m), 3.81 (1.5H, s), 3.88 (1.5H, s), 5.42 (0.5H, bs), 5.47 (0.5H, bs), 6.28–6.42 (2H, overlapping m), 6.86 (0.5H, bs), 6.98 (1H, m), 7.06 (0.5H, bs); m/z (ES−) 469 (2M−1)$^-$.

Example 19

(±)-3-(2,4-Dihydroxyphenyl)-1-methylcyclohexanol

Methyl magnesium chloride (0.132 ml of a 22% w/w solution in tetrahydrofuran) was added to a solution of (±)-3-(2,4-dihydroxyphenyl)cyclohexanone (20 mg) in tetrahydrofuran (3 ml) at 0° C. under argon. After 16 hr, dilute hydrochloric acid (1 ml) was added dropwise and the reaction mixture was partitioned between ethyl acetate (50 ml) and brine (50 ml). The aqueous layer was extracted with ethyl acetate (2×50 ml), and the combined organic extracts were dried over magnesium sulfate and evaporated in vacuo. The crude residue was purified by preparative HPLC to furnish the title compound as a white solid (6 mg, 28%). $\delta_H$ (d$_4$-MeOH) 1.20 (3H, s), 1.22–1.39 (2H, overlapping m), 1.46 (1H, t), 1.54–1.87 (5H, overlapping m), 3.22 (1H, m), 6.19–6.25 (2H, overlapping m), 6.86 91H, d); m/z (ES$^-$) 281 (M+60−H)$^-$.

Example 20

(±)-O-Benzyl-3-(2,4-dihydroxyphenyl) cyclohexanone Oxime (±)-3-(2,4-Dihydroxyphenyl)cyclohexanone (30 mg), O-benzylhydroxylamine hydrochloride (46 mg) and sodium acetate (24 mg) were heated under reflux in ethanol (3 ml). After 16 hr, the reaction mixture was evaporated in vacuo and the residue was partitioned between ethyl acetate (50 ml) and brine (50 ml). The aqueous layer was extracted with ethyl acetate (2×50 ml), and the combined organic extracts were dried over magnesium sulfate and evaporated in vacuo. The crude residue was purified by preparative HPLC to furnish a mixture of geometric isomers of the title compound as an off white solid (12 mg, 26%). $\delta_H$ (d$_4$-MeOH) 1.42–2.06 (6H, overlapping m), 2.12 (0.5H, dt), 2.22 (0.5H, t), 2.34 (0.5H, m), 2.46 (0.5H, m), 2.96 (1H, m), 5.02 (2H, s), 6.20–6.27 (2H, overlapping m), 6.92 (1H, m), 7.22–7.34 (5H, overlapping m); m/z (ES$^-$) 310 (M−H)$^-$.

Example 21

3-(2,4-Dihydroxyphenyl)-2-cyclopentenone Oxime

3-[2,4-Bis(methoxymethoxy)phenyl]-2-cyclopenten-1-one (20 mg) was heated at 50° C. in MeOH (4 ml) containing acidic ion exchange resin (100 mg) for 3 hr. The reaction mixture was filtered and the resin washed with ethyl acetate (20 ml). The filtrate was concentrated in vacuo and the residue purified by flash column chromatography ($SiO_2$, ethyl acetate/petrol, 7:3 v/v) to furnish 3-(2,4-dihydroxyphenyl)-2-cyclopenten-1-one (11 mg, 79%). 3-(2,4-Dihydroxyphenyl)-2-cyclopenten-1-one (6 mg), hydroxylamine hydrochloride (3.3 mg) and triethylamine (6.6 µl) were heated in ethanol (3 ml) under reflux for 3 hr. The reaction mixture was partitioned between ethyl acetate (20 ml) and water (20 ml). The aqueous phase was extracted with ethyl acetate (10 ml), and the combined organic phases were washed with brine (10 ml), dried over magnesium sulfate, and concentrated in vacuo. The crude residue was purified by flash column chromatography ($SiO_2$, ethyl acetate/petrol, 1:1 v/v) to furnish the title compound as a yellow solid and as one major isomer (4 mg, 62%). Data reported for the major isomer: $\delta_H$ (d$^4$-MeOH) 2.74–2.77 (2H, m), 2.96–2.99 (2H, m), 6.34 (1H, dd), 6.38 (1H, d), 6.96 (1H, t), 7.22 (1H, d); m/z (ES$^-$) 204 (M−H)$^-$.

Example 22

(±)-3-(2,4-Dihydroxyphenyl)cyclopentanone (±)-3-[2,4-Bis(methoxymethoxy)phenyl]cyclopentanone (8 mg) was heated at 50° C. in MeOH (3 ml) containing acidic ion exchange resin (0.1 g) for 3 hr. The reaction mixture was filtered and the resin washed with ethyl acetate (20 ml). The filtrate was concentrated in vacuo and the residue purified by flash column chromatography ($SiO_2$, ethyl acetate) to furnish the title compound as a white solid (3.8 mg, 70%). $\delta_H$ (d$^4$-MeOH) 2.52–2.13 (1H, m), 2.26–2.48 (4H, overlapping m), 2.53–2.60 (1H, m), 3.55–3.61 (1H, m), 6.29 (1H, dd), 6.33 (1H, d), 6.96 (1H, d); m/z (ES$^-$) 251 ((M+60)−1)$^-$.

Example 23

(±)-3-(2,4-Dihydroxyphenyl)cyclopentanone Oxime (±)-3-(2,4-Dihydroxyphenyl)cyclopentanone (5 mg), hydroxylamine hydrochloride (2.7 mg) and triethylamine (5.4 uM) were heated in EtOH (4 ml) under reflux for 3 hr. The reaction mixture was partitioned between ethyl acetate (20 ml) and water (20 ml). The aqueous phase was extracted with ethyl acetate (10 ml), and the combined organic phases were washed with brine (10 ml), dried over magnesium sulfate, and concentrated in vacuo. The crude residue was purified by flash column chromatography (SiO$_2$, ethyl acetate/petrol, 4:1 v/v) to furnish the title compound as a white solid and a mixture of isomers (3.8 mg, 71%). $\delta_H$ (d$^4$-MeOH) 1.80–1.93 (1H, overlapping m), 2.05–2.20 (0.5H, m), 2.39–2.55 (3H, overlapping m), 2.68–2.74 (1H, overlapping m), 2.94 (0.5H, br dd), 6.26–6.33 (2H, overlapping m), 6.94 (0.5H, d), 6.96 (0.5H, d); m/z (ES$^-$) 266 ((M+60)–1)$^-$.

Example 24 cis-N-[4-(2,4-Dihydroxyphenyl)cyclohexyl]-1-butanesulfonamide

To a round bottomed flask equipped with magnetic stirrer charged with cis-4-(2,4-bis{[tert-butyl(dimethyl)silyl]oxy}phenyl)cyclohexylamine (150 mg, 0.34 mmol) and 1,2-dichloroethane (8 ml), was added triethylamine (96 µl, 0.70 mmol) and n-butylsulfonyl chloride (55 µl, 0.40 mmol) at room temperature. 4-Dimethylaminopyridine (3 crystals) was added and the mixture stirred for 17 hr. Aqueous sodium hydroxide solution (15 ml, 0.40M) was added and the mixture stirred for 10 min. The layers were partitioned and the aqueous layer was extracted with dichloromethane (15 ml). The combined organic layers were washed with brine (15 ml), dried over magnesium sulfate, filtered and concentrated in vacuo. The resulting solid was then dissolved in tetrahydrofuran (10 ml) and acetic acid (0.15 ml), then tetra-n-butylammonium fluoride hydrate (360 mg, 1.4 mmol) was added. The mixture was stirred at room temperature for 1 hr, then ethyl acetate (10 ml) and water (15 ml) were added. The layers were partitioned and the aqueous layer was extracted with ethyl acetate (10 ml). The combined organic layers were washed with brine (10 ml), dried over magnesium sulfate, filtered and concentrated in vacuo to leave an oil. Purification via flash column chromatography (SiO$_2$, ethyl acetate/petroleum ether, 1:10 then 1:1, v/v) furnished the title compound (40 mg, 35%) as a white solid. m/z (ES$^-$) 326 (M–H$^+$); $\delta_H$(CD$_3$OD) 0.95 (3H, t), 1.45–1.55 (2H, m), 1.55–1.95 (10H, m), 2.80–2.90 (1H, m), 3.00–3.20 (2H, m), 3.65 (1H, m), 6.22–6.26 (2H, m), 6.96 (1H, d).

Example 25 trans-N-[4-(2,4-Dihydroxyphenyl)cyclohexyl]methanesulfonamide

To a round bottomed flask equipped with magnetic stirrer was added trans-N-[4-(2,4-bis{[tert-butyl(dimethyl)silyl]oxy}phenyl)cyclohexyl]methanesulfonamide (320 mg, 0.57 mmol) and 1,2-dichloroethane (50 ml). To the stirred solution was added trifluoroacetic acid (20 ml) and water (20 ml). The stirred reaction mixture was then heated under reflux for 18 hr and then cooled to room temperature. Toluene (70 ml) was added and the solvent removed in vacuo. Methanol (50 ml) was then added to the residue and the solvent removed under reduced pressure. The resulting oil was purified via flash column chromatography (SiO$_2$, ethyl acetate/petroleum ether, 1:3, 1:2, then 1:1 v/v) to furnish the title product (115 mg, 71%) as a white solid. m/z (ES$^+$) 286 (M+H$^+$); $\delta_H$(CD$_3$OD) 1.52 (4H, m), 1.89 (2H, m), 2.13 (2H, m), 2.80 (1H, m), 3.00 (3H, s), 3.28 (1H, m), 6.27 (1H, d), 6.29 (1H, dd), 6.92 (1H, d).

Example 26 cis-N-[4-(2,4-Dihydroxyphenyl)cyclohexyl]methanesulfonamide

To a round bottomed flask equipped with magnetic stirrer was added cis-N-[4-(2,4-bis{[tert-butyl(dimethyl)silyl]oxy}phenyl)cyclohexyl]methanesulfonamide (44 mg, 100 µmol) and 1,2-dichloroethane (4 ml). To the stirred solution was added methanesulfonyl chloride (10 µl, 120 mmol), triethylamine (28 µl, 200 µmol) and three crystals of 4-dimethylaminopyridine. The reaction mixture was then left stirring for 17 hr. The reaction mixture was then partitioned between aqueous sodium hydroxide (5 ml, 0.2M), and dichloromethane (5 ml). The aqueous phase was extracted with dichloromethane (2×5 ml) and the combined organic phases were washed with brine (7 ml), dried over magnesium sulfate, filtered and concentrated in vacuo to give a gum. This gum was dissolved in dichloromethane (6 ml), then water (3 ml) and trifluoroacetic acid (3 ml) were added and the mixture left to stir for 17 hr. The reaction mixture was diluted with toluene (15 ml) and the solvents were removed in vacuo. More toluene (15 ml) was added and evaporated under reduced pressure. Azeotropic removal of residual trifluoroacetic acid was effected with methanol to give a gum (38 mg). The residue was dissolved in dichloromethane (4.5 ml) and methanol (4.5 ml), then water (3 ml) and trifluoroacetic acid (3 ml) were added. The reaction mixture was stirred at room temperature for 64 hr. The reaction mixture was diluted with toluene (15 ml) and the solvents were removed in vacuo. More toluene (15 ml) was added and evaporated under reduced pressure. Azeotropic removal of residual trifluoroacetic acid was effected with methanol to give an oil (28 mg) which was purified via flash column chromatography (SiO$_2$, ethyl acetate/petroleum ether, gradient elution using 1:3, 1:2, then 1:1 v/v) to afford the title compound (13 mg, 81%) as a white solid. m/z (ES$^+$) 286 (M+H$^+$); $\delta_H$(CD$_3$OD) 1.71 (6H, m), 1.90 (2H, m), 2.87 (1H, m), 3.00 (3H, s), 3.72 (1H, m), 6.28 (1H, d), 6.30 (1H, dd), 7.01 (1H, d).

Example 27

4-[4-(4-Hydroxyphenyl)cyclohexyl]-1,3-benzenediol

To a round bottomed flask equipped with magnetic stirrer was added tert-butyl(4-{4-[2,4-bis(methoxymethoxy)phenyl]cyclohexyl}phenoxy)dimethylsilane (118 mg, 0.24 mmol), methanol (10 ml) and acidic Dowex® resin (500 mg). The reaction mixture was heated to reflux temperature for 5 hr then cooled to room temperature and filtered through a celite plug, washing with ethyl acetate. The filtrate was adsorbed onto silica gel and purified via flash column chromatography (SiO$_2$, ethyl acetate/petroleum ether, 2:3, v/v) to afford a white solid (44 mg) which was purified further by HPLC. The title compound was isolated as a white solid (12 mg, 17%). m/z (ES$^-$) 283 (M–H$^+$); $\delta_H$(CD$_3$OD) 1.52–1.96 (6H, m), 2.11 (2H, m), 2.53 and 3.07 (1H, m), 2.90 (1H, m), 6.28 (2H, m), 6.75 (2H, m), 6.95 (1H, m), 7.10 (1H, m), 7.19 (1H, m).

Example 28 cis/trans-Methyl [4-(2,4-dihydroxyphenyl)cyclohexyl]acetate

To a round bottomed flask equipped with magnetic stirrer was added cis/trans-methyl {4-[2,4-bis(methoxymethoxy)phenyl]cyclohexyl} acetate (1.00 g, 2.84 mmol) and methanol (20 ml). The stirred solution was heated to reflux temperature and aqueous hydrochloric acid (20 ml, 1 M) was added in aliquots (4×5 ml) at 10 min intervals. After 2 hr, the reaction mixture was cooled to room temperature and saturated aqueous sodium bicarbonate (50 ml) added. The reaction mixture was poured into a separating funnel containing ethyl acetate (100 ml) and water (30 ml). The layers were separated and the aqueous layer was extracted with ethyl acetate (3×30 ml). The combined organic layers were washed with brine (20 ml), dried over magnesium sulfate, filtered and concentrated in vacuo to give a white solid. Purification via flash column chromatography (SiO$_2$, ethyl acetate/petroleum ether, 1:2, v/v) afforded the title compound (0.51 g, 69%) as a mixture of diastereoisomers. m/z (ES$^+$) 265 (M+H$^+$); $\delta_H$(CD$_3$OD) 1.33–1.91 (9H, m), 2.30 (2H, m), 2.79 (1H, m), 3.72 (3H, s), 6.28 (2H, m), 6.95 (1H, m).

Example 29 trans-Methyl [4-(2,4-dihydroxyphenyl)cyclohexyl] acetate cis/trans-Methyl [4-(2,4-dihydroxyphenyl)cyclohexyl] acetate (25 mg) was purified via HPLC (acetonitrile/water, 30:70–80:20, 20 min isocratic) to afford the title compound as a white solid. m/z(ES$^+$) 265 (M+H$^+$); $\delta_H$(CD$_3$OD) 1.21 (2H, m), 1.47 (2H, m), 1.64 (1H, m), 1.88 (4H, m), 2.29 (2H, d), 2.79 (1H, m), 3.70 (3H, s), 6.28 (2H, m), 6.92 (1H, d).

Example 30 cis-Methyl [4-(2,4-dihydroxyphenyl)cyclohexyl] acetate cis/trans-Methyl [4-(2,4-dihydroxyphenyl)cyclohexyl] acetate (25 mg) was purified via HPLC (acetonitrile/water, 30:70–80:20, 20 min isocratic) to afford the title compound as a white solid. m/z(ES$^+$) 265 (M+H$^+$); $\delta_H$(CD$_3$OD) 1.60–1.79 (8H, m), 2.31 (1H, m), 2.54 (2H, d), 2.84 (1H, m), 3.71 (3H, s), 6.27 (2H, m), 6.95 (1H, d).

Example 31 trans-[4-(2,4-Dihydroxyphenyl)cyclohexyl]acetic Acid

To a round 25 ml bottomed flask containing trans-methyl [4-(2,4-dihydroxyphenyl)cyclohexyl]acetate (60 mg, 0.23 mmol) and water (4 ml) was added sodium hydroxide (32 mg, 0.78 mmol) and the solution heated to 40° C. for 1 hr. The solution was poured into a separating funnel containing ethyl acetate (15 ml) and water (10 ml). To the aqueous layer was then added aqueous hydrochloric acid (10 ml, 1.0M) and ethyl acetate (20 ml). The layers were separated and the aqueous layer extracted with ethyl acetate (3×10 ml). The combined organic extracts were washed with brine (15 ml), dried over magnesium sulfate, filtered and concentrated in vacuo affording the title compound (34 mg, 60%) as a solid. m/z (ES$^+$) 251 (M+H$^+$); $\delta_H$(CD$_3$OD) 1.20 (2H, m), 1.48 (2H, m), 1.89 (4H, m), 2.25 (2H, d), 2.81 (1H, m), 6.27 (2H, m), 6.91 (1H, m).

Example 32 cis-[4-(2,4-Dihydroxyphenyl)cyclohexyl]acetic Acid

To a round 25 ml bottomed flask containing cis-methyl [4-(2,4-dihydroxyphenyl)cyclohexyl]acetate (10 mg, 0.038 mmol) and water (4 ml) was added sodium hydroxide (5 mg, 0.13 mmol) and the solution heated to 40° C. for 1 hr. The solution was poured into a separating funnel containing ethyl acetate (15 ml) and water (10 ml). To the aqueous layer was then added aqueous hydrochloric acid (10 ml, 1.0M) and ethyl acetate (20 ml). The layers were separated and the aqueous layer extracted with ethyl acetate (3×10 ml). The combined organic extracts were washed with brine (15 ml), dried over magnesium sulfate, filtered and concentrated in vacuo affording the title compound (5 mg, 55%) as a solid. m/z (ES$^+$) 251 (M+H$^+$); $\delta_H$(CD$_3$OD) 1.61–1.77 (8H, m), 2.30 (1H, m), 2.49 (2H, d), 2.84 (1H, m), 6.27 (2H, m), 6.96 (1H, d).

Example 33 cis/trans-[4-(2,4-Dihydroxyphenyl)cyclohexyl]acetic Acid

To a round bottomed flask equipped with magnetic stirrer was added {4-[2,4-dihydroxyphenyl]cyclohexylidene}acetic acid (50 mg, 0.20 mmol) and ethanol (15 ml). To the stirred solution was added palladium (catalytic amount, 10% on activated carbon) in one portion. The reaction vessel was evacuated and then placed under an atmosphere of hydrogen. This was repeated ten times and then stirred for 17 hr under a hydrogen atmosphere at room temperature. The reaction mixture was filtered through a celite plug, washing with ethanol. The solvent was removed in vacuo to give the title compound (50 mg, 100%) as a pale yellow oil. m/z (ES$^+$) 251 (M+H$^+$); $\delta_H$(CD$_3$OD) 1.33–1.91 (9H, m), 2.30 (2H, m), 2.81 (1H, m), 6.28 (2H, m), 6.94 (1H, m).

Example 34 cis/trans-[4-(2,4-Dihydroxyphenyl)cyclohexyl] acetonitrile

To a round bottomed flask equipped with magnetic stirrer was added {4-[2,4-bis(methoxymethoxy)phenyl]cyclohexylidene}acetonitrile (408 mg, 1.3 mmol) and methanol (20 ml). The resulting solution was heated to reflux temperature and aqueous hydrochloric acid (20 ml, 1.0M) was added. The solution was heated for 1 hr then cooled and saturated aqueous sodium bicarbonate solution (50 ml) added. The mixture was partitioned between ethyl acetate (100 ml) and water (20 ml) and the aqueous layer was extracted with ethyl acetate (2×20 ml). The combined organic layers were washed with brine (20 ml), dried over magnesium sulfate, filtered and concentrated in vacuo affording an oil. To a 50 ml round bottomed flask equipped with magnetic stirrer was added crude [4-(2,4-dihydroxyphenyl)cyclohexylidene]acetonitrile (ca. 224 mg, 0.98 mmol) and ethanol (15 ml). To the stirred solution was added palladium (catalytic amount, 10% on activated carbon) in one portion. The reaction vessel was evacuated and then placed under a hydrogen atmosphere. This process was repeated 10 times before leaving the reaction mixture under a hydrogen atmosphere. Vigorous stirring was continued for 17 hr, then the reaction mixture was filtered through celite washing with methanol. The solvent was removed under reduced pressure and the residue was purified via flash column chromatography (SiO$_2$, ethyl acetate/petroleum ether, 1:1, v/v), furnishing the title compound (226 mg, 80% over 2 steps) as a colourless oil. m/z (ES$^+$) 232 (M+H$^+$); $\delta_H$(CD$_3$OD) 1.31 (1H, m), 1.52 (1H, m), 1.67 (1H, m), 1.77 (0.5H, m), 1.83 (1H, m), 1.92 (2H, m), 1.98 (2H, m), 2.22 (0.5H), 2.44 and 2.67 (2H, d), 2.84 (1H, m), 6.28 (2H, m), 6.96 (1H, m).

Example 35 cis/trans-4-[4-(2-Aminoethyl)cyclohexyl]-1,3-benzenediol Hydrochloride (Cis/trans)-[4-(2,4-dihydroxyphenyl)cyclohexyl] acetonitrile (214 mg, 0.95 mmol), ethanol (25 ml) and chloroform (1 ml) were placed in a bomb and platinum (IV) oxide (25 mg, 0.11 mmol) was added. The bomb was placed in a high pressure hydrogenation apparatus and shaken for 4 hr at ca. 50 psi under a hydrogen atmosphere. The reaction mixture was filtered through a celite plug, washing with methanol (30 ml). The solvents were removed in vacuo and the residue was washed with ethyl acetate (3×10 ml) to yield the title compound (161 mg, 64%) as a yellow oil. m/z (ES$^+$) 236 (M+H$^+$); $\delta_H$(CD$_3$OD) 1.08–1.93 (11H, m), 2.79 and 2.97 (1H, m), 2.99 (2H, m), 6.22 (2H, m), 6.88 (1H, m).

Example 36

(±)-4-(3,3-Difluorocyclohexyl)-1,3-benzenediol

A mixture of (±)-1-(3,3-difluorocyclohexyl)-2,4-bis(methoxymethoxy)benzene (30 mg), methanol (2 ml) and acidic ion exchange resin (200 mg) was heated under reflux for 4 h. The reaction mixture was filtered and the resin was washed with methanol. The combined filtrate and washings were evaporated in vacuo and the crude residue was purified by preparative HPLC to give the title compound as a solid (5 mg, 23%). $\delta_H$(CD$_3$OD) 1.2–2.2 (8H, m), 3.08 (1H, m), 6.23–6.27 (2H, m), 6.87 (1H, d); m/z (ES$^-$) 287 (M–1+AcOH)$^-$.

Example 37

(±)-3-(2,4-Dihydroxyphenyl)cyclohexanecarboxamide (±)-3-[2,4-Bis(methoxymethoxy)phenyl]cyclohexanecarboxamide (22 mg), methanol (2 ml) and acidic ion exchange resin (300 mg) were heated to reflux for 5 hr. The reaction mixture was filtered and the resin was washed with methanol. The combined filtrate and washings were evaporated in vacuo and the crude residue was purified by preparative HPLC to give the title compound as a white solid (5 mg, 31%). $\delta_H$(CD$_3$OD) 1.45–1.82 (6H, m), 2.07–2.19 (2H, m), 2.62–2.69 (1H, m), 3.00–3.09 (1H, m), 6.20–6.28 (2H, m), 6.89 (1H, d); m/z (ES$^+$) 236 (M+H)$^+$.

Example 38

(±)-3-(2,4-Dihydroxyphenyl)-N-hydroxycyclohexanecarboxamide (±)-3-[2,4-Bis(methoxymethoxy)phenyl]cyclohexyl}methanol (25 mg), methanol (2 ml) and acidic ion exchange resin (300 mg) were heated under reflux for 4 hr. The reaction mixture was filtered and the resin was washed with methanol. The combined filtrate and washings were evaporated in vacuo and the crude residue was purified by preparative HPLC to give the title compound as a solid (5 mg, 27%). $\delta_H$(CD$_3$OD) 1.28–2.40 (8H, m), 2.08–2.20 (0.5H, m), 2.78–2.94 (1H, m), 3.60–3.72 (2H, m), 6.20–6.28 (2H, m), 6.80–6.90 (1H, m); m/z (ES$^-$) 250 (M–H)$^-$.

Example 39

(±)-3-(2,4-Dihydroxyphenyl)-N-ethylcyclohexanecarboxamide (±)-3-[2,4-Bis(methoxymethoxy)phenyl]-N-ethylcyclohexanecarboxamide (25 mg), methanol (2 ml) and acidic ion exchange resin (300 mg) were heated to reflux for 4 hr. The reaction mixture was filtered and the resin was washed with methanol. The combined filtrate and washings were evaporated in vacuo and the crude residue was purified by preparative HPLC to furnish the title compound as a solid (2 mg, 12%). $\delta_H$(CD$_3$OD) 1.80 (3H, t), 1.30–1.60 (4H, m), 1.74–1.94 (4H, m), 2.26–2.36 (1H, m), 2.82–2.92 (1H, m), 3.16 (2H, q), 6.21–6.26 (2H, m), 6.88 (1H, d); m/z (ES$^+$) 264 (M+H)$^+$.

Example 40

(±)-4-[3-Hydroxy-3-(hydroxymethyl)cyclohexyl]-1,3-benzenediol (±)-3-[2,4-Bis(methoxymethoxy)phenyl]-1-(hydroxymethyl)cyclohexanol (29 mg), methanol (2 ml) and acidic ion exchange resin (300 mg) were heated under reflux for 3 hr. The reaction mixture was filtered and the resin was washed with methanol. The combined filtrate and washings were evaporated in vacuo and the crude residue was purified by preparative HPLC to furnish the title compound as a cream solid (5 mg, 24%). $\delta_H$(CD$_3$OD) 1.20–2.00 (8H, m), 2.89 (1H, tt), 3.61 (1H, d), 3.69 (1H, d), 6.20–6.26 (2H, m), 6.90 (1H, d); m/z (ES$^-$) 237 (M–H)$^-$.

Example 41

(±)-N-[3-(2,4-dihydroxyphenyl)cyclohexyl]acetamide (±)-N-{3-[2,4-bis(methoxymethoxy)phenyl]cyclohexyl}acetamide (20 mg), methanol (2 ml) and acidic ion exchange resin (300 mg) were heated under reflux for 3 hr. The reaction mixture was filtered and the resin was washed with methanol. The combined filtrate and washings were evaporated in vacuo and the crude residue was purified by preparative HPLC to furnish the title compound as a solid (5 mg, 34%). $\delta_H$(CD$_3$OD) 1.10–200 (1H, m), 2.90 (0.3H, tt), 3.08 (0.7H, tt), 3.70–380 (0.3H, m), 4.16 (0.7H, m), 6.20–6.26 (2H, m), 6.84–6.90 (1H, m); m/z (ES$^+$) 250 (M+H)$^+$.

Example 42 trans-4-(2,4-Dihydroxyphenyl)cyclohexyl) 4-(dimethylamino)benzoate

A mixture of trans-4-(2,4-bis{[tert-butyl(dimethyl)silyl]oxy}phenyl)cyclohexyl 4-(dimethylamino)benzoate (18 mg), methanol (5 ml) and Amberlyst fluoride resin (0.5 g) were stirred at room temperature for 24 hr. The reaction mixture was filtered, and the filtrate was evaporated in vacuo. The residue was purified by flash column chromatography (SiO$_2$, ethyl acetate/petrol, 2:3 v/v) to give the title compound as a white solid (8 mg, 73%). $\delta_H$(CD$_3$OD) 1.56–1.70 (4H, m), 1.88–1.94 (2H, m), 2.16–2.20 (2H, m), 2.80–2.90 (1H, m), 3.00 (6H, s), 6.20–2.26 (2H, m), 6.70 (2H, d), 6.92 (1H, d), 7.62 (2H, d); m/z (ES$^+$) 356 (M+H)$^+$.

Example 43 cis/trans-4-(2,4-Dihydroxyphenyl)cyclohexanecarboxylic Acid

Tetrabutylammonium fluoride (0.12 ml) was added to a stirred solution of 4-(2,4-bis{[tert-butyl(dimethyl)silyl]oxy}phenyl)cyclohexanecarboxylic acid (22 mg) in tetrahydrofuran (1 ml) at room temperature under argon. After 24 hr, the reaction mixture was partitioned between ethyl acetate (30 ml) and water (30 ml). The layers were separated and the aqueous layer was extracted with ethyl acetate (2×30 ml). The combined organic extracts were dried over magnesium sulfate and evaporated in vacuo. The residue was purified by flash column chromatography (SiO$_2$, ethyl acetate/petrol, 7:1 v/v, <1% acetic acid) to give the title compound as an orange solid (10 mg, 89%). $\delta_H$(CD$_3$OD) 1.40–1.65 (4H, m), 1.88–1.95 (2H, m), 2.06–2.14 (2H, m), 2.35 (1H, tt), 2.82 (1H, it), 6.25–6.30 (2H, m), 6.90 (1H, d); m/z (ES$^-$) 235 (M−H)$^-$.

Example 44 trans-4-(2,4-Dihydroxyphenyl)cyclohexyl Ethylcarbamate

A mixture of trans-4-(2,4-bis{[tert-butyl(dimethyl)silyl]oxy}phenyl)cyclohexyl ethylcarbamate (18 mg), methanol (10 ml) and Amberlyst fluoride resin (0.3 g) were stirred at room temperature for 24 hr. The reaction mixture was filtered, and the filtrate was evaporated in vacuo. The residue was purified by flash column chromatography (SiO$_2$, ethyl acetate/petrol, 1:3 v/v) to give the title compound as a white solid (24 mg, 87%). $\delta_H$(CD$_3$OD) 1.10 (3H, t), 1.40–1.60 (4H, m), 1.80–1.90 (2H, m), 2.00–2.10 (2H, m), 2.72–2.80 (1H, m), 3.10 (2H, t), 4.50–4.60 (1H, m), 6.20–6.26 (2H, m), 6.88 (1H, d); m/z (ES$^+$) 280 (M+H)$^+$.

Example 45 trans-4-(2,4-Dihydroxyphenyl)cyclohexyl Cyclohexylcarbamate

A mixture of trans-4-(2,4-bis{[tert-butyl(dimethyl)silyl]oxy}phenyl)cyclohexyl cyclohexylcarbamate (28 mg), methanol (10 ml) and Amberlyst fluoride resin (0.3 g) were stirred at room temperature for 72 hr. The reaction mixture was filtered and the filtrate was evaporated in vacuo. The residue was purified by flash column chromatography (SiO$_2$, ethyl acetate/petrol, 1:3 v/v) to give the title compound as a white solid (6 mg, 36%); $\delta_H$(CD$_3$OD) 1.10–2.12 (18H, m), 2.70–2.82 (1H, m), 4.46–4.60 (1H, m), 6.18–6.30 (2H, m), 6.80–6.92 (1H, m); m/z (ES$^+$) 334 (M+H)$^+$.

General Procedure for Preparation for Examples 46–53

A round bottom flask equipped with stirrer bar was charged with trans-4-(2,4-dihydroxyphenyl)cyclohexanol (208 mg, 1 mmol), dichloromethane (20 ml), triethylamine (1.4 ml, 10 mmol) and 4-dimethylaminopyridine (catalytic amount). The flask was purged with argon and the appropriate acid chloride (5 mmol) added dropwise with stirring. The reaction mixture was then set aside for 24 hr. The reaction mixture was then diluted with dichloromethane (20 ml) and washed successively with hydrochloric acid (10 ml of a 2M aqueous solution), saturated aqueous sodium hydrogen carbonate (10 ml), brine (10 ml), dried over magnesium sulfate and evaporated in vacuo. The resulting residue was suspended in a mixture of tetrahydrofuran (20 ml) and methanol (5 ml) and cesium carbonate (685 mg, 2.1 mmol) in water (5 ml) was added. The reaction mixture was warmed at 50° C. until TLC analysis indicated complete conversion to the title compound. The reaction solution was concentrated to approximately one quarter its original volume, diluted with water (10 ml) and extracted with ethyl acetate (3×10 ml). The combined organic extracts were washed with brine, dried over magnesium sulfate and evaporated in vacuo. The residue was purified using flash column chromatography (SiO$_2$, ethyl acetate/petrol).

Example 46 trans-4-(2,4-Dihydroxyphenyl)cyclohexyl 4-tert-butylbenzoate

The title compound was isolated as an oil (180 mg, 49%), as described in the general procedure above. $\delta_H$ (d$^4$-MeOH) 1.34 (9H, s), 1.54–1.71 (4H, m), 1.87–1.94 (2H, m), 2.14–2.21 (2H, m), 2.86 (1H, m), 4.95 (1H, m), 6.24 (1H, dd), 6.27 (1H, d), 6.91 (1H, d), 7.50 (2H, d), 7.94 (2H, d); m/z (ES$^+$) 369 (M+H)$^+$.

Example 47 trans-4-(2,4-Dihydroxyphenyl)cyclohexyl 4-fluorobenzoate

The title compound was isolated as a white solid (133 mg, 40%), as described in the general procedure above. $\delta_H$ (d$^4$-MeOH) 1.54–1.72 (4H, m), 1.86–1.95 (2H, m), 2.13–2.20 (2H, m), 2.86 (1H, m), 4.96 (1H, m), 6.24 (1H, dd), 6.26 (1H, d), 6.91 (1H, d), 7.18 (2H, m), 8.06 (2H, m); m/z (ES$^+$) 331 (M+H)$^+$.

Example 48 trans-4-(2,4-Dihydroxyphenyl)cyclohexyl 4-trifluoromethylbenzoate

The title compound was isolated as a white solid (261 mg, 69%), as described in the general procedure above. $\delta_H$ (d$^4$-MeOH) 1.54–1.74 (4H, m), 1.88–1.96 (2H, m), 2.16–2.24 (2H, m), 2.88 (1H, m), 5.01 (1H, m), 6.25 (1H, dd), 6.28 (1H, d), 6.91 (1H, d), 7.79 (2H, m), 8.17 (2H, m); m/z (ES$^+$) 381 (M+H)$^+$.

Example 49 trans-4-(2,4-Dihydroxyphenyl)cyclohexyl 4-methoxybenzoate

The title compound was isolated as a white solid (248 mg, 73%), as described in the general procedure above. $\delta_H$ (d$^4$-MeOH) 1.54–1.74 (4H, m), 1.88–1.96 (2H, m), 2.16–2.24 (2H, m), 2.88 (1H, m), 5.01 (1H, m), 6.25 (1H, dd), 6.28 (1H, d), 6.91 (1H, d), 7.79 (2H, m), 8.17 (2H, m); m/z (ES$^+$) 381 (M+H)$^+$.

Example 50 trans-4-(2,4-Dihydroxyphenyl)cyclohexyl 4-methylbenzoate

The title compound was isolated as a white solid (75 mg, 23%), as described in the general procedure above. $\delta_H$ (d$^4$-MeOH) 1.53–1.75 (4H, m), 1.89–1.96 (2H, m), 2.12–2.23 (2H, m), 2.40 (3H, s), 2.86 (1H, m), 4.98 (1H, m), 6.25 (2H, m), 6.92 (1H, d), 7.25 (2H, m), 7.90 (2H, m); m/z (ES$^+$) 653 (2M+H)$^+$.

Example 51 trans-4-(2,4-Dihydroxyphenyl)cyclohexyl 4-chlorobenzoate

The title compound was isolated as a white solid (230 mg, 67%), as described in the general procedure above. $\delta_H$ (d$^4$-MeOH) 1.54–1.75 (4H, m), 1.88–1.97 (2H, m), 2.15–2.24 (2H, m), 2.87 (1H, m), 4.98 (1H, m), 6.22–6.29 (2H, m), 6.92 (1H, d), 7.49 (2H, d), 8.00 (2H, d); m/z (ES$^+$) 347 (M+H)$^+$.

Example 52 trans-4-(2,4-Dihydroxyphenyl)cyclohexyl 3,4-dimethylbenzoate

The title compound was isolated as a white solid (84 mg, 25%), as described in the general procedure above. $\delta_H$ (d⁴-MeOH) 1.55–1.72 (4H, m), 1.88–1.95 (2H, m), 2.14–2.21 (2H, m), 2.32 (3H, s), 2.33 (3H, s), 2.85 (1H, m), 4.95 (1H, m), 6.22–6.28 (2H, m), 6.92 (1H, d), 7.21 (1H, d), 7.75 (1H, d), 7.79 (1H, s); m/z (ES⁺) 341 (M+H)⁺.

Example 53 trans-4-(2,4-Dihydroxyphenyl)cyclohexyl 3,4-dichlorobenzoate

The title compound was isolated as a white solid (304 mg, 80%), as described in the general procedure above. $\delta_H$ (d⁴-MeOH) 1.56–1.78 (4H, m), 1.86–1.98 (2H, m), 2.12–2.23 (2H, m), 2.84 (1H, m), 4.99 (1H, m), 6.20–6.30 (2H, m), 6.92 (1H, d), 7.64 (1H, d), 7.92 (1H, d), 8.12 (1H, s); m/z (ES⁻) 379 (M–H)⁻.

Example 54 trans-4-[4-(Phenylsulfanyl)cyclohexyl]-1,3-benzenediol

A round bottom flask containing thiophenol (30 µl, 0.29 mmol), cesium fluoride (44 mg, 0.29 mmol) and N,N-dimethylformamide (3 ml) was warmed at 40° C. for 1 hr. To this was added cis-4-(2,4-bis{[tert-butyl(dimethyl)silyl]oxy}phenyl)cyclohexyl methanesulfonate (100 mg, 0.19 mmol) in N,N-dimethylformamide (1 ml) and the reaction mixture stirred at 50° C. for 18 hr. The reaction mixture was poured into saturated aqueous sodium hydrogen carbonate (10 ml) and extracted with ethyl acetate (3×20 ml). The combined organic extracts were washed with brine (10 ml), dried over magnesium sulfate and concentrated in vacuo. Purification via flash column chromatography (SiO₂, ethyl acetate/petrol, 1:3) afforded the title compound (23 mg, 40%) as an off-white solid. $\delta_H$ (d⁴-MeOH) 1.40–1.57 (4H, m), 1.82–1.90 (2H, m), 2.04–2.16 (2H, m), 2.80 (1H, m), 3.13 (1H, m), 6.19–6.28 (2H, m), 6.88 (1H, d), 7.23 (1H, m), 7.30 (2H, m), 7.40 (2H, m); m/z (ES⁺) 301 (M+H)⁺.

Example 55 trans-4-[4-(Phenylsulfonyl)cyclohexyl]-1,3-benzenediol

A round bottom flask containing trans-4-[4-(phenylsulfanyl)cyclohexyl]-1,3-benzenediol (18 mg, 0.06 mmol) and dichloromethane (2 ml) was cooled to 0° C. and meta-chloroperbenzoic acid (50–60%, 41 mg, 0.24 mmol) was added with stirring. After 30 min at this temperature the reaction mixture was poured into saturated sodium thiosulfate solution (5 ml) and partitioned between saturated aqueous sodium hydrogen carbonate (10 ml) and dichloromethane (10 ml). The aqueous phase was further extracted with dichloromethane (2×10 ml) and the combined organic extracts were washed with brine, dried over magnesium sulfate and concentrated in vacuo. Purification via flash column chromatography (SiO₂, ethyl acetate/petrol, 30:70) afforded the title compound (6 mg, 30%) as an off-white solid. $\delta_H$ (d⁴-MeOH) 1.40–1.62 (4H, m), 1.88–1.95 (2H, m), 2.05–2.13 (2H, m), 2.72 (1H, m), 3.18 (1H, m), 6.08–6.13 (2H, m), 6.82 (1H, d), 7.64 (2H, m), 7.75 (1H, m), 7.90 (2H, m); m/z (ES⁺) 333 (M+H)⁺.

Example 56

[4-(2,4-Dihydroxyphenyl)cyclohexyl]methyl Propionate

A mixture of [4-(2,4-Bis{[tert-butyl(dimethyl)silyl]oxy}phenyl)cyclohexyl]methyl propionate (110 mg), methanol (10 ml) and Amberlyst fluoride resin (0.4 g) were stirred at room temperature for 72 hr. The reaction mixture was filtered, and the filtrate was evaporated in vacuo. The residue was purified by flash column chromatography (SiO₂, ethyl acetate/petrol, 1:2 v/v) to give the title compound as a cream solid and a mixture of diastereoisomers (44 mg, 73%). $\delta_H$(CDCl₃) 1.17 (3H, t), 1.38–2.14 (9H, m), 2.34–2.40 (2H, q), 2.64–2.80 (1H, m), 3.96 (0.6H, d), 4.20 (0.4H, d), 5.10–5.24 (2H, m), 6.28–6.33 (1H, m), 6.36–6.40 (1H, m), 6.98 (1H, dd); m/z (ES⁺) 279 (M+H)⁺.

Examples 57 and 58

Diastereoisomers of Ethyl 4-(2,4-dihydroxyphenyl)-1-hydroxycyclohexane Carboxylate A solution of one isomer of ethyl 4-(2,4-bis{[tert-butyl(dimethyl)silyl]oxy}phenyl)-1-hydroxycyclohexanecarboxylate (25 mg, 0.05 mmol) in methanol (2 ml) was stirred rapidly with Amberlyst A-26 (100 mg) for 18 hr. After this time the reaction mixture was filtered. The resin was then stirred rapidly for 1 hr in a solution of methanol (2 ml) and glacial acetic acid (5 drops). The reaction mixture was filtered and the combined filtrates concentrated in vacuo. Purification via flash column chromatography (SiO₂, ethyl acetate/petrol, 2:1) afforded the title compound (3 mg, 21%) as a white solid. $\delta_H$ (d⁴-MeOH) 1.29 (3H, t), 1.61–1.69 (2H, m), 1.73–1.98 (6H, m), 2.81–2.90 (1H, m), 4.18 (2H, q), 6.21–6.27 (2H, m), 6.91 (1H, d); m/z (ES⁻) 279 (M–H)⁻.

A solution of the other isomer of ethyl 4-(2,4-bis{[tert-butyl(dimethyl)silyl]oxy}phenyl)-1-hydroxycyclohexanecarboxylate (25 mg, 0.05 mmol) in methanol (2 ml) was stirred rapidly with Amberlyst A-26 (100 mg) for 18 hr. After this time the reaction mixture was filtered. The resin was then stirred rapidly for 1 hr in a solution of methanol (2 ml) and glacial acetic acid (5 drops). The reaction mixture was filtered and the combined filtrates concentrated in vacuo. Purification via flash column chromatography (SiO₂, ethyl acetate/petrol, 2:1) afforded the title compound (5 mg, 34%) as a white solid. $\delta_H$ (d⁴-MeOH) 1.22 (3H, t), 1.40–1.54 (4H, m), 1.63–1.74 (2H, m), 2.18–2.25 (2H, m), 2.68–2.78 (1H, m), 4.14 (2H, q), 6.11 (1H, dd), 6.15 (1H, d), 6.71 (1H, d); m/z (ES⁻) 279 (M–H)⁻.

Example 59

Cis/trans-4-[4-(hydroxyamino)cyclohexyl]-1,3,benzenediol

To a stirred solution of 4-(2,4-dihydroxyphenyl)cyclohexanone oxime (90 mg, 0.41 mmol) in acetic acid (3 ml) was added sodium cyanoborohydride (28 mg, 0.45 mmol) in one portion. After stirring for 16 hr, a further portion of sodium cyanoborohydride (28 mg) was added and stirring continued for a further 48 hr. The reaction mixture was poured into a mixture of water (3 ml) and ethyl acetate (25 ml) and stirred for 30 min. The solution was partitioned, and the aqueous layer further extracted with ethyl acetate (5×10 ml). The combined organics were washed with brine (15 ml), dried over magnesium sulfate and concentrated in vacuo. Purification by HPLC afforded the title compound as a pale pink solid (62 mg, 68%). $\delta_H$(CD₃OD) 1.57–1.77 (3H, m), 1.78–1.84 (1H, m), 1.90–2.09 (2H, m), 2.27–2.12 (2H, m), 2.87 (0.6H, m), 3.03 (0.4H, m), 3.58 (0.4H, m), 3.68 (0.6H, m), 6.25–6.32 (2H, m), 6.92 (0.6H, d), 6.99 (0.4H, d), m/z (ES⁻) 222 (M–H)⁻.

Example 60

Trans-4-[4-(methoxyamino)cyclohexyl]-1,3,benzenediol

To a stirred solution of O-methyl-4-(2,4-dihydroxyphenyl)cyclohexanone oxime (18 mg, 0.076 mmol) in acetic acid (1 ml) was added sodium cyanoborohydride (25 mg, 0.4 mmol) in one portion. After stirring overnight the reaction mixture was partitioned between water (10 ml) and ethyl acetate (10 ml). The aqueous layer was further extracted with ethyl acetate (10 ml) and the combined organic phases were washed with saturated sodium hydrogen carbonate solution (10 ml), dried over magnesium sulfate and concentrated in vacuo. Purification by flash column chromatography ($SiO_2$, ethyl acetate/petrol 2:3) afforded the title compound as a solid (12 mg, 66%). $δ_H$(CDCl$_3$) 1.13–1.26 (2H, m), 1.30–1.45 (2H, m), 1.80–1.89 (2H, m), 1.90–2.00 (2H, m), 2.68–2.78 (1H, m), 2.80–2.90 (1H, m), 3.49 (3H, s), 6.19 (1H, d), 6.24 (1H, dd), 6.86 (1H, d); m/z (ES$^+$) 279 (MH+CH$_3$CN)$^+$.

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

What is claimed is:

1. A compound of formula 1:

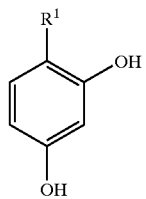

I or a pharmaceutically acceptable salt thereof, wherein:

$R^1$ is a ($C_3$–$C_8$)cycloalkyl ring or ($C_5$–$C_8$)cycloalkenyl ring, wherein either the cycloalkyl ring or cycloalkenyl ring is substituted by one to three substituents independently selected from the group consisting of cyano; halo; ($C_1$–$C_6$)alkyl; aryl; ($C_2$–$C_9$)heterocycloalkyl; ($C_2$–$C_9$)heteroaryl; aryl($C_1$–$C_6$)alkyl-; =O; =CHO ($C_1$–$C_6$)alkyl; amino; hydroxy; ($C_1$–$C_6$)alkoxy; aryl ($C_1$–$C_6$)alkoxy-; ($C_1$–$C_6$)acyl; ($C_1$–$C_6$)alkylamino-; aryl($C_1$–$C_6$)alkylamino-; amino($C_1$–$C_6$)alkyl-; ($C_1$–$C_6$)alkoxy-CO—NH—; ($C_1$–$C_6$)alkylamino-CO—; ($C_2$–$C_6$)alkenyl; ($C_2$–$C_6$)alkynyl; hydroxy ($C_1$–$C_6$)alkyl-; ($C_1$–$C_6$)alkoxy($C_1$–$C_6$)alkyl-; ($C_1$–$C_6$) acyloxy($C_1$–$C_6$)alkyl-; nitro; cyano($C_1$–$C_6$)alkyl-; halo ($C_1$–$C_6$)alkyl-; nitro($C_1$–$C_6$)alkyl-; trifluoromethyl; trifluoromethyl($C_1$–$C_6$)alkyl; ($C_1$–$C_6$)acylamino-; ($C_1$–$C_6$)acylamino($C_1$–$C_6$)alkyl-; ($C_1$–$C_6$)alkoxy ($C_1$–$C_6$)acylamino-; amino($C_1$–$C_6$)acyl-; amino ($C_1$–$C_6$)acyl($C_1$–$C_6$)alkyl-; ($C_1$–$C_6$)alkylamino ($C_1$–$C_6$)acyl-; (($C_1$–$C_6$) alkyl)$_2$amino($C_1$–$C_6$)acyl-; —CO$_2$R$^2$; —($C_1$–$C_6$)alkyl-CO$_2$R$^2$; —C(O)N(R$^2$)$_2$; —($C_1$–$C_6$)alkyl-C(O)N(R$^2$)$_2$; R$^2$ON=; R$^2$ON= ($C_1$–$C_6$)alkyl-; R$^2$ON=CR$^2$($C_1$–$C_6$)alkyl-; —NR$^2$ (OR$^2$); —($C_1$–$C_6$)alkyl-NR$^2$(OR$^2$); —C(O)(NR$^2$R$^2$); —($C_1$–$C_6$)alkyl-C(O)(NR$^2$OR$^2$); —S(O)$_m$R$^2$; wherein each R$^2$ is independently selected from hydrogen, ($C_1$–$C_6$)alkyl, aryl, or aryl($C_1$–$C_6$)alkyl-; R$^3$C(O)O—, wherein R$^3$ is ($C_1$–$C_6$)alkyl, aryl, or aryl($C_1$–$C_6$)alkyl-; R$^3$C(O)O—($C_1$–$C_6$)alkyl-; R$^4$R$^5$N—C(O)—O—;

R$^4$R$^5$NS(O)$_2$—; R$^4$R$^5$NS(O)$_2$($C_1$–$C_6$)alkyl-; R$^4$S(O)$_2$R$^5$N—; R$^4$S(O)$_2$R$^5$N($C_1$–$C_6$)alkyl-; wherein m is 0, 1 or 2, and R$^4$ and R$^5$ are each independently selected from hydrogen or ($C_1$–$C_6$)alkyl; —C(=NR$^6$)(N(R$^4$)$_2$); or —($C_1$–$C_6$)alkyl-C(=NR$^6$)(N(R$^4$)$_2$) wherein R$^6$ represents OR$^2$ or R$^2$ wherein R$^2$ is defined as above;

with the proviso that the cycloalkenyl ring is not aromatic;

with the proviso that R$^1$ must be substituted by at least one of R$^3$C(O)O—, R$^3$C(O)O—($C_1$–$C_6$)alkyl-, R$^2$ON=, R$^2$ON=($C_1$–$C_6$)alkyl-, R$^2$ ON=CR$^2$($C_1$–$C_6$)alkyl-, —NR$^2$(OR$^2$), R$^4$R$^5$NS(O)$_2$—, R$^4$R$^5$NS(O)$_2$($C_1$–$C_6$) alkyl-, R$^4$S(O)$_2$R$^5$N—, or R$^4$S(O)$_2$R$^5$N($C_1$–$C_6$)alkyl-;

with the proviso that when R$^1$ is only substituted by one of R$^2$ON=, then R$^2$ cannot be hydrogen.

2. The compound of claim 1, wherein R$^1$ is a cyclohexyl or cyclohexenyl ring substituted at the 3- or 4-position, or a cyclopentyl or cyclopentenyl ring substituted at the 3-position.

3. The compound of claim 1, wherein R$^1$ is monosubstituted.

4. The compound of claim 1, wherein R$^1$ is disubstituted.

5. The compound of claim 1, wherein R$^1$ is substituted by at least one of R$^3$C(O)O— or R$^3$C(O)O—($C_1$–$C_6$)alkyl-.

6. The compound of claim 1, wherein R$^1$ is substituted by at least one of R$^2$ ON=, R$^2$ON=($C_1$–$C_6$)alkyl-, or R$^2$ON=CR$^2$($C_1$–$C_6$)alkyl-.

7. The compound of claim 1, wherein R$^1$ is substituted by at least one of —NR$^2$(OR$^2$).

8. The compound of claim 1, wherein R$^1$ is substituted by at least one of R$^4$R$^5$NS(O)$_2$—, R$^4$R$^5$NS(O)$_2$($C_1$–$C_6$)alkyl-, R$^4$S(O)$_2$R$^5$N—, or R$^4$S(O)$_2$R$^5$N($C_1$–$C_6$)alkyl-.

9. The compound of claim 1, wherein R$^1$ is substituted by at least one of R$^4$S(O)$_2$R$^5$N— or R$^4$S(O)$_2$R$^5$N($C_1$–$C_6$) alkyl-.

10. The compound of claim 1, wherein R$^1$ is a ($C_3$–$C_8$) cycloalkyl ring or ($C_5$–$C_8$) cycloalkenyl ring, wherein either the cycloalkyl ring or cycloalkenyl ring is substituted by one of R$^3$C(O)O—($C_1$–$C_6$)alkyl-, R$^2$ON, R$^2$ON($C_1$–$C_6$)alkyl-, R$^2$ON=CR$^2$($C_1$–$C_6$)alkyl-, —NR$_2$(OR$^2$), R$^4$R$^5$NS(O)2—, R$^4$R$^5$NS(O)2($C_1$–$C_6$)alkyl-, R$^4$S(O)$_2$R$^5$N—, or R$^4$S(O)$_2$R$^5$N($C_1$–$C^6$)alkyl-.

11. The compound of claim 10, wherein R$^1$ is a ($C_3$–$C_8$) cycloalkyl ring or ($C_5$–$C_8$) cycloalkenyl ring, wherein either the cycloalkyl ring or cycloalkenyl ring is substituted by one of R$^3$C(O)O—($C_1$–$C_6$)alkyl-, R$^2$ON, or R$^4$S(O)$_2$R$^5$N—.

12. The compound of claim 10, wherein R$^1$ is substituted by R$^3$C(O)O—($C_1$–$C_6$)alkyl-.

13. The compound of claim 10, wherein R$^1$ is substituted by R$^2$ON=, R$^2$ON=($C_1$–$C_6$)alkyl-, or R$^2$ON=CR$^2$ ($C_1$–$C_6$)alkyl-.

14. The compound of claim 10, wherein R$^1$ is substituted by R$^2$ON=.

15. The compound of claim 10, wherein R$^1$ is substituted by —NR$^2$(OR$^2$).

16. The compound of claim 10, wherein R$^1$ is substituted by R$^4$R$^5$NS(O)$_2$—, R$^4$R$^5$NS(O)$_2$($C_1$–$C_6$)alkyl-, R$^4$S(O)$_2$R$^5$N($C_1$–$C_6$)alkyl-.

17. The compound of claim 1, wherein R$^1$ is substituted by R$^4$S(O)$_2$R$^5$N— or R$^4$S(O)$_2$R$^5$N($C_1$–$C_6$)alkyl-.

18. The compound of claim 1, wherein the ($C_2$–$C_9$) heterocycloalkyl substituent is a group of the formula:

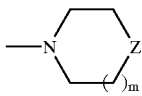

wherein m is 0, 1 or 2, and

Z is $CH_2$, NR, O, S, SO, or $SO_2$.

19. The compound of claim 1 selected from the group consisting of: O-Benzyl-4-(2,4-dihydroxyphenyl) cyclohexanone oxime; (±)-N-[3-(2,4-Dihydroxyphenyl) cyclohexyl]methanesulfonamide; (±)-O-Methyl-3-(2,4-dihydroxyphenyl)cyclohexanone oxime; (±)-O-Benzyl-3-(2,4-dihydroxyphenyl)cyclohexanone oxime; and a pharmaceutically acceptable salt thereof.

20. The compound of claim 1 selected from the group consisting of: O-Methyl-4-(2,4-dihydroxyphenyl) cyclohexanone oxime; (±)-4-[3-(Hydroxyamino) cyclohexyl]-1,3-benzenediol; cis-N-[4-(2,4-Dihydroxyphenyl) cyclohexyl]-1-butanesulfonamide; trans-N-[4-(2,4-Dihydroxyphenyl) cyclohexyl] methanesulfonamide cis-N-[4-(2,4-Dihydroxyphenyl) cyclohexyl]methanesulfonamide; [4-(2,4-Dihydroxyphenyl) cyclohexyl]methyl propionate; cis/trans-4-[4-(hydroxyamino)cyclohexyl]-1,3-benzenediol; trans-4-[4-(methoxyamino)cyclohexyl]-1,3-benzenediol; and a pharmaceutically acceptable salt thereof.

21. A topical pharmaceutical composition for lightening skin or reducing the pigmentation of skin in a human, comprising a pharmaceutically acceptable carrier, and a skin-lightening or pigmentation-reducing amount of a compound of formula I:

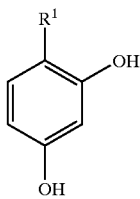

I or a pharmaceutically acceptable salt thereof, wherein:

$R^1$ is a $(C_3-C_8)$cycloalkyl ring or $(C_5-C_8)$cycloalkenyl ring, wherein either the cycloalkyl ring or cycloalkenyl ring is substituted by one to three substituents independently selected from the group consisting of cyano; halo; $(C_1-C_6)$alkyl; aryl; $(C_2-C_9)$heterocycloalkyl; $(C_2-C_9)$heteroaryl; aryl$(C_1-C_6)$alkyl-; =O; =CHO $(C_1-C_6)$alkyl; amino; hydroxy; $(C_1-C_6)$alkoxy; aryl $(C_1-C_6)$alkoxy-; $(C_1-C_6)$acyl; $(C_1-C_6)$alkylamino-; aryl$(C_1-C_6)$alkylamino-; amino$(C_1-C_6)$alkyl-; $(C_1-C_6)$alkoxy-CO—NH—; $(C_1-C_6)$ alkylamino-CO—; $(C_2-C_6)$alkenyl; $(C_2-C_6)$alkynyl; hydroxy $(C_1-C_6)$alkyl-; $(C_1-C_6)$alkoxy$(C_1-C_6)$alkyl-; $(C_1-C_6)$ acyloxy$(C_1-C_6)$alkyl-; nitro; cyano$(C_1-C_6)$alkyl-; halo $(C_1-C_6)$alkyl-; nitro$(C_1-C_6)$alkyl-; trifluoromethyl; trifluoromethyl$(C_1-C_6)$alkyl-; $(C_1-C_6)$acylamino-; $(C_1-C_6)$acylamino$(C_1-C_6)$alkyl-; $(C_1-C_6)$alkoxy $(C_1-C_6)$acylamino-; amino$(C_1-C_6)$acyl-; amino $(C_1-C_6)$acyl$(C_1-C_6)$alkyl-; $(C_1-C_6)$alkylamino $(C_1-C_6)$acyl-; $((C_1-C_6)$ alkyl$)_2$amino$(C_1-C_6)$acyl-; —$CO_2R^2$; —$(C_1-C_6)$alkyl-$CO_2R^2$; —$C(O)N(R^2)_2$; —$(C_1-C_6)$alkyl-C(O)N$(R^2)_2$; $R^2ON=$; $R^2ON=$ $(C_1-C_6)$alkyl-; $R^2ON=CR^2(C_1-C_6)$alkyl-; —$NR^2$ $(OR^2)$; —$(C_1-C_6)$alkyl-$NR^2(OR^2)$; —$C(O)(NR^2R^2)$; —$(C_1-C_6)$alkyl-$C(O)(NR^2OR^2)$; —$S(O)_mR^2$; wherein each $R^2$ is independently selected from hydrogen, $(C_1-C_6)$alkyl, aryl, or aryl$(C_1-C_6)$alkyl-; $R^3C(O)O$—, wherein $R^3$ is $(C_1-C_6)$alkyl, aryl, or aryl$(C_1-C_6)$alkyl-; $R^3C(O)O$—$(C_1-C_6)$alkyl-; $R^4R^5N$—$C(O)$—$O$—; $R^4R^5NS(O)_2$—; $R^4R^5NS(O)_2(C_1-C_6)$alkyl-; $R^4S(O)_2R^5N$—; $R^4S(O)_2R^5N(C_1-C_6)$alkyl-; wherein m is 0, 1 or 2, and $R^4$ and $R^5$ are each independently selected from hydrogen or $(C_1-C_6)$alkyl; —$C(=NR^6)(N(R^4)_2)$; or —$(C_1-C_6)$alkyl-$C(=NR^6)(N(R^4)_2)$ wherein $R^6$ represents $OR^2$ or $R^2$ wherein $R^2$ is defined as above;

with the proviso that the cycloalkenyl ring is not aromatic; with the proviso that $R^1$ must be substituted by at least one of $R^3C(O)O$—, $R^3C(O)O$—$(C_1-C_6)$alkyl-, $R^2ON=$, $R^2ON=(C_1-C_6)$alkyl-, $R^2$ $ON=CR^2(C_1-C_6)$alkyl-, —$NR^2$ $(OR^2)$, $R^4R^5NS(O)_2$—, $R^4R^5NS(O)_2(C_1-C_6)$alkyl-, $R^4S$ $(O)_2$ $R^5N$—, or $R^4S(O)_2R^5N(C_1-C_6)$alkyl-.

22. The composition of claim 21, wherein $R^1$ of the compound is a cyclohexyl or cyclohexenyl ring substituted at the 3- or 4-position, or a cyclopentyl or cyclopentenyl ring substituted at the 3-position.

23. The composition of claim 21, wherein $R^1$ of the compound is monosubstituted.

24. The composition of claim 21, wherein $R^1$ of the compound is disubstituted.

25. The composition of claim 21, wherein $R^1$ of the compound is substituted by at least one of $R^3C(O)O$— or $R^3C(O)O$—$(C_1-C_6)$alkyl-.

26. The composition of claim 21, wherein $R^1$ of the compound is substituted by at least one of $R^2ON=$, $R^2ON=(C_1-C_6)$alkyl-, or $R^2ON=CR^2(C_1-C_6)$alkyl-.

27. The composition of claim 21, wherein $R^1$ of the compound is substituted by at least one of —$NR^2(OR^2)$.

28. The composition of claim 21, wherein $R^1$ of the compound is substituted by at least one of $R^4R^5NS(O)_2$—, $R^4R^5NS(O)_2(C_1-C_6)$alkyl-, $R^4S(O)_2R^5N$—, or $R^4S(O)_2$ $R^5N(CG-C_6)$alkyl-.

29. The composition of claim 21, wherein $R^1$ of the compound is substituted by at least one of $R^4S(O)_2R^5N$— or $R^4S(O)_2R^5N(C_1-C_6)$alkyl-.

30. The composition of claim 21, wherein $R^1$ of the compound is a $(C_3-C_8)$cycloalkyl ring or $(C_5-C_8)$ cycloalkenyl ring, wherein either the cycloalkyl ring or cycloalkenyl ring is substituted by one of $R^3C(O)O$—, $R^3C(O)O$—$(C_1-C_6)$alkyl-, $R^2ON=$, $R^2$ $ON=(C_1-C_6)$ alkyl-, $R^2ON=CR^2(C_1-C_6)$alkyl-, —$NR^2(OR^2)$, $R^4R^5NS$ $(O)_2$—, $R^4R^5NS(O)_2(C_1-C_6)$alkyl-, $R^4S(O)_2R^5N$—, or $R^4S$ $(O)_2R^5N(C_1-C_6)$alkyl-.

31. The composition of claim 30, wherein $R^1$ of the compound is a $(C_3-C_8)$cycloalkyl ring or $(C_5-C_8)$ cycloalkenyl ring, wherein either the cycloalkyl ring or cycloalkenyl ring is substituted by one of $R^3C(O)O$—, $R^3C(O)O$—$(C_1-C_6)$alkyl-, $R^2ON=$, or $R^4S(O)_2R^5N$—.

32. The composition of claim 30, wherein $R^1$ of the compound is substituted by $R^3C(O)O$— $(C_1-C_6)$alkyl-.

33. The composition of claim 30, wherein $R^1$ of the compound is substituted by $R^2ON=$, $R^2ON=(C_1-C_6)$ alkyl-, or $R^2ON=CR^2(C_1-C_6)$alkyl-.

34. The composition of claim 30, wherein $R^1$ of the compound is substituted by $R^2ON=$.

35. The composition of claim 30 wherein $R^1$ of the compound is substituted by —$NR^2(OR^2)$.

36. The composition of claim 30, wherein $R^1$ of the compound is substituted by $R^4R^5NS(O)_2$—, $R^4R^5NS(O)_2$ $(C_1-C_6)$alkyl-, $R^4S(O)_2R^5N$— or $R^4S(O)_2R^5N(C_1-C_6)$ alkyl-.

37. The composition of claim 30, wherein $R^1$ of the compound is substituted by $R^4S(O)_2R^5N$— or $R^4S(O)_2R^5N$ $(C_1-C_6)$alkyl-.

38. The composition of claim 21, wherein the ($C_2$–$C_9$) heterocycloalkyl substituent is a group of the formula:

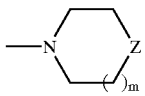

wherein m is 0, 1 or 2, and
Z is $CH_2$, $NR^2$, O, S, SO, or $SO_2$.

39. The composition of claim 21, comprising a compound selected from the group consisting of:

4-(2,4-Dihydroxyphenyl)cyclohexanone oxime; O-Methyl-4-(2,4-dihydroxyphenyl)cyclohexanone oxime; O-Benzyl-4-(2,4-dihydroxyphenyl) cyclohexanone oxime; 3-(2,4-Dihydroxyphenyl)-2-cyclohexen-1-one oxime; (±)-3-(2,4-Dihydroxyphenyl)cyclohexanone oxime; (±)-N-[3-(2,4-dihydroxyphenyl)cyclohexyl]methanesulfonamide; (±)-4-[3-(Hydroxyamino)cyclohexyl]-1,3-benzenediol; (±)-O-Methyl-3-(2,4-dihydroxyphenyl) cyclohexanone oxime; (±)-O-Benzyl-3-(2,4-dihydroxyphenyl)cyclohexanone oxime; 3-(2,4-dihydroxyphenyl)-2-cyclopentenone oxime; (±)-3-(2,4-dihydroxyphenyl)cyclopentanone oxime;

and a pharmaceutically acceptable salt thereof.

40. The composition of claim 21, comprising a compound selected from the group consisting of: cis-N-[4-(2,4-Dihydroxyphenyl)cyclohexyl]-1-butanesulfonamide; trans-N-[4-(2,4-Dihydroxyphenyl)cyclohexyl] methanesulfonamide; cis-N-[4-(2,4-Dihydroxyphenyl) cyclohexyl]methanesulfonamide; [4-(2,4-Dihydroxyphenyl) cyclohexyl]methyl propionate; cis/trans-4-[4-(hydroxyamino)cyclohexyl]-1,3-benzenediol; trans-4-[4-(methoxyamino)cyclohexyl]-1,3-benzenediol;

and a pharmaceutically acceptable salt thereof.

41. The composition of claim 21, wherein the skin-lightening or pigmentation-reducing effective amount of a compound of formula I is a tyrosinase-inhibiting effective amount of the compound.

* * * * *